US010369234B2

(12) United States Patent
Jaskula-Ranga et al.

(10) Patent No.: US 10,369,234 B2
(45) Date of Patent: Aug. 6, 2019

(54) COMPOSITIONS AND METHODS FOR THE EXPRESSION OF CRISPR GUIDE RNAS USING THE H1 PROMOTER

(71) Applicant: The Johns Hopkins University, Baltimore, MD (US)

(72) Inventors: Vinod Jaskula-Ranga, Baltimore, MD (US); Donald Zack, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/864,715

(22) Filed: Jan. 8, 2018

(65) Prior Publication Data
US 2018/0200388 A1   Jul. 19, 2018

Related U.S. Application Data

(60) Division of application No. 14/951,240, filed on Nov. 24, 2015, now Pat. No. 9,907,863, which is a continuation of application No. PCT/US2015/035964, filed on Jun. 16, 2015.

(60) Provisional application No. 62/012,802, filed on Jun. 16, 2014.

(51) Int. Cl.
*A61K 48/00* (2006.01)
*C12N 15/63* (2006.01)
*C12N 15/85* (2006.01)
*C12N 15/90* (2006.01)
*C12N 15/113* (2010.01)
*C12N 15/11* (2006.01)
C12N 15/86 (2006.01)

(52) U.S. Cl.
CPC ........ *A61K 48/0066* (2013.01); *C12N 15/111* (2013.01); *C12N 15/1138* (2013.01); *C12N 15/63* (2013.01); *C12N 15/85* (2013.01); *C12N 15/907* (2013.01); *C07K 2319/10* (2013.01); *C07K 2319/60* (2013.01); *C12N 2310/10* (2013.01); *C12N 2310/20* (2017.05); *C12N 2330/51* (2013.01); *C12N 2750/14133* (2013.01); *C12N 2750/14143* (2013.01); *C12N 2830/85* (2013.01)

(58) Field of Classification Search
CPC ............................ A61K 48/0066; C12N 15/86
See application file for complete search history.

(56) References Cited

U.S. PATENT DOCUMENTS 8,697,359 B1   4/2014  Zhang
9,907,863 B2   3/2018  Jaskula-Ranga et al.

2011/0002892 A1   1/2011  Galloway et al.
2017/0003411 A1   1/2017  Chok et al.
2018/0200388 A1   7/2018  Jaskula-Ranga et al.

FOREIGN PATENT DOCUMENTS

WO   WO-2014/089290 A1   6/2014
WO   WO-2014/186585 A2   11/2014
WO   WO-2015031775 A1    3/2015
WO   WO-2017/004616 A1   1/2017

OTHER PUBLICATIONS

Addgene Press Release, A Match Made in Heaven: CRISPR/Cas9 and AAV, Jul. 14, 2015.
Bio-IT World, New Cas9 Molecule Points the Way to Viral Delivery of CRISPR Systems, Apr. 1, 2015.
Broad Institute Press Release, Broad Institute-MIT Team Indentifies Highly Efficient New CAS9 for In Vivo Genome Editing, Apr. 1, 2015.
Chew, W. L. et al., "A multifunctional AAV-CRISPR-Cas9 and its Host Response," Nature Methods, 13(10):868-879 (2016).
Ding et al., "Enhanced efficiency of human pluripotent stem cell genome editing through replacing TALENs with CRISPRs," Cell Stem Cell, 12(4):393-394 (2013).
Extended European Search Report issued by the European Patent Office in corresponding Application No. EP 15809732.9, dated Mar. 6, 2018.
Fine, E.J. et al., "Trans-spliced Casg Allows Cleavage of HBB and $CCR_5$ Genes in Human Cells Using Compact Expression Cassettes," Scientific Reports, 5:10777:1-9 (2015).
Friedland, A.E. et al., "Characterization of *Staphylococcus aureus* Cas9: a smaller Cas9 for all-in-one adeno-associated virus delivery and paired nickase applications," Genome Biology, 16(257):1-10 (2015).
Gaj, T. et al., "Genome Engineering Using Adeno-associated Virus: Basic and Clinical Research Applications," Molecular Therapy, 24(3):458-464 (2016).
Gao et al., "Self-processing of ribozyme-flanked RNAs into guide RNAs in vitro and in vivo for CRISPR-mediated genome editing," J Integr Plant Biol, 56(4): 343-349 (2014).
Hung et al., "A novel bidirectional expression system for simultaneous expression of both the protein-coding genes and short hairpin RNAs in mammalian cells," Biochem Bioph Res Co, 339: 1035-1042 (2006).
International Search Report and Written Opinion dated Aug. 28, 2015, from related PCT Patent Application No. PCT/US2015/35964.

(Continued)

*Primary Examiner* — Antonio Galisteo Gonzalez
(74) *Attorney, Agent, or Firm* — Foley Hoag LLP

(57) ABSTRACT

The presently disclosed subject matter provides compositions and methods for the expression of CRISPR guide RNAs using the H1 promoter. In particular, compositions and methods are provided for the use of the H1 promoter to express CRISPR guide RNA (gRNA) with altered specificity of the 5' nucleotide, as well as use of the H1 promoter sequence as a bidirectional promoter to express Cas9 nuclease and the gRNA simultaneously. Compositions and methods are also provided for the expression and regulation of gRNA expression in vivo through the use of RNA ribozymes and regulatable aptazymes.

6 Claims, 42 Drawing Sheets

Specification includes a Sequence Listing.

(56) References Cited

OTHER PUBLICATIONS

Kennedy, E.M. et al., "Optimization of a Multiplex CRISPR/Cas System for Use as an Antiviral Therapeutic," Methods, 91:82-86 (2015).

Kennedy, E.M. et al., "Suppression of Hepatitis B Virus DNA Accumulation in Chronically Infected Cells Using a Bacterial CRISPR/CAS RNA-guided DNA Endonuclease," Virology, 476:196-205 (2015).

Komor, A.C. et al., "CRISPR-Based Technologies for the Manipulation of Eukaryotic Genomes," Cell, 168:1-17 (2017).

Ledford, H., "Mini Enzyme Moves Gene Editing Closer to the Clinic," Nature, 520:18 (2015).

Mali, P. et al., "Cas9 as a Versatile Tool for Engineering Biology," Nature Methods, 10(10):957-963 (2013).

Media & Investors Press Release, Editas Medicine Reports New Data Characterizing Novel Properties of *Staphylococcus aureus* Casg as a Tool for CRISPR-Based Genome Engineering, Jan. 12, 2015.

Mefferd, A.L. et al., "Expression of CRISPR/Cas Single Guide RNAs Using Small tRNA Promoters," RNA, 21:1683-1689 (2016).

Nelson, C. E. et al., "In Vivo Genome Editing Improves Muscle Function in a Mouse Model of Duchenne Muscular Dystrophy," Science, 10/1126/science/aad5143 (2015).

Partial Supplementary European Search Report issued by the European Patent Office in corresponding Application No. EP 15809732. 9, dated Nov. 29, 2017.

pCMV beta; pCMV beta map; https://www.addgene.org/browse/sequence/2245/giraffe-analyze_vdb/; pp. 1-2, accessed Feb. 27, 2017.

Qi et al., "A versatile framework for microbial engineering using synthetic non-coding RNAs," Nat Rev Microbiol, 12(5): 341-354 (2014).

Ran, F. A., et al., "In Vivo Genome Editing Using *Staphylococcus aureus* Cas9," Nature, 520:186-203 (2015).

Ranganathan et al., "Expansion of the CRISPR-Cas9 genome targeting space through the use of H1 promoter-expressed guide RNAs," Nat Comm, 5(4516): 1-8 (2014).

Schmidt, F. et al., "CRISPR Genome Engineering and Viral Gene Delivery: A case of mutual attraction," Biotechnol. J., 10:258-272 (2015).

Senis, E. et al., "CRISPR/Cas9-mediated Genome Engineering: An adeno-associated Viral (AAV) Vector Toolbox," Biotechnol. J., 9:1402-1412 (2014).

Swiech, L. et al., "In Vivo Interrogation of Gene Function in the Mammalian Brain Using CRISPR-Cas9," Naure Biotechnology, 33(1):102-110 (2015).

System Bio Press Release, AAV-Cas9 SmartNuclease System, rAAV Vectors for Efficient Cas9-Delivery In Vivo, Downloaded from the Web on Dec. 9, 2016.

Tabebordbar, M. et al., "In Vivo Gene Editing in Dystrophic Mouse Muscle and Muscle Stem Cells," Science 10.1126/science.aad5177 (2015).

Takara Press Release, Helper Virus-Free Preparation of AAV Particles to Deliver Cas9 and sgRNA, Downloaded from Web on Dec. 9, 2016.

The Boston Globe Press Release, Three Cambridge Startups are on a Mission to Fix Broken Genes, May 11, 2016.

The Scientist Magazine Press Release, Enzyme Improves CRISPR: A smaller Cas9 Protein Enables In Vivo Genome Engineering Via Viral Vectors, Apr. 1, 2015.

Turitz Cox, D.B. et al., "Therapeutic Genome Editing: Prospects and Challenges," Nature Medicine, 21(2):121-131 (2015).

Wu et al., "Simple and efficient DNA vector-based RNAi systems in mammalian cells," Biochem Bioph Res Co, 330(1):53-59 (2005).

Wu, "New tools for mammalian mammalian genome engineering with the CRISPR-Cas9 system," System Biosciences, 1-72 (2013).

Yang, Y. et al., "A Dual AAV System Enables the Cas9-mediated Correction of a Metabolic Liver Disease in Newborn Mice," Nature Biotechnology, 34:334-338 (2016).

Yin, H. et al., "Therapeutic Genome Editing by Combined Viral and Non-Viral Delivery of CRISPR System Components in vivo," Nature Biotechnology, 34(3):328-334 (2016).

Wright et al., "Biology and applications of CRISPR systems: Harnessing nature's toolbox for genome engineering," Cell, 164:29-44 (2016).

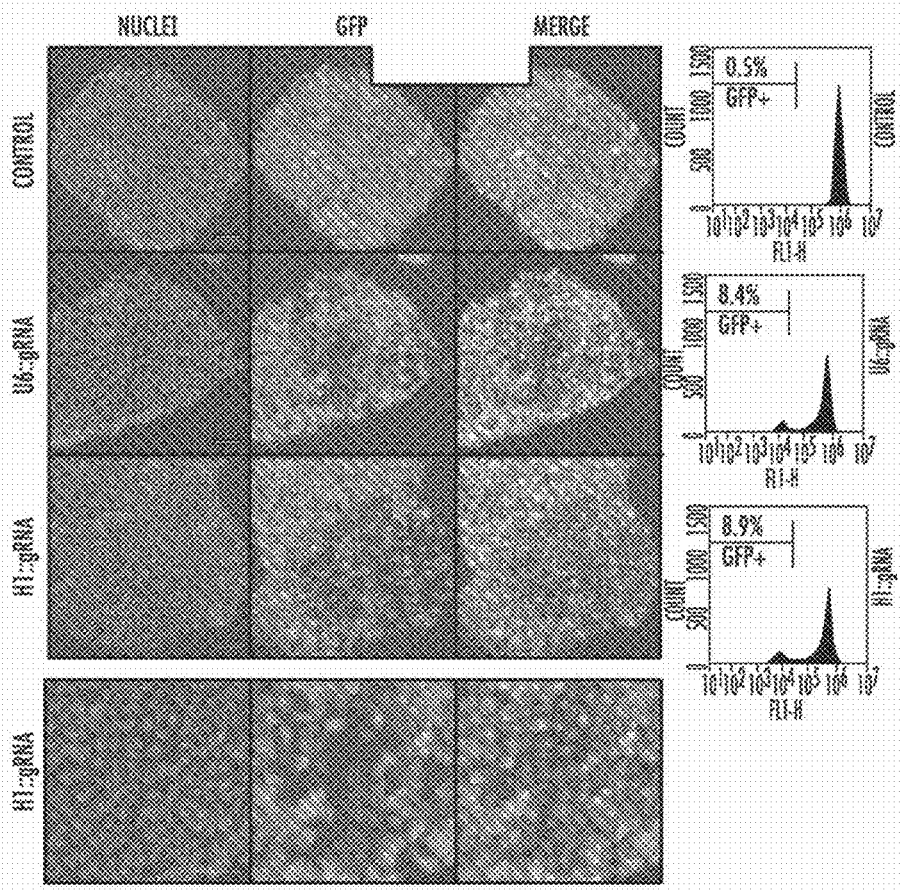

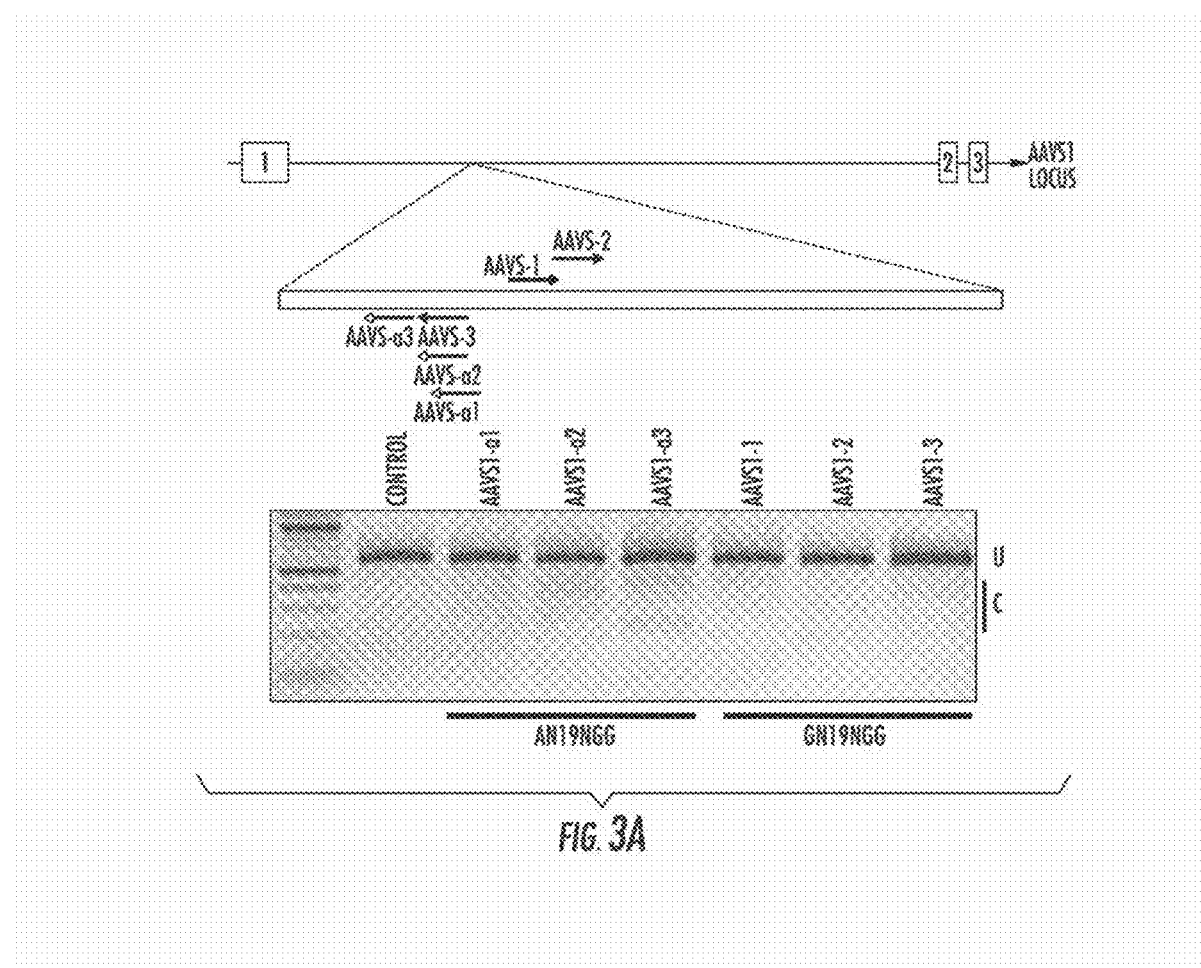

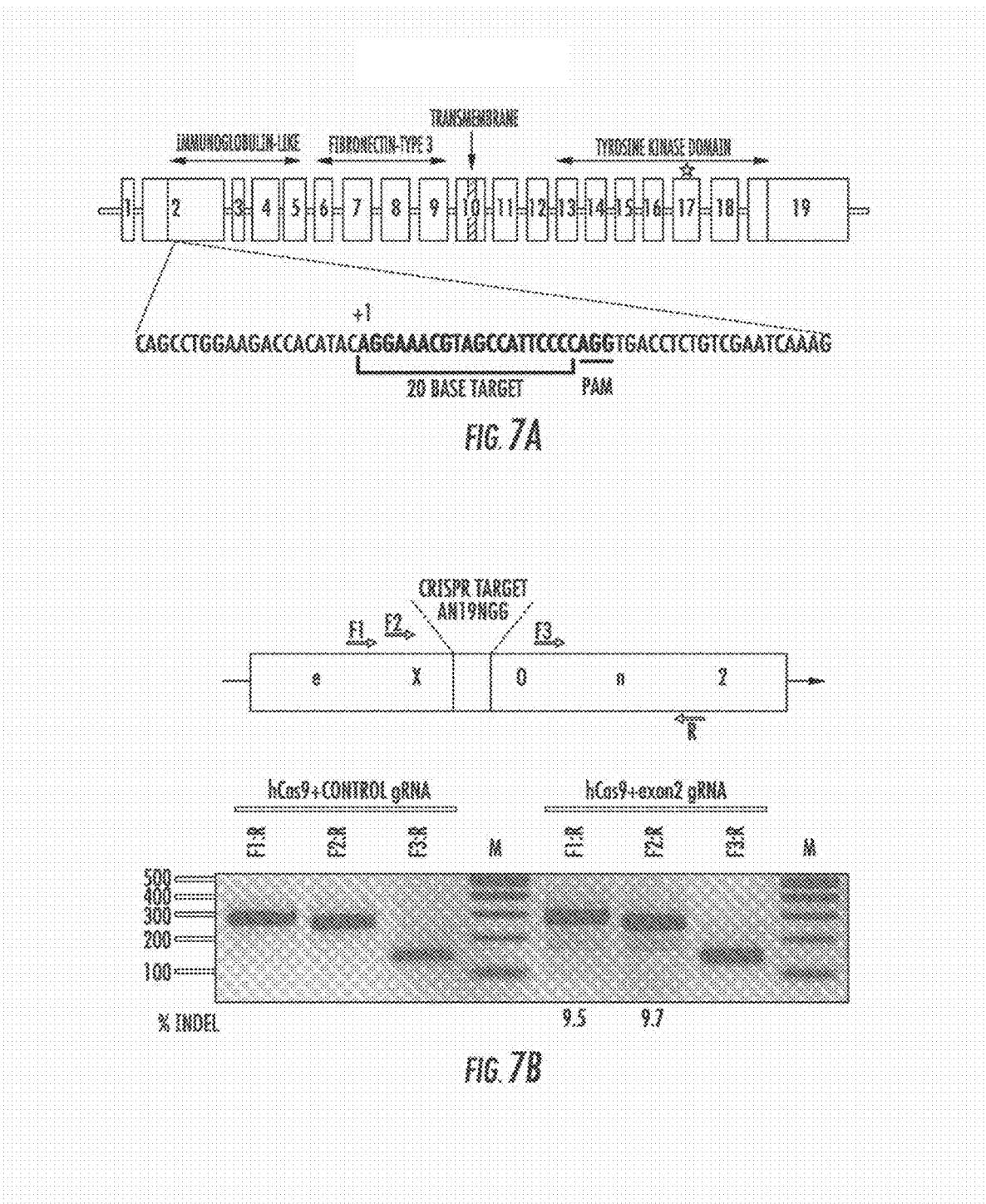

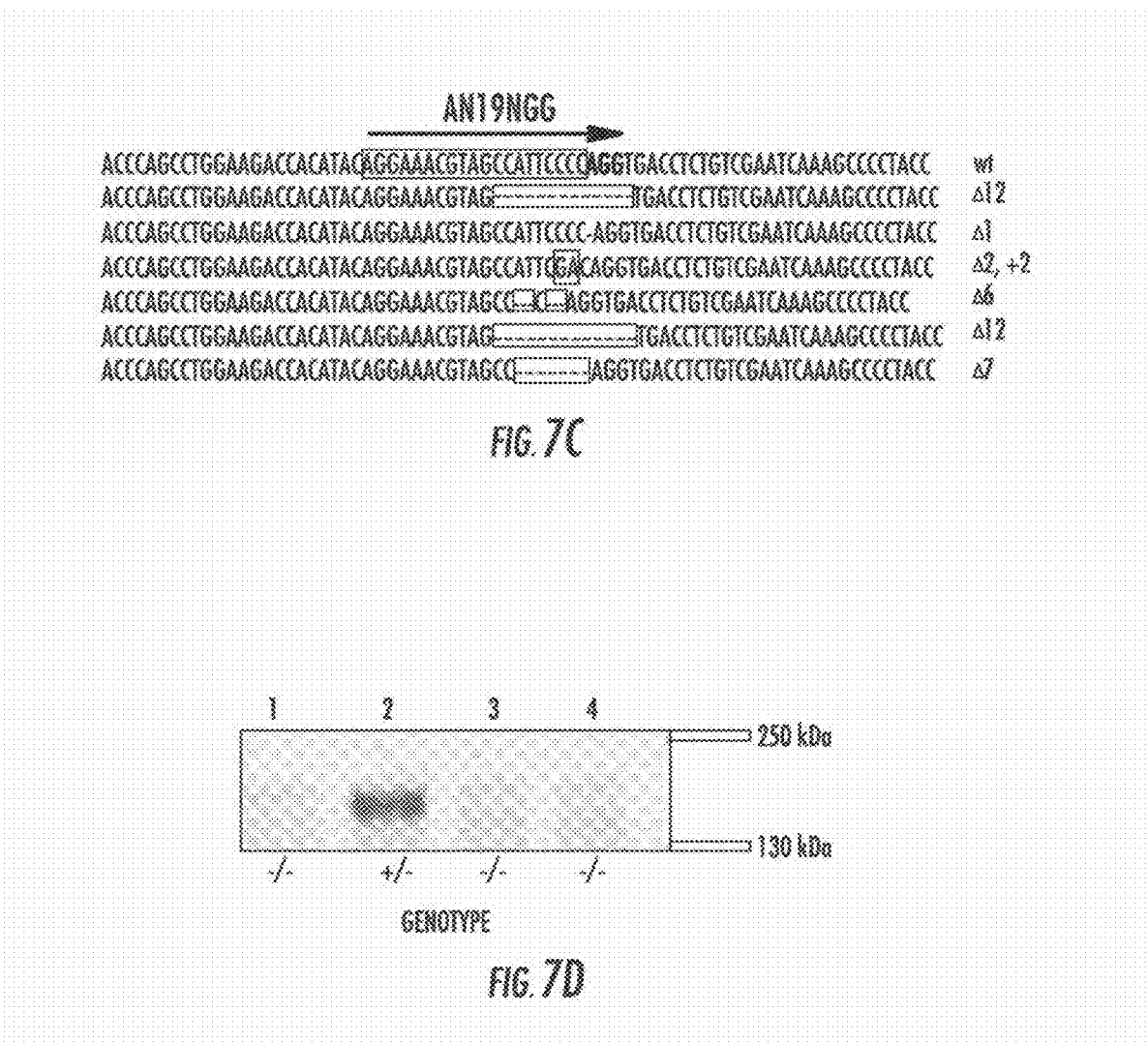

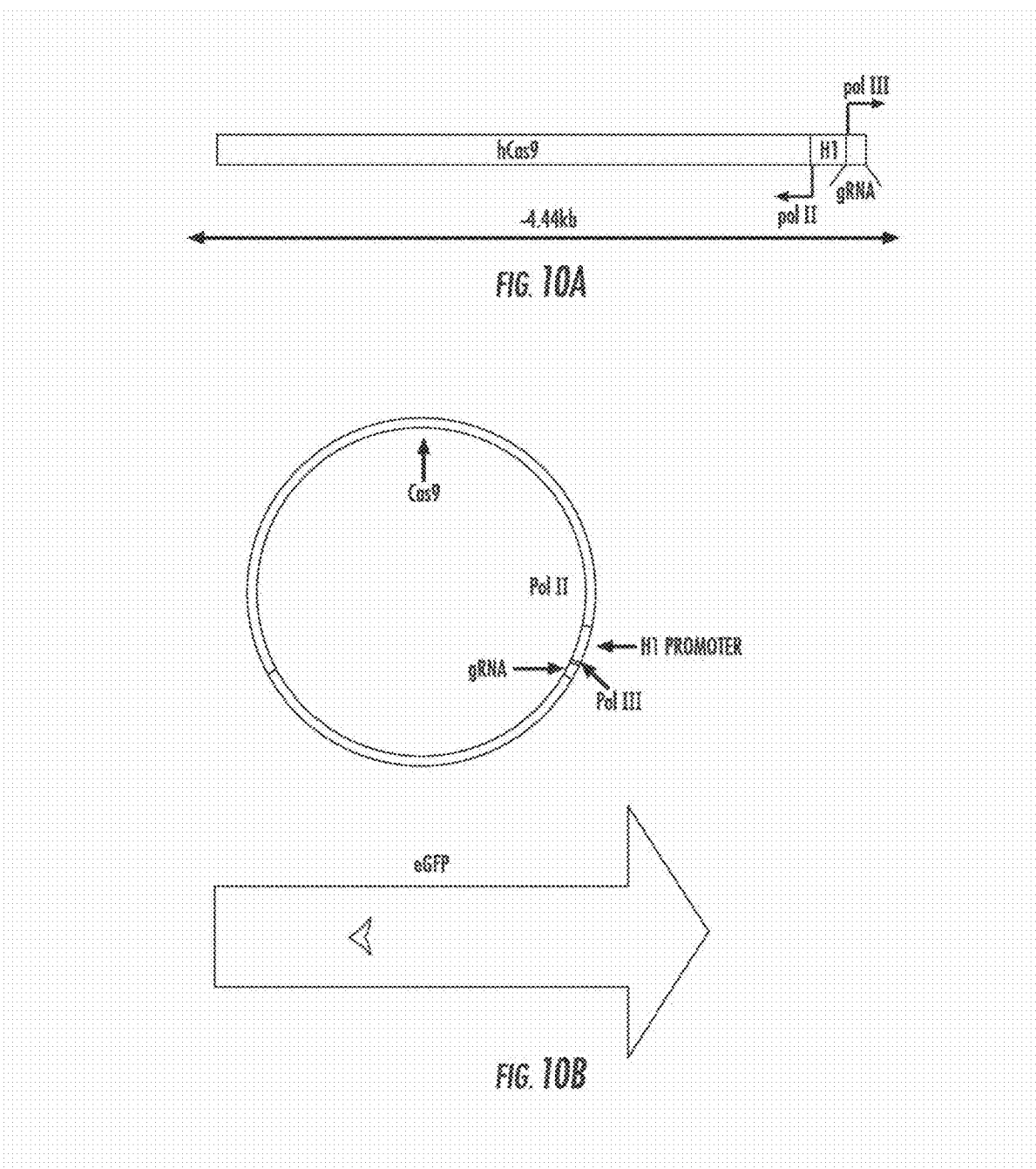

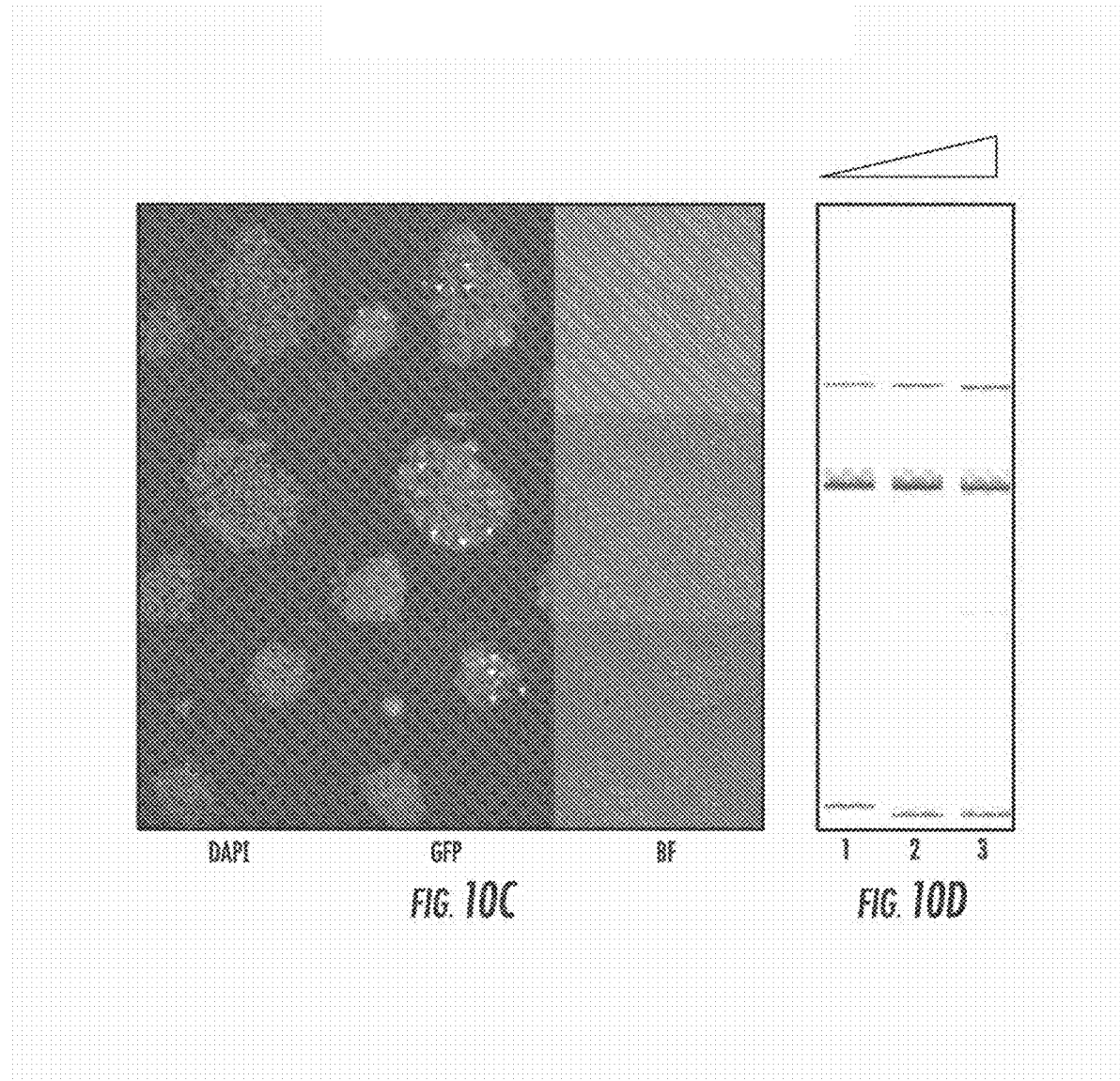

SEQUENCE LISTING

```
<160> NUMBER OF SEQ ID NOS: 59

<210> SEQ ID NO 1
<211> LENGTH: 43
<212> TYPE: DNA
<213> ORGANISM: Artificial Sequence
<220> FEATURE:
<223> OTHER INFORMATION: PCR primer

<400> SEQUENCE: 1
cttcgatgtc gactcgagtc aaaaagcacc gactcggtgc cac          43

<210> SEQ ID NO 2
<211> LENGTH: 26
<212> TYPE: DNA
<213> ORGANISM: Artificial Sequence
<220> FEATURE:
<223> OTHER INFORMATION: PCR primer

<400> SEQUENCE: 2
aaaatatgga acgcttcacg aatttg                              26

<210> SEQ ID NO 3
<211> LENGTH: 27
<212> TYPE: DNA
<213> ORGANISM: Artificial Sequence
<220> FEATURE:
<223> OTHER INFORMATION: PCR primer
```

<400> SEQUENCE: 3
gttttagagc tagaaatagc aagttaa                                    27

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
aagcaccgac tcggtgccac                                            20

<210> SEQ ID NO 5
<211> LENGTH: 23
<212> TYPE: DNA
<213> ORGANISM: Artificial Sequence
<220> FEATURE:
<223> OTHER INFORMATION: PCR primer

<400> SEQUENCE: 5
ctcgcttcgg cagcacatat act                                        23

<210> SEQ ID NO 6
<211> LENGTH: 22
<212> TYPE: DNA
<213> ORGANISM: Artificial Sequence
<220> FEATURE:
<223> OTHER INFORMATION: PCR primer

<400> SEQUENCE: 6
acgcttcacg aatttgcgtg tc                                         22

<210> SEQ ID NO 7
<211> LENGTH: 20
<212> TYPE: DNA
<213> ORGANISM: Artificial Sequence
<220> FEATURE:
<223> OTHER INFORMATION: gRNA targeting sequence

<400> SEQUENCE: 7
gcactgcacg ccgtaggtca                                            20

<210> SEQ ID NO 8
<211> LENGTH: 20
<212> TYPE: DNA
<213> ORGANISM: Artificial Sequence
<220> FEATURE:
<223> OTHER INFORMATION: gRNA targeting sequence

<400> SEQUENCE: 8
agcactgcac gccgtaggtc                                            20

<210> SEQ ID NO 9
<211> LENGTH: 20
<212> TYPE: DNA
<213> ORGANISM: Artificial Sequence
<220> FEATURE:
<223> OTHER INFORMATION: gRNA targeting sequence

<400> SEQUENCE: 9
gctgaagcac tgcacgccgt                                            20

```
<210> SEQ ID NO 10
<211> LENGTH: 19
<212> TYPE: DNA
<213> ORGANISM: Artificial Sequence
<220> FEATURE:
<223> OTHER INFORMATION: gRNA targeting sequence

<400> SEQUENCE: 10
gggcgcacca tcttcttca                                                   19

<210> SEQ ID NO 11
<211> LENGTH: 20
<212> TYPE: DNA
<213> ORGANISM: Artificial Sequence
<220> FEATURE:
<223> OTHER INFORMATION: gRNA targeting sequence

<400> SEQUENCE: 11
accatcttct tcaaggacga                                                  20

<210> SEQ ID NO 12
<211> LENGTH: 20
<212> TYPE: DNA
<213> ORGANISM: Artificial Sequence
<220> FEATURE:
<223> OTHER INFORMATION: gRNA targeting sequence

<400> SEQUENCE: 12
gccgtcgtcc ttgaagaaga                                                  20

<210> SEQ ID NO 13
<211> LENGTH: 20
<212> TYPE: DNA
<213> ORGANISM: Artificial Sequence
<220> FEATURE:
<223> OTHER INFORMATION: gRNA targeting sequence

<400> SEQUENCE: 13
ggtgaaccgc atcgagctga                                                  20

<210> SEQ ID NO 14
<211> LENGTH: 20
<212> TYPE: DNA
<213> ORGANISM: Artificial Sequence
<220> FEATURE:
<223> OTHER INFORMATION: gRNA targeting sequence

<400> SEQUENCE: 14
gtgaaccgca tcgagctgaa                                                  20

<210> SEQ ID NO 15
<211> LENGTH: 20
<212> TYPE: DNA
<213> ORGANISM: Artificial Sequence
<220> FEATURE:
<223> OTHER INFORMATION: gRNA targeting sequence

<400> SEQUENCE: 15
gcacggggcc gtcgccgatg                                                  20

<210> SEQ ID NO 16
<211> LENGTH: 20
<212> TYPE: DNA
<213> ORGANISM: Artificial Sequence
<220> FEATURE:
<223> OTHER INFORMATION: gRNA targeting sequence
```

```
<400> SEQUENCE: 16
agcacggggc cgtcgccgat                                              20

<210> SEQ ID NO 17
<211> LENGTH: 20
<212> TYPE: DNA
<213> ORGANISM: Artificial Sequence
<220> FEATURE:
<223> OTHER INFORMATION: gRNA targeting sequence

<400> SEQUENCE: 17
ggtgctcagg tagtggttgt                                              20

<210> SEQ ID NO 18
<211> LENGTH: 20
<212> TYPE: DNA
<213> ORGANISM: Artificial Sequence
<220> FEATURE:
<223> OTHER INFORMATION: gRNA targeting sequence

<400> SEQUENCE: 18
accgccgccg ggatcactct                                              20

<210> SEQ ID NO 19
<211> LENGTH: 20
<212> TYPE: DNA
<213> ORGANISM: Artificial Sequence
<220> FEATURE:
<223> OTHER INFORMATION: gRNA targeting sequence

<400> SEQUENCE: 19
gtccatgccg agagtgatcc                                              20

<210> SEQ ID NO 20
<211> LENGTH: 23
<212> TYPE: DNA
<213> ORGANISM: Artificial Sequence
<220> FEATURE:
<223> OTHER INFORMATION: gRNA targeting sequence

<400> SEQUENCE: 20
gggtgggggg agtttgctcc tgg                                          23

<210> SEQ ID NO 21
<211> LENGTH: 23
<212> TYPE: DNA
<213> ORGANISM: Artificial Sequence
<220> FEATURE:
<223> OTHER INFORMATION: gRNA targeting sequence

<400> SEQUENCE: 21
ggatggaggg agtttgctcc tgg                                          23

<210> SEQ ID NO 22
<211> LENGTH: 23
<212> TYPE: DNA
<213> ORGANISM: Artificial Sequence
<220> FEATURE:
<223> OTHER INFORMATION: gRNA targeting sequence

<400> SEQUENCE: 22
gggagggtgg agtttgctcc tgg                                          23
```

```
<210> SEQ ID NO 23
<211> LENGTH: 23
<212> TYPE: DNA
<213> ORGANISM: Artificial Sequence
<220> FEATURE:
<223> OTHER INFORMATION: gRNA targeting sequence

<400> SEQUENCE: 23
cgggggaggg agtttgctcc tgg                                              23

<210> SEQ ID NO 24
<211> LENGTH: 23
<212> TYPE: DNA
<213> ORGANISM: Artificial Sequence
<220> FEATURE:
<223> OTHER INFORMATION: gRNA targeting sequence

<400> SEQUENCE: 24
ggggagggga agtttgctcc tgg                                              23

<210> SEQ ID NO 25
<211> LENGTH: 23
<212> TYPE: DNA
<213> ORGANISM: Artificial Sequence
<220> FEATURE:
<223> OTHER INFORMATION: gRNA targeting sequence

<400> SEQUENCE: 25
ggtgagtgag tgtgtgcgtg tgg                                              23

<210> SEQ ID NO 26
<211> LENGTH: 23
<212> TYPE: DNA
<213> ORGANISM: Artificial Sequence
<220> FEATURE:
<223> OTHER INFORMATION: gRNA targeting sequence

<400> SEQUENCE: 26
ggtgagtgag tgtgtgtgtg agg                                              23

<210> SEQ ID NO 27
<211> LENGTH: 23
<212> TYPE: DNA
<213> ORGANISM: Artificial Sequence
<220> FEATURE:
<223> OTHER INFORMATION: gRNA targeting sequence

<400> SEQUENCE: 27
agtgagtgag tgtgtgtgtg agg                                              23

<210> SEQ ID NO 28
<211> LENGTH: 23
<212> TYPE: DNA
<213> ORGANISM: Artificial Sequence
<220> FEATURE:
<223> OTHER INFORMATION: gRNA targeting sequence

<400> SEQUENCE: 28
gctgagtgag tgtatgcgtg tgg                                              23

<210> SEQ ID NO 29
<211> LENGTH: 23
<212> TYPE: DNA
<213> ORGANISM: Artificial Sequence
<220> FEATURE:
<223> OTHER INFORMATION: gRNA targeting sequence
```

```
<400> SEQUENCE: 29
tgtgggtgag tgtgtgcgtg agg                                          23

<210> SEQ ID NO 30
<211> LENGTH: 96
<212> TYPE: RNA
<213> ORGANISM: Artificial Sequence
<220> FEATURE:
<223> OTHER INFORMATION: gRNA targeting sequence
<220> FEATURE:
<221> NAME/KEY: misc_feature
<222> LOCATION: (2)..(20)
<223> OTHER INFORMATION: n is a, c, g, or u

<400> SEQUENCE: 30
annnnnnnnn nnnnnnnnnn guuuuagagc uagaaauagc aaguuaaaau aaggcuaguc   60
cguuaucaac uugaaaaagu ggcaccgagu cggugc                            96

<210> SEQ ID NO 31
<211> LENGTH: 74
<212> TYPE: DNA
<213> ORGANISM: Artificial Sequence
<220> FEATURE:
<223> OTHER INFORMATION: junction region of AAVS1 locus

<400> SEQUENCE: 31
gcctctggcc cactgtttcc ccttcccagg caggtcctgc tttctctgac ctgcattctc   60
tcccctgggc ctgt                                                    74

<210> SEQ ID NO 32
<211> LENGTH: 63
<212> TYPE: DNA
<213> ORGANISM: Homo sapiens

<400> SEQUENCE: 32
cagcctggaa gaccacatac aggaaacgta gccattcccc aggtgacctc tgtcgaatca   60
aag                                                                63

<210> SEQ ID NO 33
<211> LENGTH: 74
<212> TYPE: DNA
<213> ORGANISM: Homo sapiens

<400> SEQUENCE: 33
acccagcctg gaagaccaca tacaggaaac gtagccattc ccaggtgac ctctgtcgaa    60 tcaaagcccc tacc                                                    74

<210> SEQ ID NO 34
<211> LENGTH: 62
<212> TYPE: DNA
<213> ORGANISM: Artificial Sequence
<220> FEATURE:
<223> OTHER INFORMATION: delta 12 mutation of AN19NGG region of MERTK
      gene

<400> SEQUENCE: 34
acccagcctg gaagaccaca tacaggaaac gtagtgacct ctgtcgaatc aaagccccta   60
cc                                                                 62
```

```
<210> SEQ ID NO 35
<211> LENGTH: 73
<212> TYPE: DNA
<213> ORGANISM: Artificial Sequence
<220> FEATURE:
<223> OTHER INFORMATION: delta 1 mutation of AN19NGG region of MERTK
      gene

<400> SEQUENCE: 35
acccagcctg gaagaccaca tacaggaaac gtagccattc ccaggtgacc tctgtcgaat    60
caaagcccct acc                                                      73

<210> SEQ ID NO 36
<211> LENGTH: 74
<212> TYPE: DNA
<213> ORGANISM: Artificial Sequence
<220> FEATURE:
<223> OTHER INFORMATION: delta 2, +2 mutation of AN19NGG region of MERTK
      gene

<400> SEQUENCE: 36
acccagcctg gaagaccaca tacaggaaac gtagccattc gacaggtgac ctctgtcgaa    60
tcaaagcccc tacc                                                     74

<210> SEQ ID NO 37
<211> LENGTH: 68
<212> TYPE: DNA
<213> ORGANISM: Artificial Sequence
<220> FEATURE:
<223> OTHER INFORMATION: delta 6 mutation of AN19NGG region of MERTK
      gene

<400> SEQUENCE: 37
acccagcctg gaagaccaca tacaggaaac gtagcccagg tgacctctgt cgaatcaaag    60
cccctacc                                                            68

<210> SEQ ID NO 38
<211> LENGTH: 67
<212> TYPE: DNA
<213> ORGANISM: Artificial Sequence
<220> FEATURE:
<223> OTHER INFORMATION: delta 7 mutation of AN19NGG region of MERTK
      gene

<400> SEQUENCE: 38
acccagcctg gaagaccaca tacaggaaac gtagccaggt gacctctgtc gaatcaaagc    60
ccctacc                                                             67

<210> SEQ ID NO 39
<211> LENGTH: 60
<212> TYPE: DNA
<213> ORGANISM: Homo sapiens

<400> SEQUENCE: 39
agtatttcga tttcttggct ttatatatct tgtggaaagg acgaaacacc gtgctcgctt    60

<210> SEQ ID NO 40
<211> LENGTH: 20
<212> TYPE: DNA
<213> ORGANISM: Artificial Sequence
<220> FEATURE:
<223> OTHER INFORMATION: U6 promoter and gRNA sequence
```

```
<220> FEATURE:
<221> NAME/KEY: misc_feature
<222> LOCATION: (12)..(20)
<223> OTHER INFORMATION: n is a, c, g, or t

<400> SEQUENCE: 40
acgaaacacc gnnnnnnnnn                                               20

<210> SEQ ID NO 41
<211> LENGTH: 20
<212> TYPE: DNA
<213> ORGANISM: Artificial Sequence
<220> FEATURE:
<223> OTHER INFORMATION: U6 promoter and gRNA sequence
<220> FEATURE:
<221> NAME/KEY: misc_feature
<222> LOCATION: (12)..(15)
<223> OTHER INFORMATION: n is a, c, g, or t
<220> FEATURE:
<221> NAME/KEY: misc_feature
<222> LOCATION: (17)..(20)
<223> OTHER INFORMATION: n is a, c, g, or t

<400> SEQUENCE: 41
acgaaacacc annnngnnnn                                               20

<210> SEQ ID NO 42
<211> LENGTH: 20
<212> TYPE: DNA
<213> ORGANISM: Artificial Sequence
<220> FEATURE:
<223> OTHER INFORMATION: U6 promoter and gRNA sequence
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(20)
<223> OTHER INFORMATION: n is a, c, g, or t

<400> SEQUENCE: 42
acgaaacacc cnngnnnnnn                                               20

<210> SEQ ID NO 43
<211> LENGTH: 20
<212> TYPE: DNA
<213> ORGANISM: Artificial Sequence
<220> FEATURE:
<223> OTHER INFORMATION: U6 promoter and gRNA sequence
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (16)..(20)
<223> OTHER INFORMATION: n is a, c, g, or t

<400> SEQUENCE: 43
acgaaacacc tnnngnnnnn                                               20

<210> SEQ ID NO 44
<211> LENGTH: 59
<212> TYPE: DNA
<213> ORGANISM: Homo sapiens

<400> SEQUENCE: 44
tctttggatt tgggaatctt ataagttctt atgagaccac tctttcccat agggcgga    59
```

```
<210> SEQ ID NO 45
<211> LENGTH: 19
<212> TYPE: DNA
<213> ORGANISM: Artificial Sequence
<220> FEATURE:
<223> OTHER INFORMATION: H1 promoter and gRNA sequence
<220> FEATURE:
<221> NAME/KEY: misc_feature
<222> LOCATION: (11)..(19)
<223> OTHER INFORMATION: n is a, c, g, or t

<400> SEQUENCE: 45
actctttccg nnnnnnnnn                                                   19

<210> SEQ ID NO 46
<211> LENGTH: 20
<212> TYPE: DNA
<213> ORGANISM: Artificial Sequence
<220> FEATURE:
<223> OTHER INFORMATION: H1 promoter and gRNA sequence
<220> FEATURE:
<221> NAME/KEY: misc_feature
<222> LOCATION: (12)..(20)
<223> OTHER INFORMATION: n is a, c, g, or t

<400> SEQUENCE: 46
actctttccc annnnnnnnn                                                  20

<210> SEQ ID NO 47
<211> LENGTH: 20
<212> TYPE: DNA
<213> ORGANISM: Artificial Sequence
<220> FEATURE:
<223> OTHER INFORMATION: H1 promoter and gRNA sequence
<220> FEATURE:
<221> NAME/KEY: misc_feature
<222> LOCATION: (12)..(20)
<223> OTHER INFORMATION: n is a, c, g, or t

<400> SEQUENCE: 47
actctttccc cnnnnnnnnn                                                  20

<210> SEQ ID NO 48
<211> LENGTH: 20
<212> TYPE: DNA
<213> ORGANISM: Artificial Sequence
<220> FEATURE:
<223> OTHER INFORMATION: H1 promoter and gRNA sequence
<220> FEATURE:
<221> NAME/KEY: misc_feature
<222> LOCATION: (12)..(20)
<223> OTHER INFORMATION: n is a, c, g, or t

<400> SEQUENCE: 48
actctttccc tnnnnnnnnn                                                  20

<210> SEQ ID NO 49
<211> LENGTH: 143
<212> TYPE: RNA
<213> ORGANISM: Artificial Sequence
<220> FEATURE:
<223> OTHER INFORMATION: ribozyme
<220> FEATURE:
<221> NAME/KEY: misc_feature
<222> LOCATION: (1)..(143)
<223> OTHER INFORMATION: n is a, u, c, or g
```

<400> SEQUENCE: 49
nnnnnnnnnn cugaugaguc cgugaggacg aaacgaggaa acucgucnnn nnnnnnnnnn    60
nnnnnnnguu uuagagcuag aaauagcaag uuaaaauaag gcuaguccgu uaucaacuug   120
aaaaaguggc accgagucgg ugc                                          143

<210> SEQ ID NO 50
<211> LENGTH: 96
<212> TYPE: RNA
<213> ORGANISM: Artificial Sequence
<220> FEATURE:
<223> OTHER INFORMATION: ribozyme
<220> FEATURE:
<221> NAME/KEY: misc_feature
<222> LOCATION: (1)..(96)
<223> OTHER INFORMATION: n is a, u, c, or g

<400> SEQUENCE: 50
nnnnnnnnnn nnnnnnnnnn guuuuagagc uagaaauagc aaguuaaaau aaggcuaguc    60
cguuaucaac uugaaaaagu ggcaccgagu cggugc                             96

<210> SEQ ID NO 51
<211> LENGTH: 23
<212> TYPE: DNA
<213> ORGANISM: Artificial Sequence
<220> FEATURE:
<223> OTHER INFORMATION: target site for hammerhead ribozyme

<400> SEQUENCE: 51
ctcacctcta cgccagagcg cgg                                           23

<210> SEQ ID NO 52
<211> LENGTH: 23
<212> TYPE: DNA
<213> ORGANISM: Artificial Sequence
<220> FEATURE:
<223> OTHER INFORMATION: target site for hammerhead ribozyme

<400> SEQUENCE: 52
aggaaacgta gccattcccc agg                                           23

<210> SEQ ID NO 53
<211> LENGTH: 52
<212> TYPE: DNA
<213> ORGANISM: Artificial Sequence
<220> FEATURE:
<223> OTHER INFORMATION: hammerhead sequence

<400> SEQUENCE: 53 gtacgttttcc tctgatgagt cccaaatagg acgaaacgcg cttcggtgcg tc          52

<210> SEQ ID NO 54
<211> LENGTH: 230
<212> TYPE: DNA
<213> ORGANISM: Artificial Sequence
<220> FEATURE:
<223> OTHER INFORMATION: H1 sequence

<400> SEQUENCE: 54
ggaattcgaa cgctgacgtc atcaacccgc tccaaggaat cgcgggccca gtgtcactag    60
gcgggaacac ccagcgcgcg tgcgccctgg caggaagatg gctgtgaggg acaggggagt   120
ggcgccctgc aatatttgca tgtcgctatg tgttctggga aatcaccata aacgtgaaat   180
gtctttggat ttgggaatct tataagttct gtatgagacc acttttttccc             230

```
<210> SEQ ID NO 55
<211> LENGTH: 82
<212> TYPE: RNA
<213> ORGANISM: Artificial Sequence
<220> FEATURE:
<223> OTHER INFORMATION: ribozyme
<220> FEATURE:
<221> NAME/KEY: misc_feature
<222> LOCATION: (1)..(82)
<223> OTHER INFORMATION: n is a, u, c, or g

<400> SEQUENCE: 55
nnnnnnnnnn cugaugagau accagccgaa aggcccuugg cagugaaacg aggaaacucg      60
ucnnnnnnnn nnnnnnnnnn nn                                              82

<210> SEQ ID NO 56
<211> LENGTH: 27
<212> TYPE: DNA
<213> ORGANISM: Mus musculus

<400> SEQUENCE: 56
agccccttcg agcagccgca gtactac                                         27

<210> SEQ ID NO 57
<211> LENGTH: 27
<212> TYPE: DNA
<213> ORGANISM: Mus musculus

<400> SEQUENCE: 57
agccacttcg agcagccgca gtactac                                         27

<210> SEQ ID NO 58
<211> LENGTH: 27
<212> TYPE: DNA
<213> ORGANISM: Mus musculus

<400> SEQUENCE: 58 agcccttttcg agcagccgca gtactac                                        27

<210> SEQ ID NO 59
<211> LENGTH: 9
<212> TYPE: PRT
<213> ORGANISM: Mus musculus

<400> SEQUENCE: 59

Ser Pro Phe Glu Gln Pro Gln Tyr Tyr
1               5
```

COMPOSITIONS AND METHODS FOR THE EXPRESSION OF CRISPR GUIDE RNAS USING THE H1 PROMOTER

CROSS-REFERENCE TO RELATED APPLICATIONS

This application is Divisional application of U.S. application Ser. No 14/951,240, filed on Nov. 24, 2015, now allowed, which is a continuation of International Application No. PCT/US15/35964 having an international filing date of Jun. 16, 2015, which claims the benefit of U.S. Provisional Application No. 62/012,802, filed Jun. 16, 2014, the contents which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Aug. 27, 2017, is named JHV-15625_ST25.txt and is 14 KB in size.

INCORPORATION-BY-REFERENCE OF MATERIAL SUBMITTED ELECTRONICALLY

This application contains a sequence listing. It has been submitted electronically via EFS-Web as an ASCII text file entitled "111232-00401_ST25.txt". The sequence listing is 14,827 bytes in size, and was created on Jun. 2, 2015. It is hereby incorporated herein by reference in its entirety.

BACKGROUND

Clustered Regularly Interspaced Short Palindromic Repeats (CRISPR) together with cas (CRISPR-associated) genes comprise an adaptive immune system that provides acquired resistance against invading foreign nucleic acids in bacteria and archaea (Barrangou et al. (2007) *Science* 315: 1709-12). CRISPR consists of arrays of short conserved repeat sequences interspaced by unique variable DNA sequences of similar size called spacers, which often originate from phage or plasmid DNA (Barrangou et al. (2007) *Science* 315:1709-12; Bolotin et al. (2005) *Microbiology* 151:2551-61; Mojica et al. (2005) *J. Mol. Evol.* 60:174-82). The CRISPR-Cas system functions by acquiring short pieces of foreign DNA (spacers) which are inserted into the CRISPR region and provide immunity against subsequent exposures to phages and plasmids that carry matching sequences (Barrangou et al. (2007) *Science* 315:1709-12; Brouns et al. (2008) *Science* 321:960-64). It is this CRISPR-Cas interference/immunity that enables crRNA-mediated silencing of foreign nucleic acids (Horvath & Barrangou (2010) *Science* 327:167-70; Deveau et al. (2010) *Annu. Rev. Microbiol.* 64:475-93; Marraffini & Sontheimer (2010) *Nat. Rev. Genet.* 11:181-90; Bhaya et al. (2011)*Annu. Rev. Genet.* 45:273-97; Wiedenheft et al. (2012) *Nature* 482:331-338).

Use of CRISPR constructs that rely upon the nuclease activity of the Cas9 protein (Makarova et al. (2011) *Nat. Rev. Microbiol.* 9:467-77) coupled with a synthetic guide RNA (gRNA) has recently revolutionized genomic-engineering, allowing for unprecedented manipulation of DNA sequences. CRISPR/Cas9 constructs are simple and fast to synthesize and can be multiplexed. However, despite the relative ease of their synthesis, CRISPRs have technological restrictions related to their access to targetable genome space, which is a function of both the properties of Cas9 itself and the synthesis of its gRNA.

Cleavage by the CRISPR system requires complementary base pairing of the gRNA to a 20-nucleotide DNA sequence and the requisite protospacer-adjacent motif (PAM), a short nucleotide motif found 3' to the target site (Jinek et al. (2012) *Science* 337: 816-821). One can, theoretically, target any unique $N_{20}$-PAM sequence in the genome using CRISPR technology. The DNA binding specificity of the PAM sequence, which varies depending upon the species of origin of the specific Cas9 employed, provides one constraint. Currently, the least restrictive and most commonly used Cas9 protein is from *S. pyogenes*, which recognizes the sequence NGG, and thus, any unique 21-nucleotide sequence in the genome followed by two guanosine nucleotides ($N_{20}$NGG) can be targeted. Expansion of the available targeting space imposed by the protein component is limited to the discovery and use of novel Cas9 proteins with altered PAM requirements (Cong et al. (2013) *Science* 339: 819-823; Hou et al. (2013) *Proc. Natl. Acad. Sci. U.S.A.* 110 (39):15644-9), or pending the generation of novel Cas9 variants via mutagenesis or directed evolution.

The second technological constraint of the CRISPR system arises from gRNA expression initiating at a 5' guanosine nucleotide. Use of the type III class of RNA polymerase III promoters has been particularly amenable for gRNA expression because these short non-coding transcripts have well-defined ends, and all the necessary elements for transcription, with the exclusion of the 1+ nucleotide, are contained in the upstream promoter region. However, since the commonly used U6 promoter requires a guanosine nucleotide to initiate transcription, use of the U6 promoter has further constrained genomic targeting sites to $GN_{19}NGG$ (Mali et al. (2013) *Science* 339:823-826; Ding et al. (2013) *Cell Stem Cell* 12:393-394). Alternative approaches, such as in vitro transcription by T7, T3, or SP6 promoters, would also require initiating guanosine nucleotide(s) (Adhya et al. (1981) *Proc. Natl. Acad. Sci. U.S.A.* 78:147-151; Melton et al. (1984) *Nucleic Acids Res.* 12:7035-7056; Pleiss et al. (1998) *RNA* 4:1313-1317).

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science, and Current Protocols in Cell Biology*, all John Wiley & Sons, N.Y., edition as of Dec. 2008; Sambrook, Russell, and Sambrook, *Molecular Cloning. A Laboratory Manual*, 3rd ed., Cold Spring Harbor Laboratory Press, Cold Spring Harbor, 2001; Harlow, E. and Lane, D., *Antibodies—A Laboratory Manual*, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange $10^{th}$ ed. (2006) or 11th edition (Jul. 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, available on the World Wide Web. and in Online Mendelian Inheritance in Animals (OMIA), a database of genes, inherited disorders and traits in animal species (other than human and mouse), available on the World Wide Web. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings are used herein unless indicated otherwise. Standard abbreviations for various terms are used herein.

The presently disclosed subject matter provides compositions and methods for the expression of CRISPR guide RNAs using the H1 promoter. The presently disclosed subject matter provides a non-naturally occurring CRISPR-Cas system comprising one or more vectors comprising: a) an H1 promoter operably linked to at least one nucleotide sequence encoding a CRISPR-Cas system guide RNA (gRNA), wherein the gRNA hybridizes with a target sequence of a DNA molecule in a cell, and wherein the DNA molecule encodes one or more gene products expressed in the cell; and b) a regulatory element operable in a cell operably linked to a nucleotide sequence encoding a Cas9 protein, wherein components (a) and (b) are located on the same or different vectors of the system, wherein the gRNA targets and hybridizes with the target sequence and the Cas9 protein cleaves the DNA molecule to alter expression of the one or more gene products. In some aspects, the target sequence comprises the nucleotide sequence $AN_{19}NGG$, $GN_{19}NGG$, $CN_{19}NGG$, or $TN_{19}NGG$. In some aspects, the cell is a eukaryotic cell. In some aspects, the eukaryotic cell is a mammalian or human cell. In some aspects, the eukaryotic cell is a retinal photoreceptor cell. In some aspects, the Cas9 protein is codon optimized for expression in the cell. In some aspects, the Cas9 protein is a Type-II Cas9 protein. In some aspects, the expression of the one or more gene products is decreased. In some aspects, the one or more gene products are rhodopsin. In some aspects, the system is packaged into a single adeno-associated virus (AAV) particle.

In some aspects, the presently disclosed subject matter provides a non-naturally occurring CRISPR-Cas system comprising one or more vectors comprising: a) an H1 promoter operably linked to at least one nucleotide sequence encoding a CRISPR-Cas system guide RNA (gRNA), wherein the gRNA hybridizes with a target sequence of a DNA molecule in a eukaryotic cell, and wherein the DNA molecule encodes one or more gene products expressed in the eukaryotic cell; and b) a regulatory element operable in a eukaryotic cell operably linked to a nucleotide sequence encoding a Type-II Cas9 protein, wherein components (a) and (b) are located on the same or different vectors of the system, whereby the gRNA targets and hybridizes with the target sequence and the Cas9 protein cleaves the DNA molecule, and whereby expression of the one or more gene products is altered. In another aspect, the target sequence comprises the nucleotide sequence $AN_{19}NGG$, $GN_{19}NGG$, $CN_{19}NGG$, or $TN_{19}NGG$. In another aspect, the Cas9 protein is codon optimized for expression in the cell. In yet another aspect, the Cas9 protein is codon optimized for expression in the eukaryotic cell. In a further aspect, the eukaryotic cell is a mammalian or human cell. In another aspect, the expression of the one or more gene products is decreased.

The presently disclosed subject matter also provides a method of altering expression of one or more gene products in a cell, wherein the cell comprises a DNA molecule encoding the one or more gene products, the method comprising introducing into the cell a non-naturally occurring CRISPR-Cas system comprising one or more vectors comprising: a) an H1 promoter operably linked to at least one nucleotide sequence encoding a CRISPR-Cas system guide RNA (gRNA), wherein the gRNA hybridizes with a target sequence of the DNA molecule; and b) a regulatory element operable in the cell operably linked to a nucleotide sequence encoding a Cas9 protein, wherein components (a) and (b) are located on the same or different vectors of the system, wherein the gRNA targets and hybridizes with the target sequence and the Cas9 protein cleaves the DNA molecule to alter expression of the one or more gene products. In some aspects, the target sequence comprises the nucleotide sequence $AN_{19}NGG$, $GN_{19}NGG$, $CN_{19}NGG$, or $TN_{19}NGG$. In some aspects, the cell is a eukaryotic cell. In some aspects, the eukaryotic cell is a mammalian or human cell. In some aspects, the eukaryotic cell is a retinal photoreceptor cell. In some aspects, the Cas9 protein is codon optimized for expression in the cell. In some aspects, the Cas9 protein is a Type-II Cas9 protein. In some aspects, the expression of the one or more gene products is decreased. In some aspects, the one or more gene products are rhodopsin. In some aspects, the system is packaged into a single adeno-associated virus (AAV) particle.

In some aspects, the presently disclosed subject matter provides a method of altering expression of one or more gene products in a eukaryotic cell, wherein the cell comprises a DNA molecule encoding the one or more gene products, the method comprising introducing into the cell a non-naturally occurring CRISPR-Cas system comprising one or more vectors comprising: a) an H1 promoter operably linked to at least one nucleotide sequence encoding a CRISPR-Cas system guide RNA (gRNA), wherein the gRNA hybridizes with a target sequence of the DNA molecule; and b) a regulatory element operable in the eukaryotic cell operably linked to a nucleotide sequence encoding a Type-II Cas9 protein, wherein components (a) and (b) are located on the same or different vectors of the system, whereby the gRNA targets and hybridizes with the target sequence and the Cas9 protein cleaves the DNA molecule, and whereby expression of the one or more gene products is altered. In another aspect, the target sequence comprises the nucleotide sequence $AN_{19}NGG$, $GN_{19}NGG$, $CN_{19}NGG$, or $TN_{19}NGG$. In another aspect, the Cas9 protein is codon optimized for expression in the cell. In yet another aspect, the Cas9 protein is codon optimized for expression in the eukaryotic cell. In a further aspect, the eukaryotic cell is a mammalian or human cell. In another aspect, the expression of the one or more gene products is decreased.

The presently disclosed subject matter also provides a non-naturally occurring CRISPR-Cas system comprising a vector comprising a bidirectional H1 promoter, wherein the bidirectional H1 promoter comprises: a) control elements that provide for transcription in one direction of at least one nucleotide sequence encoding a CRISPR-Cas system guide RNA (gRNA), wherein the gRNA hybridizes with a target sequence of a DNA molecule in a cell, and wherein the DNA molecule encodes one or more gene products expressed in the cell; and b) control elements that provide for transcription in the opposite direction of a nucleotide sequence encoding a Cas9 protein, wherein the gRNA targets and hybridizes with the target sequence and the Cas9 protein cleaves the DNA molecule to alter expression of the one or more gene products. In some aspects, the target sequence comprises the nucleotide sequence $AN_{19}$ NGG, $GN_{19}NGG$, $CN_{19}NGG$, or $TN_{19}NGG$. In some aspects, the cell is a eukaryotic cell. In some aspects, the eukaryotic cell is a mammalian or human cell. In some aspects, the eukaryotic cell is a retinal photoreceptor cell. In some aspects, the Cas9 protein is codon optimized for expression in the cell. In some aspects, the Cas9 protein is a Type-II Cas9 protein. In some aspects, the expression of the one or more gene products is decreased. In some aspects, the one or more gene products are rhodopsin. In some aspects, the system is packaged into a single adeno-associated virus (AAV) particle.

In some embodiments, the presently disclosed subject matter provides a non-naturally occurring CRISPR-Cas system comprising a vector comprising a bidirectional H1 promoter, wherein the bidirectional H1 promoter comprises: a) control elements that provide for transcription in one direction of at least one nucleotide sequence encoding a CRISPR-Cas system guide RNA (gRNA), wherein the gRNA hybridizes with a target sequence of a DNA molecule in a eukaryotic cell, and wherein the DNA molecule encodes one or more gene products expressed in the eukaryotic cell; and b) control elements that provide for transcription in the opposite direction of a nucleotide sequence encoding a Type-II Cas9 protein, whereby the gRNA targets and hybridizes with the target sequence and the Cas9 protein cleaves the DNA molecule, and whereby expression of the one or more gene products is altered. In another aspect, the target sequence comprises the nucleotide sequence $AN_{19}$ NGG, $GN_{19}NGG$, $CN_{19}NGG$, or $TN_{19}NGG$. In yet another aspect, the Cas9 protein is codon optimized for expression in the eukaryotic cell. In a further aspect, the eukaryotic cell is a mammalian or human cell. In another aspect, the expression of the one or more gene products is decreased.

The presently disclosed subject matter also provides a method of altering expression of one or more gene products in a cell, wherein the cell comprises a DNA molecule encoding the one or more gene products, the method comprising introducing into the cell a non-naturally occurring CRISPR-Cas system comprising a vector comprising a bidirectional H1 promoter, wherein the bidirectional H1 promoter comprises: a) control elements that provide for transcription in one direction of at least one nucleotide sequence encoding a CRISPR-Cas system guide RNA (gRNA), wherein the gRNA hybridizes with a target sequence of the DNA molecule; and b) control elements that provide for transcription in the opposite direction of a nucleotide sequence encoding a Cas9 protein, wherein the gRNA targets and hybridizes with the target sequence and the Cas9 protein cleaves the DNA molecule to alter expression of the one or more gene products in the cell. In some aspects, the target sequence comprises the nucleotide sequence $AN_{19}NGG$, $GN_{19}NGG$, $CN_{19}NGG$, or $TN_{19}NGG$. In some aspects, the cell is a eukaryotic cell. In some aspects, the eukaryotic cell is a mammalian or human cell. In some aspects, the eukaryotic cell is a retinal photoreceptor cell. In some aspects, the Cas9 protein is codon optimized for expression in the cell. In some aspects, the Cas9 protein is a Type-II Cas9 protein. In some aspects, the expression of the one or more gene products is decreased. In some aspects, the one or more gene products are rhodopsin. In some aspects, the system is packaged into a single adeno-associated virus (AAV) particle.

The presently disclosed subject matter also provides a method of altering expression of one or more gene products in a eukaryotic cell, wherein the cell comprises a DNA molecule encoding the one or more gene products, the method comprising introducing into the cell a non-naturally occurring CRISPR-Cas system comprising a vector comprising a bidirectional H1 promoter, wherein the bidirectional H1 promoter comprises: a) control elements that provide for transcription in one direction of at least one nucleotide sequence encoding a CRISPR-Cas system guide RNA (gRNA), wherein the gRNA hybridizes with a target sequence of the DNA molecule; and b) control elements that provide for transcription in the opposite direction of a nucleotide sequence encoding a Type-II Cas9 protein, whereby the gRNA targets and hybridizes with the target sequence and the Cas9 protein cleaves the DNA molecule, and whereby expression of the one or more gene products is altered. In another aspect, the target sequence comprises the nucleotide sequence $AN_{19}NGG$, $GN_{19}NGG$, $CN_{19}NGG$, or $TN_{19}NGG$. In yet another aspect, the Cas9 protein is codon optimized for expression in the eukaryotic cell. In a further aspect, the eukaryotic cell is a mammalian or human cell. In another aspect, the expression of the one or more gene products is decreased.

The presently disclosed subject matter also provides an aptamer-regulated ribozyme, comprising: a) a cis-acting hammerhead ribozyme comprising a catalytic core and helix I, helix II, and helix III duplex regions extending therefrom, wherein the helix II duplex region and the helix III duplex region each comprise a loop region opposite the catalytic core, and wherein the helix II duplex region comprises an aptamer that binds to a ligand; b) a nucleotide sequence encoding a CRISPR-Cas system guide RNA (gRNA), wherein the gRNA hybridizes with a target sequence of a DNA molecule in a eukaryotic cell, and wherein the DNA molecule encodes one or more gene products expressed in the eukaryotic cell, wherein the nucleotide sequence comprises a 5' end and a 3' end, and wherein the 5' end of the nucleotide sequence is directly coupled to the helix III duplex region; wherein binding of the ligand to the aptamer produces a conformational change in the ribozyme such that the ribozyme undergoes self-cleavage between the 5' end of the nucleotide sequence and the helix III duplex region, whereby the gRNA is produced. An expression construct is also provided comprising: (i) a coding sequence which, when transcribed to RNA, produces the aptamer-regulated ribozyme; and (ii) one or more transcriptional regulatory sequences that regulate transcription of the RNA in a eukaryotic cell. A eukaryotic cell comprising the expression construct is also provided. A method of altering expression of one or more gene products in a eukaryotic cell is also provided, wherein the cell comprises a DNA molecule encoding the one or more gene products, the method comprising introducing the expression construct into the cell and contacting the cell with the ligand in an amount that alters the activity of the ribozyme, particularly wherein the cell is in mammalian or human subject. In one aspect, the ligand is theophylline.

The presently disclosed subject matter also provides a method for treating an ocular neurodegenerative disease in a subject in need thereof, the method comprising: (a) providing a non-naturally occurring CRISPR-Cas system comprising one or more vectors comprising: i) an H1 promoter operably linked to at least one nucleotide sequence encoding a CRISPR-Cas system guide RNA (gRNA), wherein the gRNA hybridizes with a target sequence of a DNA molecule in a cell of the subject, and wherein the DNA molecule encodes one or more gene products expressed in the cell; and ii) a regulatory element operable in a cell operably linked to a nucleotide sequence encoding a Cas9 protein, wherein components (i) and (ii) are located on the same or different vectors of the system, wherein the gRNA targets and hybridizes with the target sequence and the Cas9 protein cleaves the DNA molecule to alter expression of the one or more gene products; and (b) administering to the subject an effective amount of the system. In some aspects, the dysfunction and/or death of retinal photoreceptor cells has been observed in the subject. In some aspects, the ocular neurodegenerative disease is selected from the group consisting of glaucoma, retinal degeneration, and age-related macular degeneration. In some aspects, the ocular neurodegenerative disease is retinitis pigmentosa (RP). In some aspects, the cell is a retinal photoreceptor cell. In some aspects, one or more gene products are rhodopsin. In some aspects, the H1 promoter is bidirectional. In some aspects, the system is packaged into a single adeno-associated virus (AAV) particle before administering to the subject. In some aspects, administering to the subject occurs by subretinal injection. In some aspects, the subject is a human. In some aspects, the Cas9 protein is a Type-II Cas9 protein. In some aspects, the target sequence comprises the nucleotide sequence $AN_{19}NGG$, $GN_{19}NGG$, $CN_{19}NGG$, or $TN_{19}NGG$. In some aspects, the Cas9 protein is codon optimized for expression in the cell. In some aspects, the presently disclosed method further comprises administering the expression construct and the ligand in an amount that alters the activity of the ribozyme. In some aspects, the ligand is theophylline.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
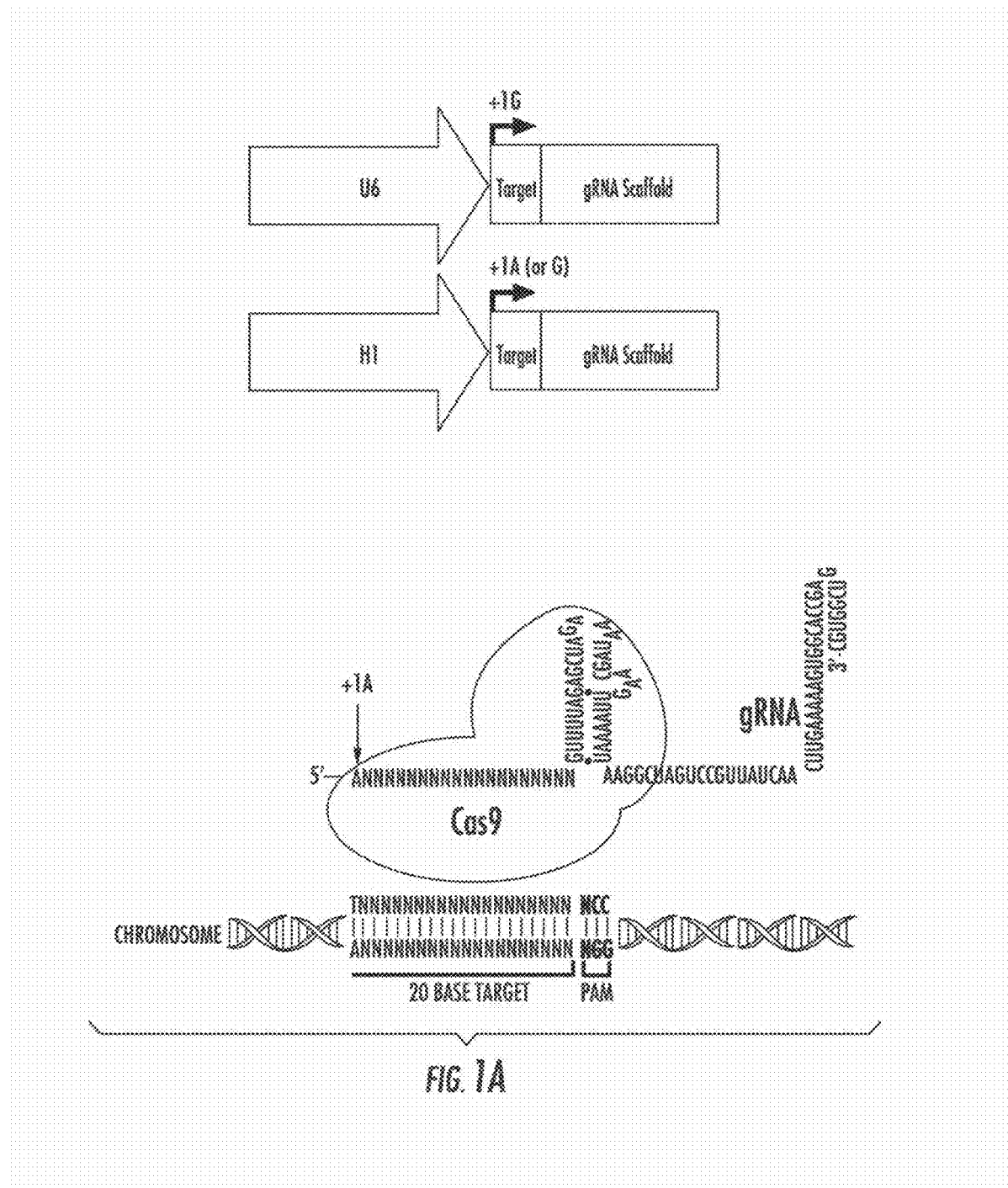
Figure 1D:
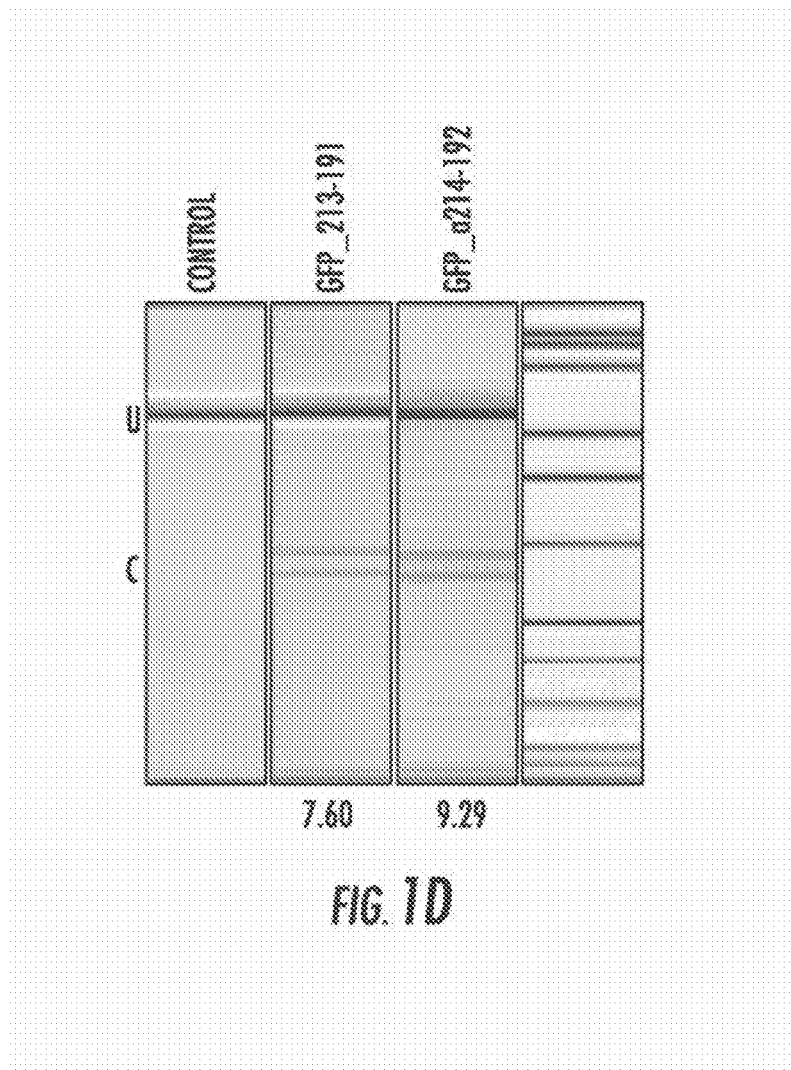
Figure 2:
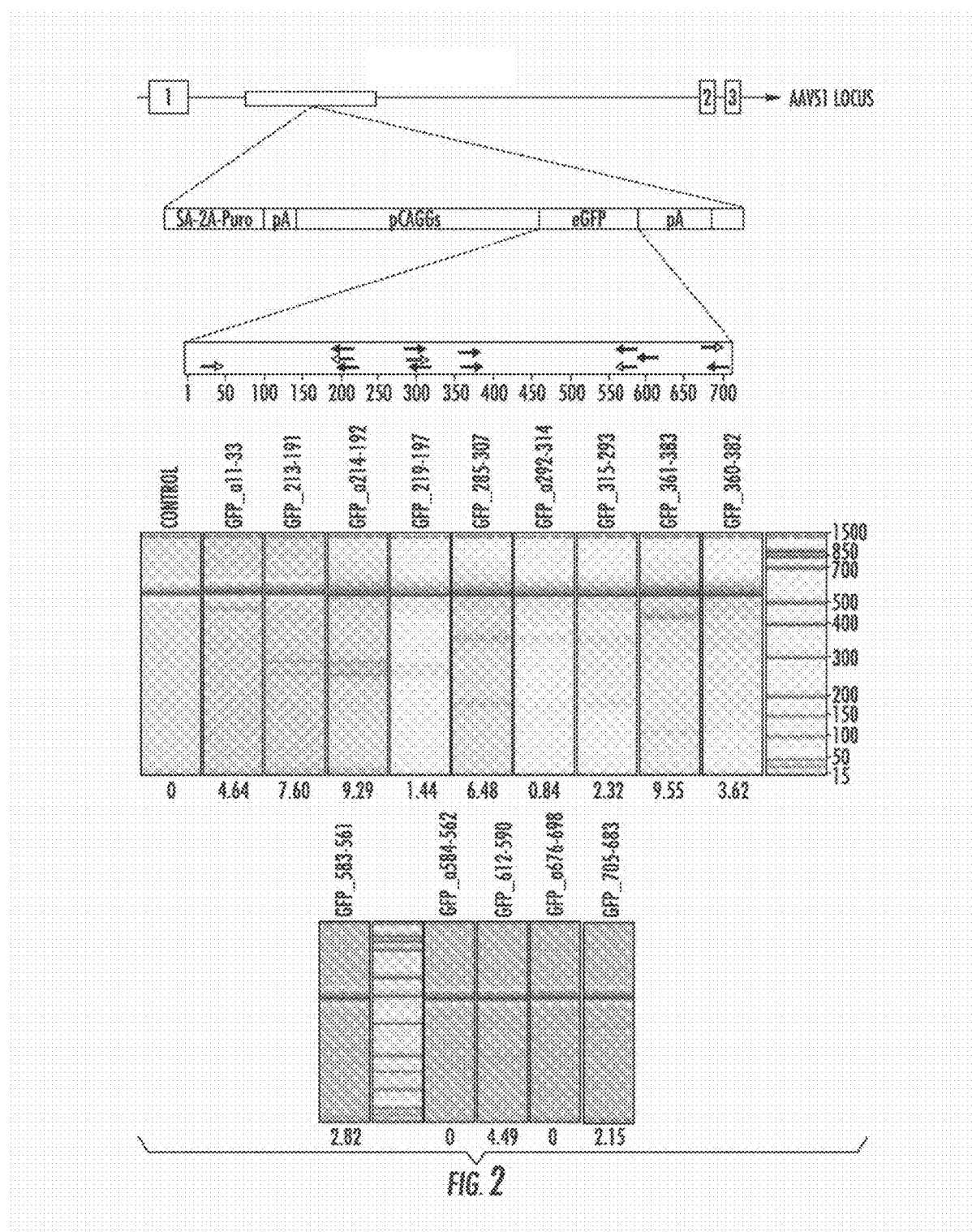
Figure 3B:
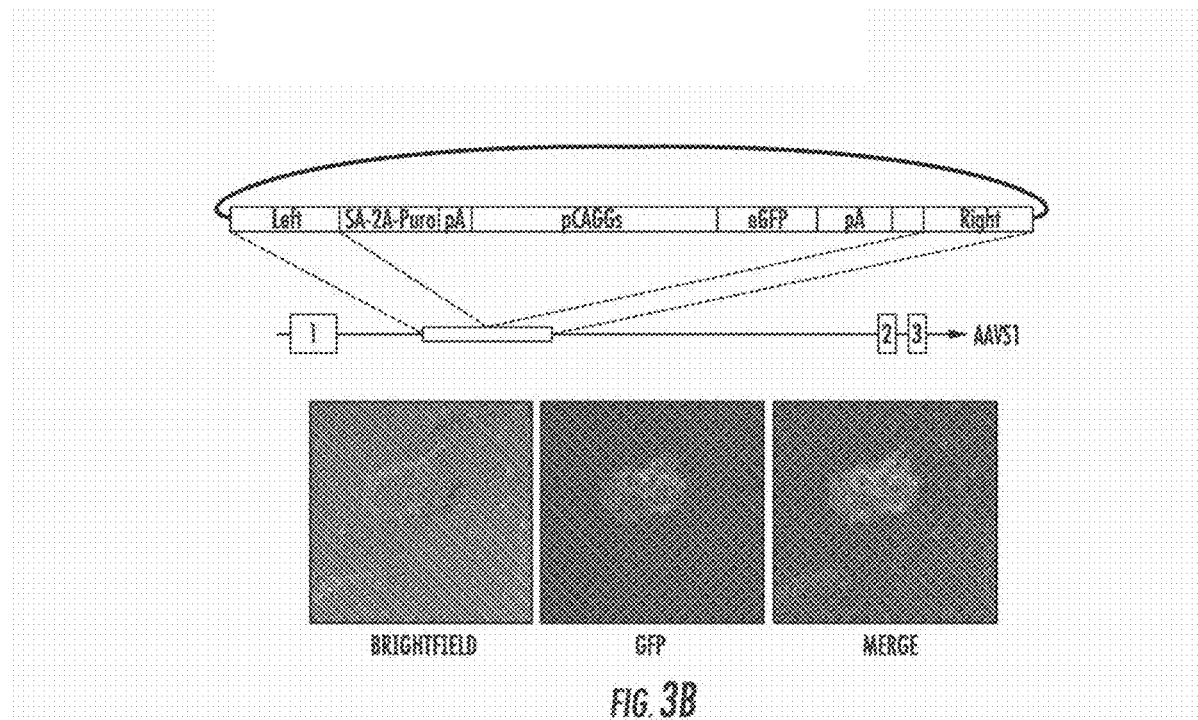
Figure 3C:
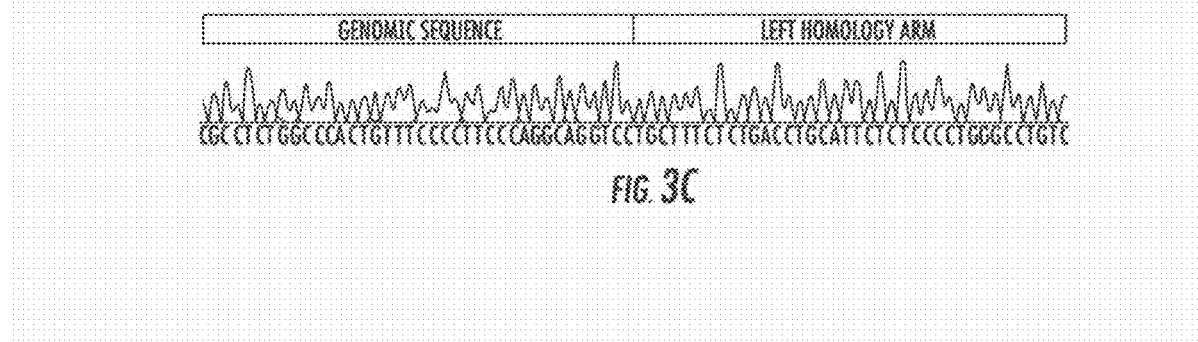
Figure 4A:
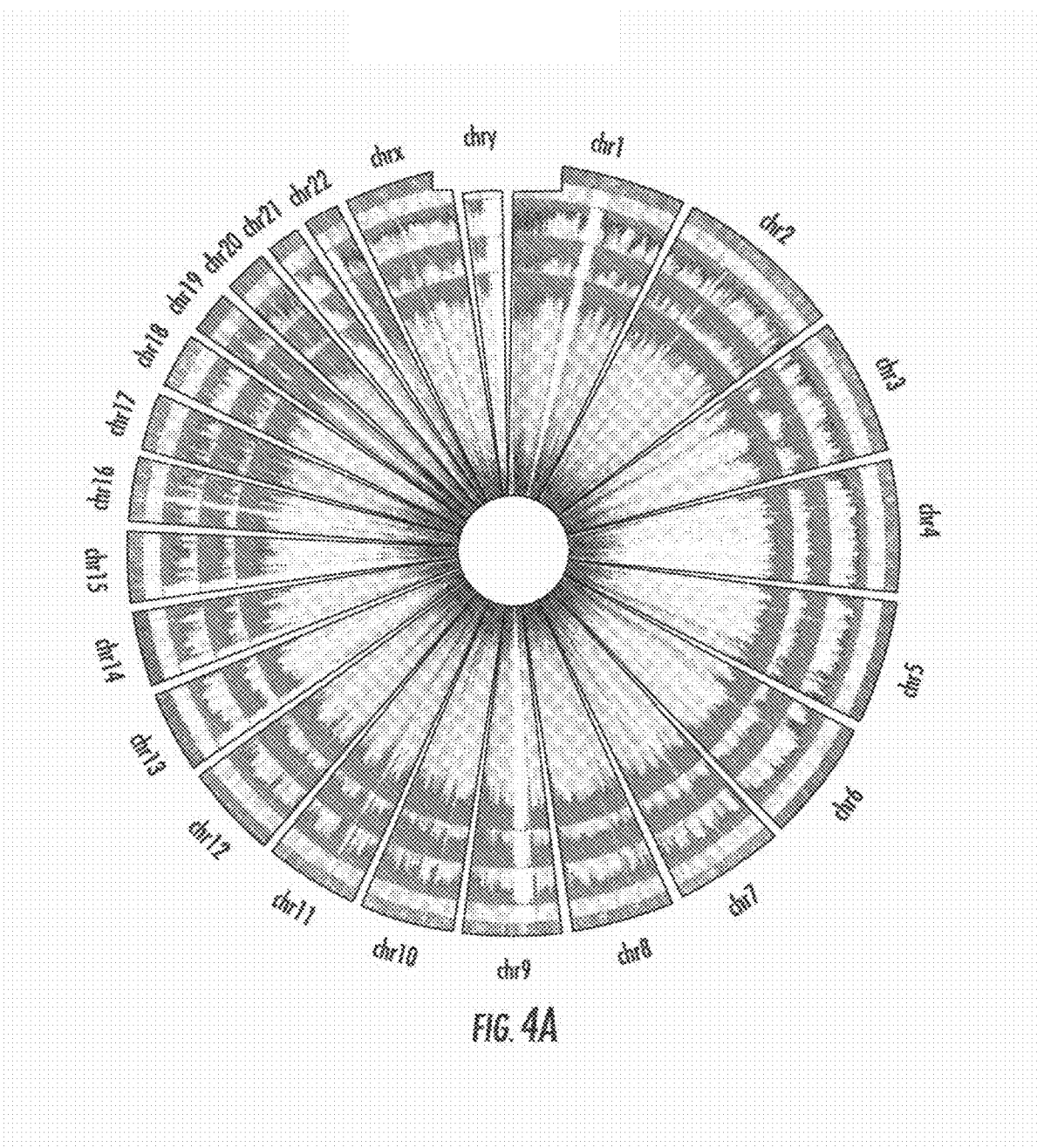
Figure 4B:
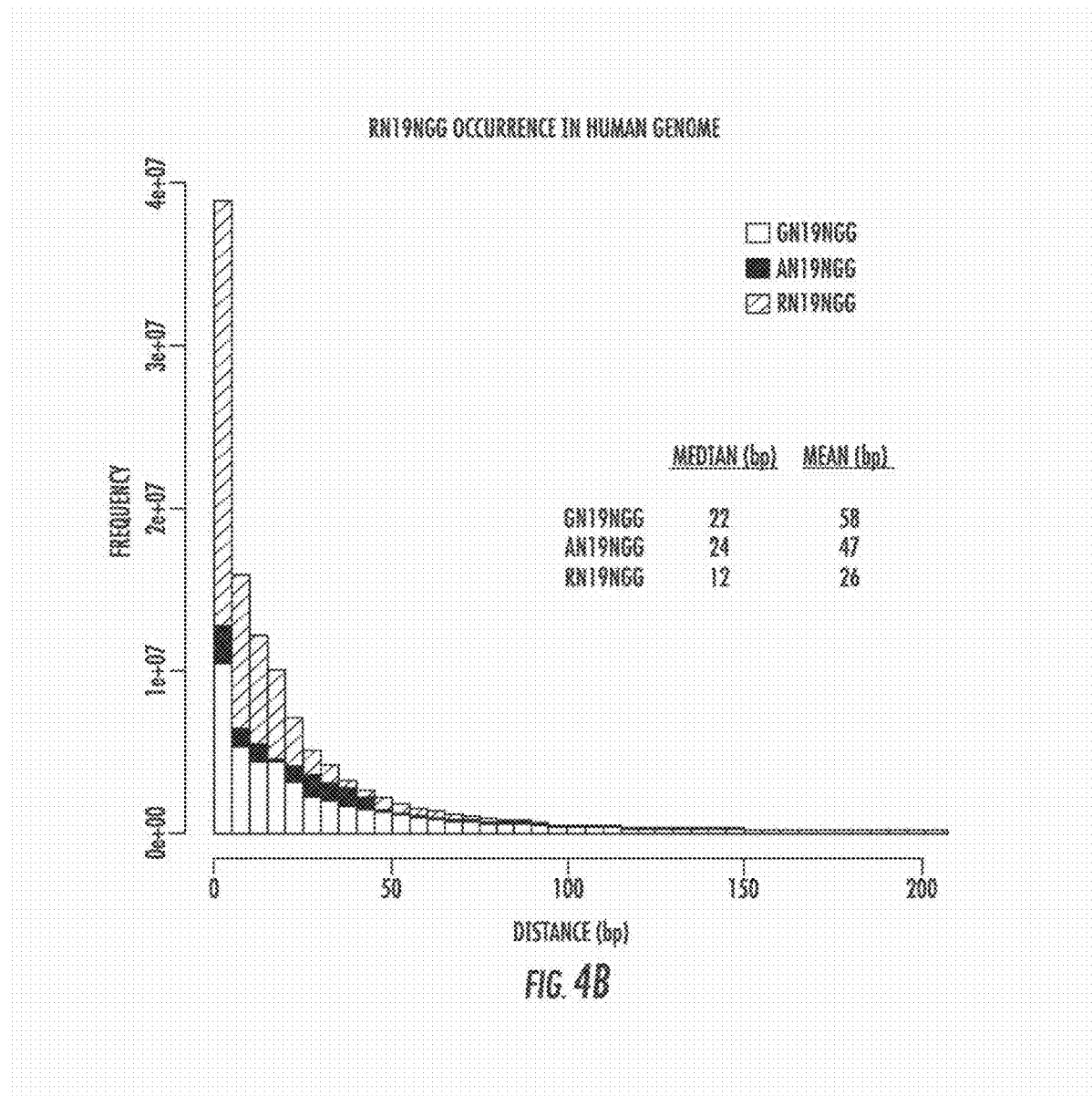
Figure 4C:
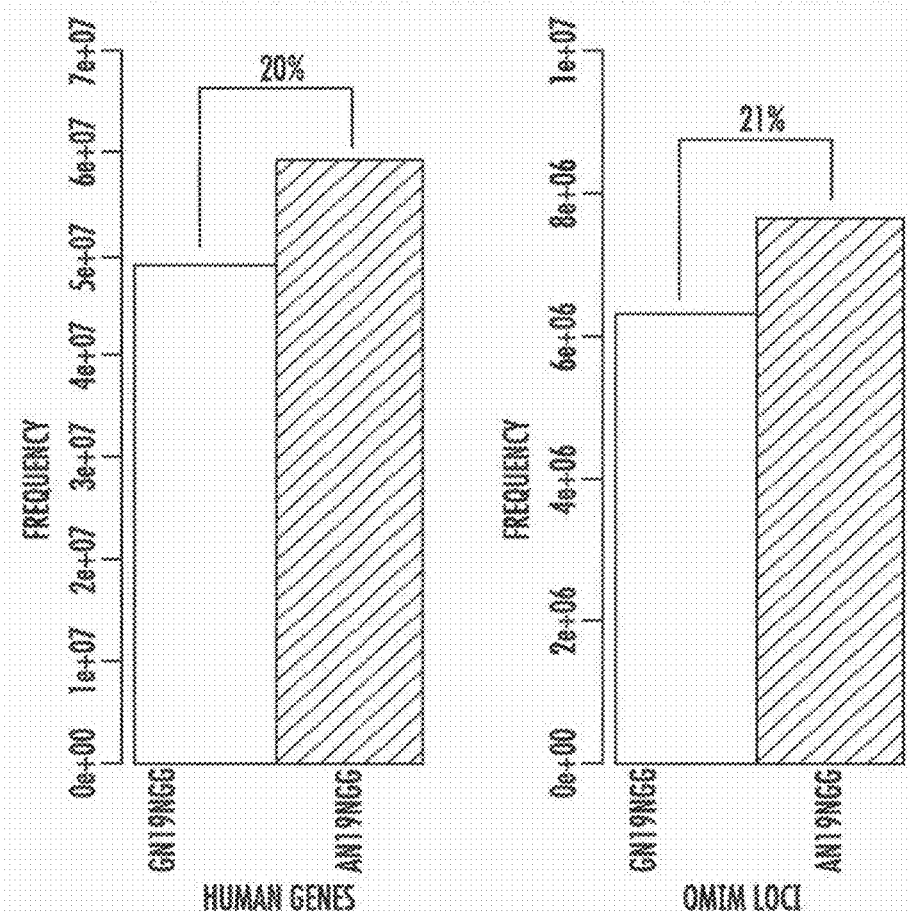
Figure 4D:
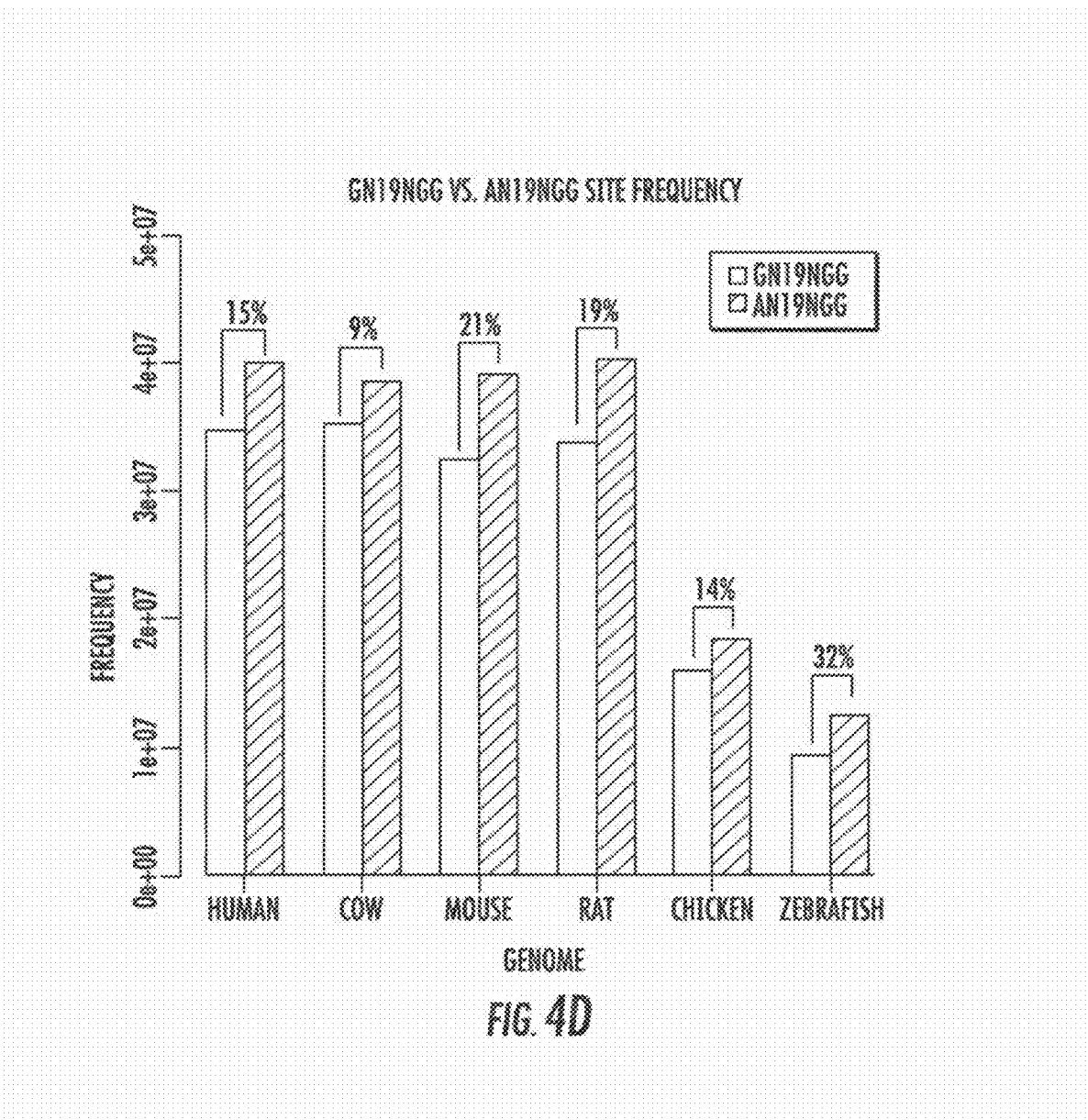
Figure 5A:
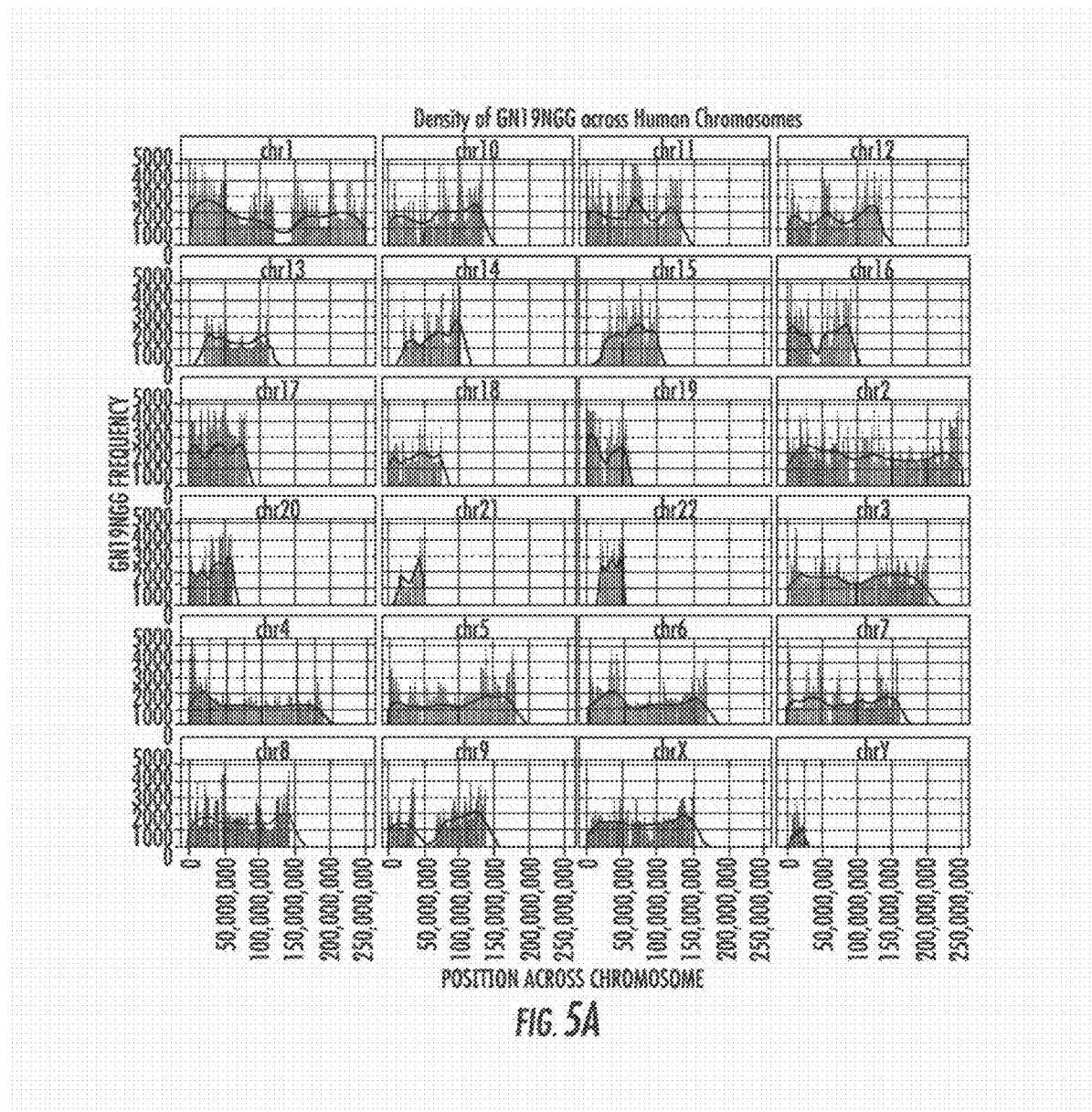
Figure 5B:
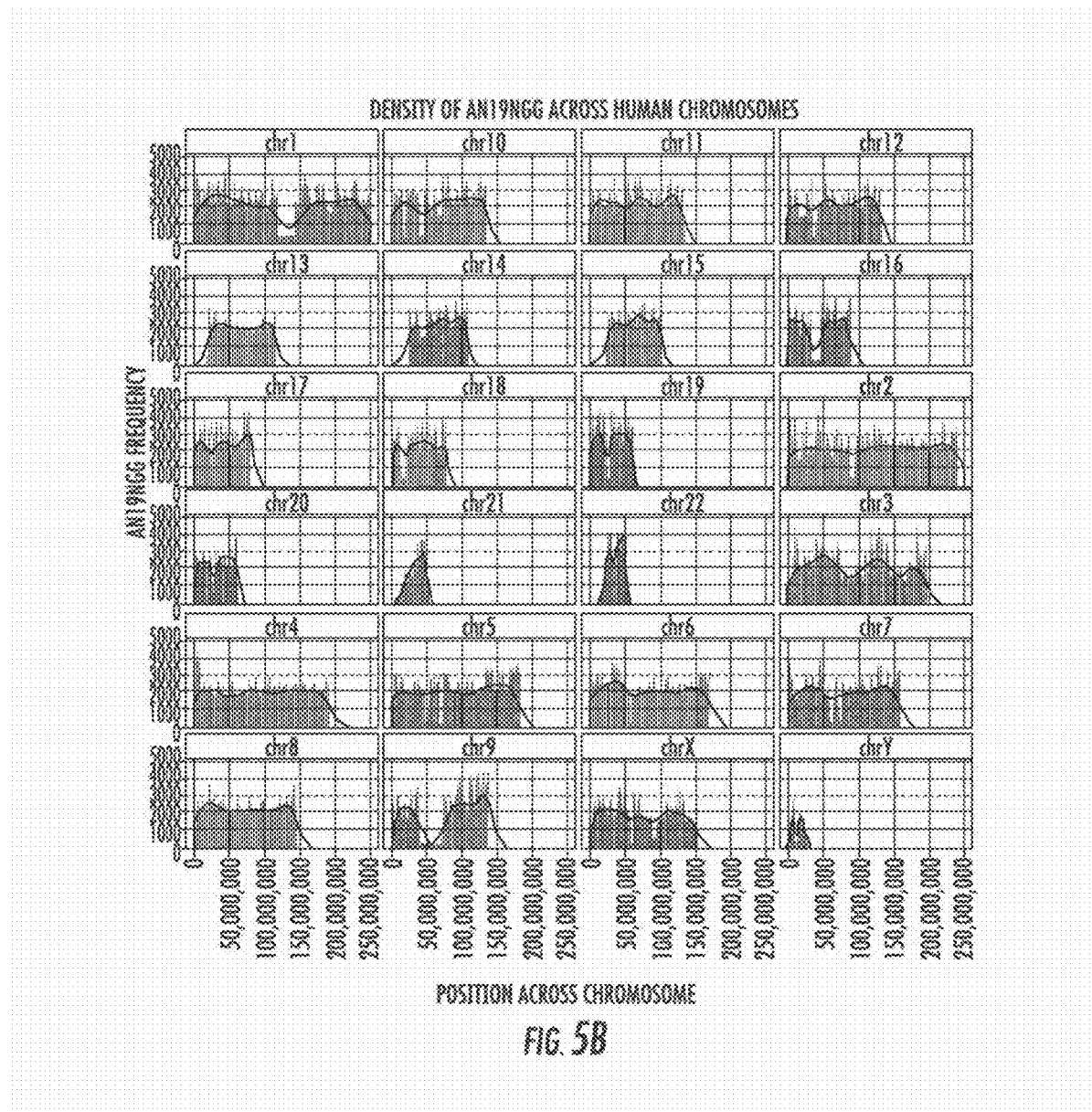
Figure 5C:
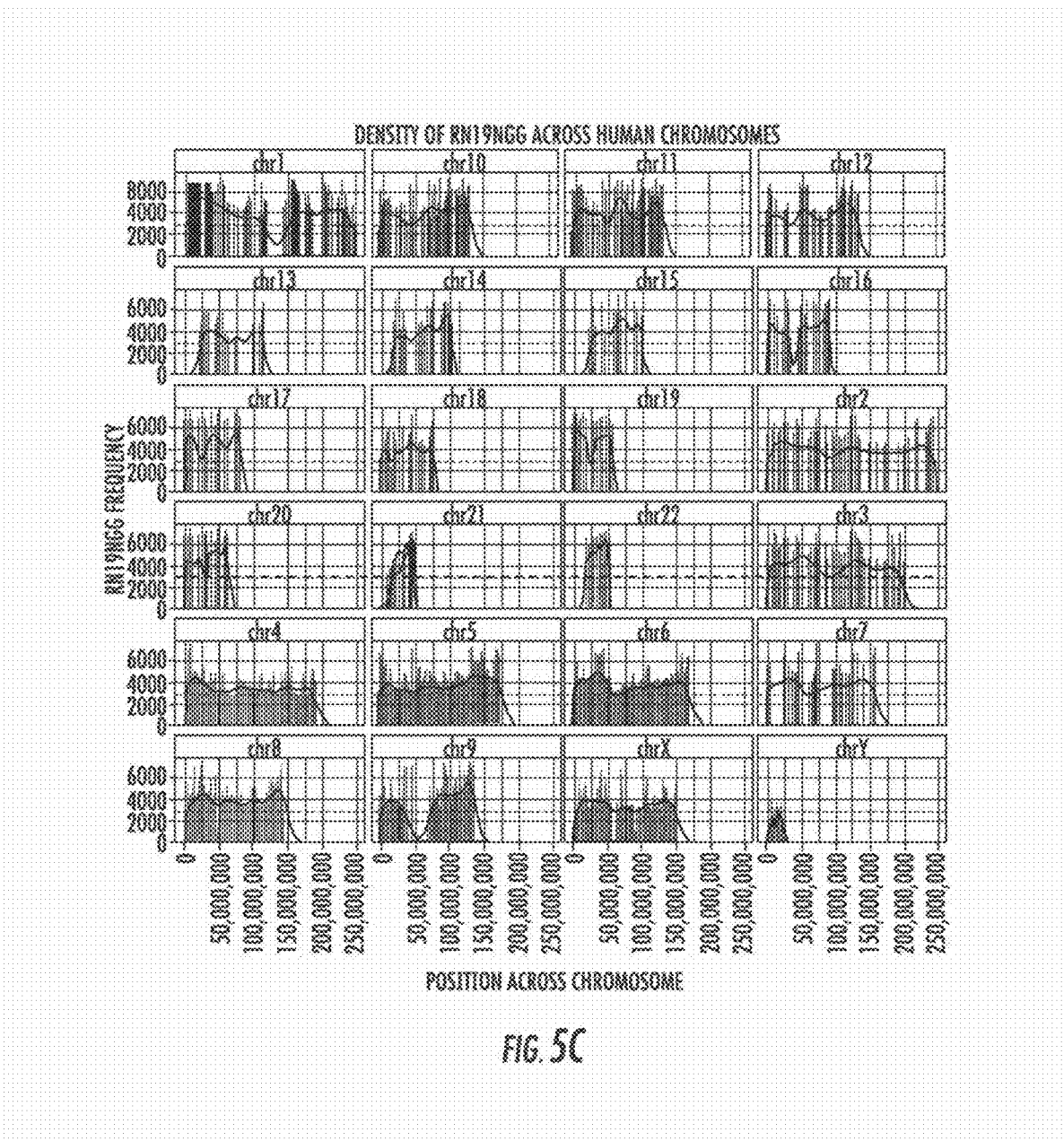

Having thus described the presently disclosed subject matter in general terms, reference will now be made to the accompanying Figures, which are not necessarily drawn to scale, and wherein:

FIG. 1A, FIG. 1B, FIG. 1C, and FIG. 1D show an evaluation of the ability to direct CRISPR targeting via gRNA synthesis from the H1 promoter. A schematic illustration depicting the gRNA expression constructs is shown in FIG. 1A. Above, the U6 promoter only expresses gRNAs with a +1 guanosine nucleotide; below, the H1 promoter can drive expression of gRNAs initiating at either purine (adenosine or guanosine) nucleotide. Below, a cartoon depiction of the Cas9 protein with gRNA targeting genomic sequence $AN_{19}NGG$ is shown (sequence shown is SEQ ID NO: 30). The location of the +1 A is indicated. A schematic overview of the eGFP targeted disruption assay is shown in FIG. 1B. eGFP fluorescence is disrupted by CRISPR targeting followed by error-prone NHEJ-mediated repair resulting in frameshift mutations that disrupt the coding sequence, resulting in loss of fluorescence. FIG. 1C shows microscope images demonstrating successful CRISPR targeting by U6 or H1 promoter expressed gRNAs. H7 ES cells were stained and colonies were visualized to show nuclei (left, magenta), eGFP fluorescence (middle, green), and merged images (right) indicating areas of GFP fluorescence mosaicism in the colony. To the right is shown the quantification of eGFP fluorescence loss by flow cytometry for the respective constructs. Below is a higher magnification of an H7 colony targeted by an H1 expressed gRNA showing expression mosaicism. Scale bar, 50 µM. Surveyor assay-based quantitation of the frequency of NHEJ is shown in FIG. 1D. Bioanalyzer gel image depicting control (first lane), U6 expressed gRNA (second lane), H1 expressed gRNA (third lane), and marker (fourth lane). The % indel (as calculated by the fraction of uncut (u) to cut (c) bands) is indicated below;

FIG. 2 shows Surveyor analysis and quantification of NHEJ in HEK-293 cells. Shown above is an eGFP schematic with arrows indicating the targeting sites. Target sites on the plus strand are indicated pointing to the right, and minus strand targets are indicated pointing to the left; blue arrows indicate H1 promoter gRNAs and orange arrows indicate U6 promoter gRNAs. Shown below is the Bioanalyzer gel from the Surveyor assay. The target site coordinates are listed above and the calculated % indel is indicated below;

FIG. 3A, FIG. 3B, and FIG. 3C show targeting and homologous recombination at the AAVS1 locus. Surveyor analysis of three gRNAs expressed by the H1 promoter (AAVS1-1a through -1-3a), three gRNAs expressed by the U6 promoter (AAVS-1-1 through -1-3), and a control non-targeting gRNA are shown in FIG. 3A. FIG. 3B shows a schematic of AAVS-1 targeting donor vector (shown above the AAVS1 Locus (labeled "AAVS1")) and cell imaging of an GFP-positive H7 ES cell colony following electroporation with H1::AAVS1-3a gRNA and the AAVS-1 targeting vector. Sanger sequencing of the targeting junction region indicating correct integration by homologous recombination is shown in FIG. 3C (sequence shown is SEQ ID NO:31);

FIG. 4A, FIG. 4B, FIG. 4C, and FIG. 4D show bioinformatics analysis of $GN_{19}NGG$ and $AN_{19}NGG$ sites in the genome. A Circos plot depicting the frequency of CRIPSR sites in the human genome is shown in FIG. 4A. The outside circle depicts the human chromosome ideograms. Moving inwards, $GN_{19}NGG$ (orange), $AN_{19}NGG$ (blue), and $RN_{19}NGG$ (purple) CRISPR sites frequency is indicated along the chromosomes. Plotted inside the circle is the human exon density (black), and OMIM disease loci (blue). The frequency and distance between CRISPR sites in the genome is shown in FIG. 4B. Barplot of the frequency and distance of adjacent $GN_{19}NGG$ (orange), $AN_{19}NGG$ (blue) sites in the genome is shown. The mean and median values are inset within the plot including $RN_{19}NGG$ sites. FIG. 4C shows barplot quantification of $GN_{19}NGG$ vs $AN_{19}NGG$ site frequency at human genes (left) or OMIM disease loci (right). FIG. 4D shows a barplot quantifying the $GN_{19}NGG$ vs. $AN_{19}NGG$ frequency in six genomes: human, cow, mouse, rat, chicken, and zebrafish;

FIG. 5A, FIG. 5B, FIG. 5C, FIG. 5D, FIG. 5E, and FIG. 5F show bioinformatic analysis of $GN_{19}NGG$ and $AN_{19}NGG$ sites in the genome. Three panels depicting the density of each gRNA sites in the human genome are shown: $GN_{19}NGG$ (FIG. 5A), $AN_{19}NGG$ (FIG. 5B), and $RN_{19}NGG$ (FIG. 5C). Within each plot, the density of CRISPR sites is plotted along each chromosome. Overlaid in semi-transparent (orange, blue, or purple) is the density curve calculated as a smooth Gaussian kernel. The dotted line indicates 35 bp; as a reference, on average, TALEN targeting sites are estimated to occur every 35 base pairs and ZFN sites occur every couple hundred base pairs (Sander et al. (2011) *Nature Methods* 8:67-69; Cermak et al. (2011) *Nucleic Acids Res.*

Figure 5D:
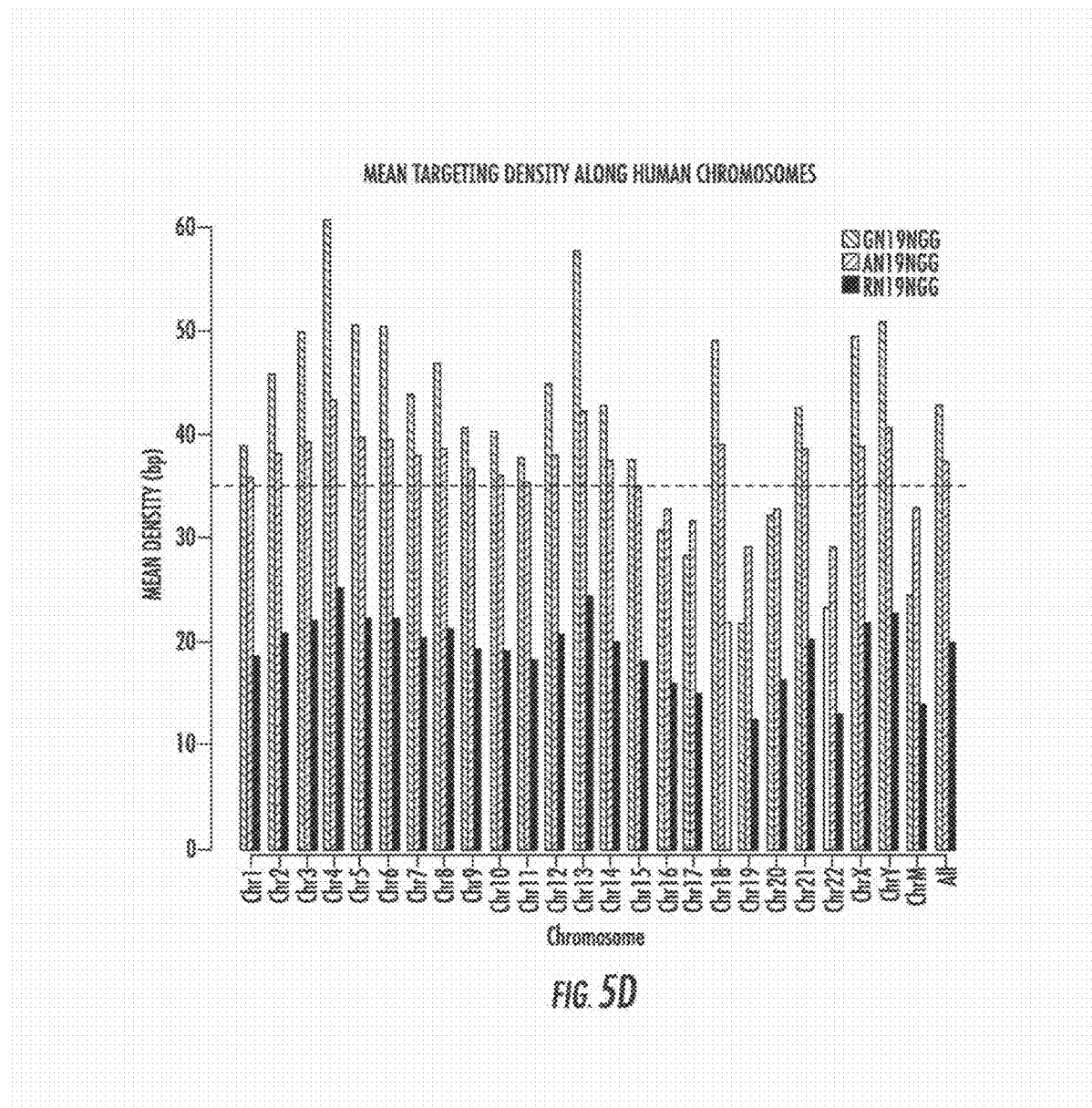
Figure 5E:
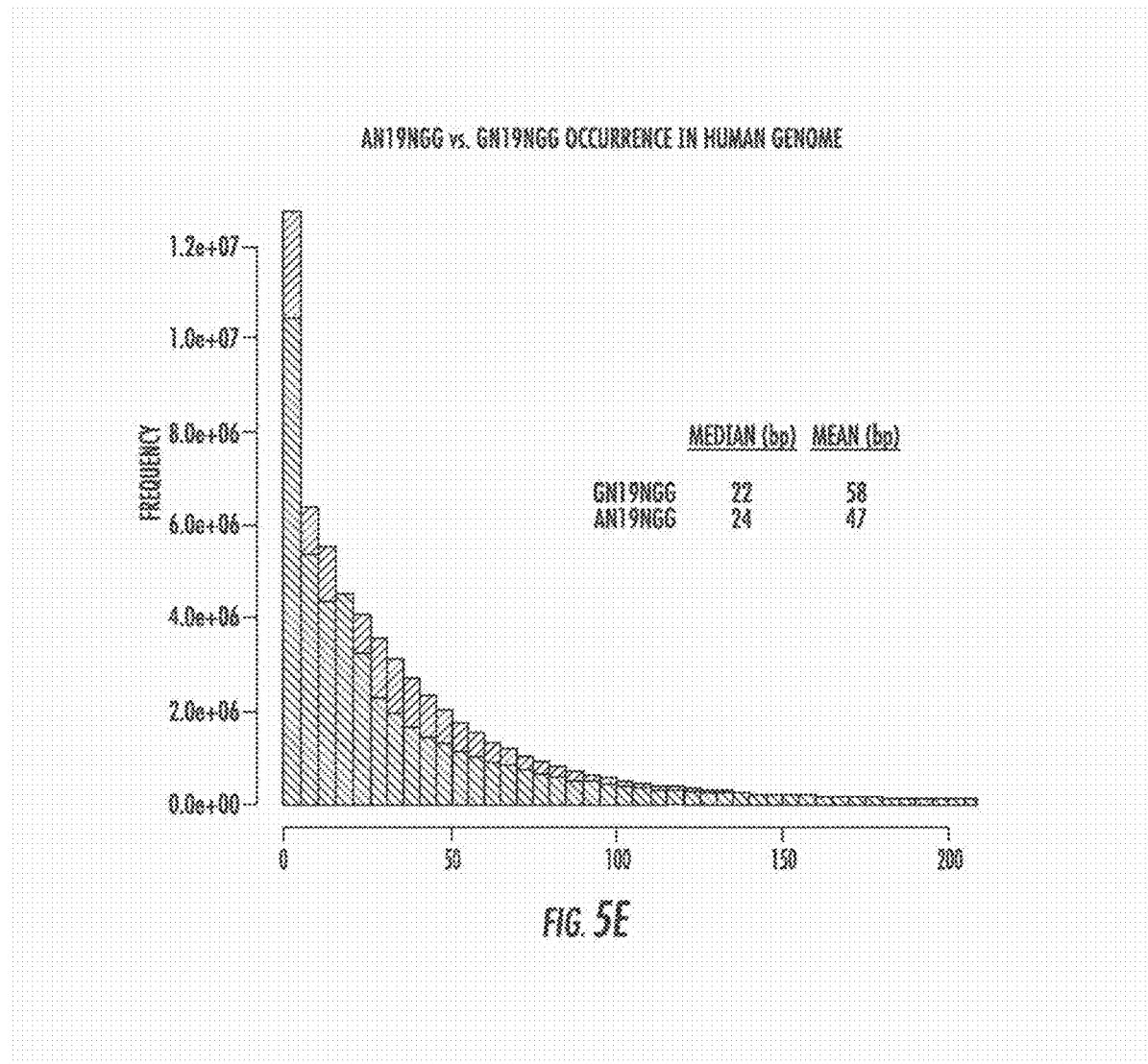
Figure 5F:
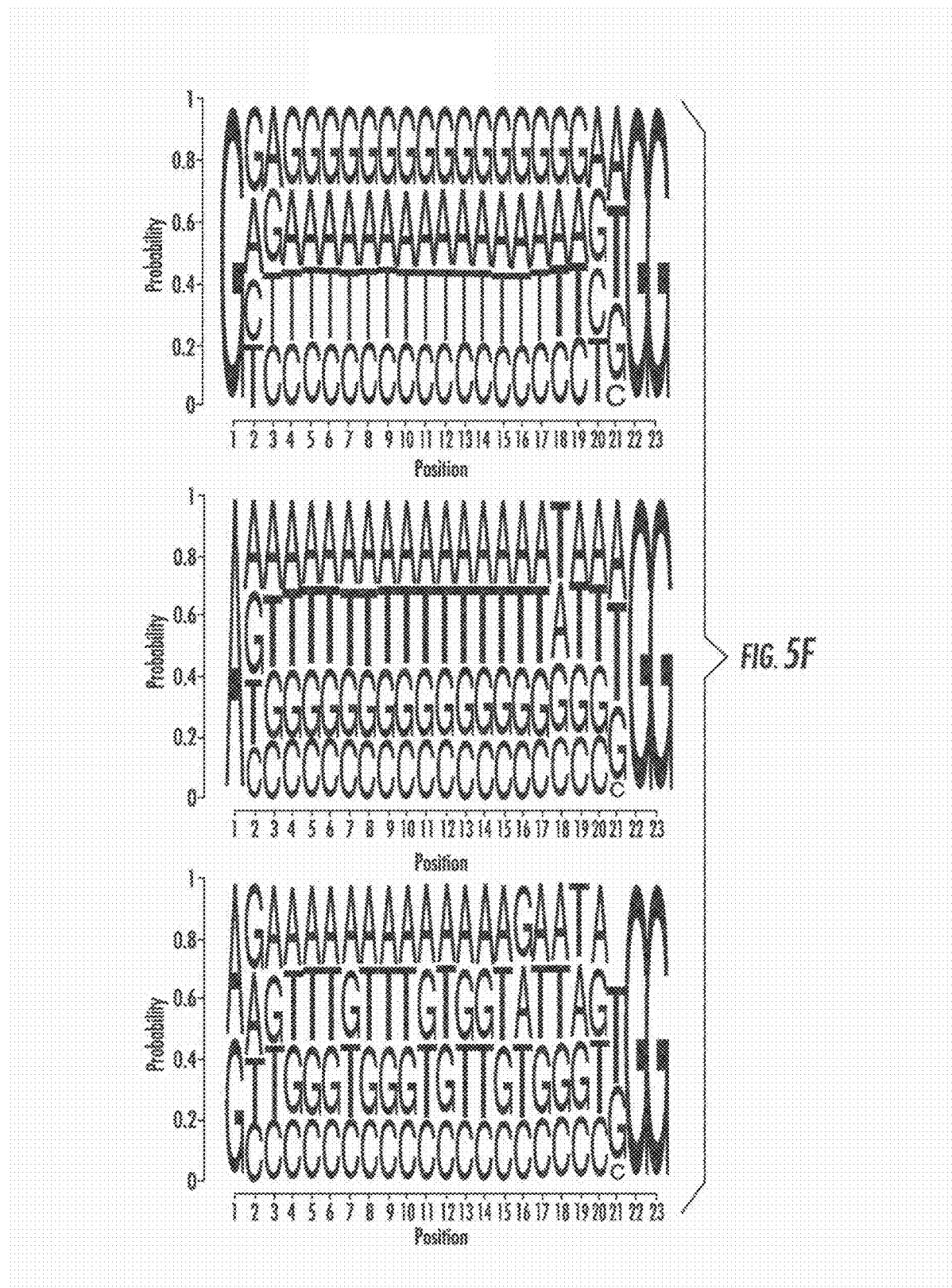
Figure 6A:
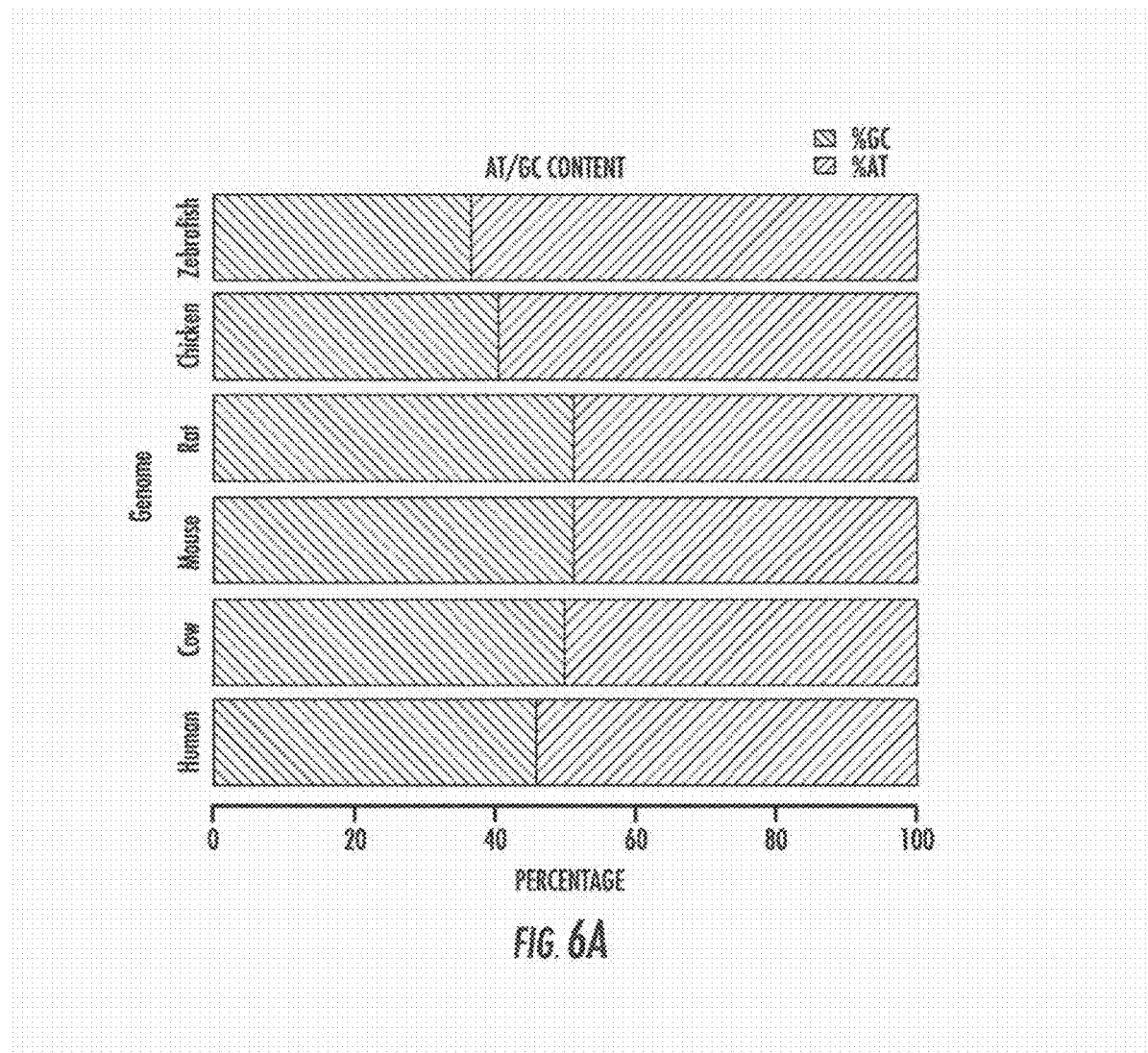
Figure 6B:
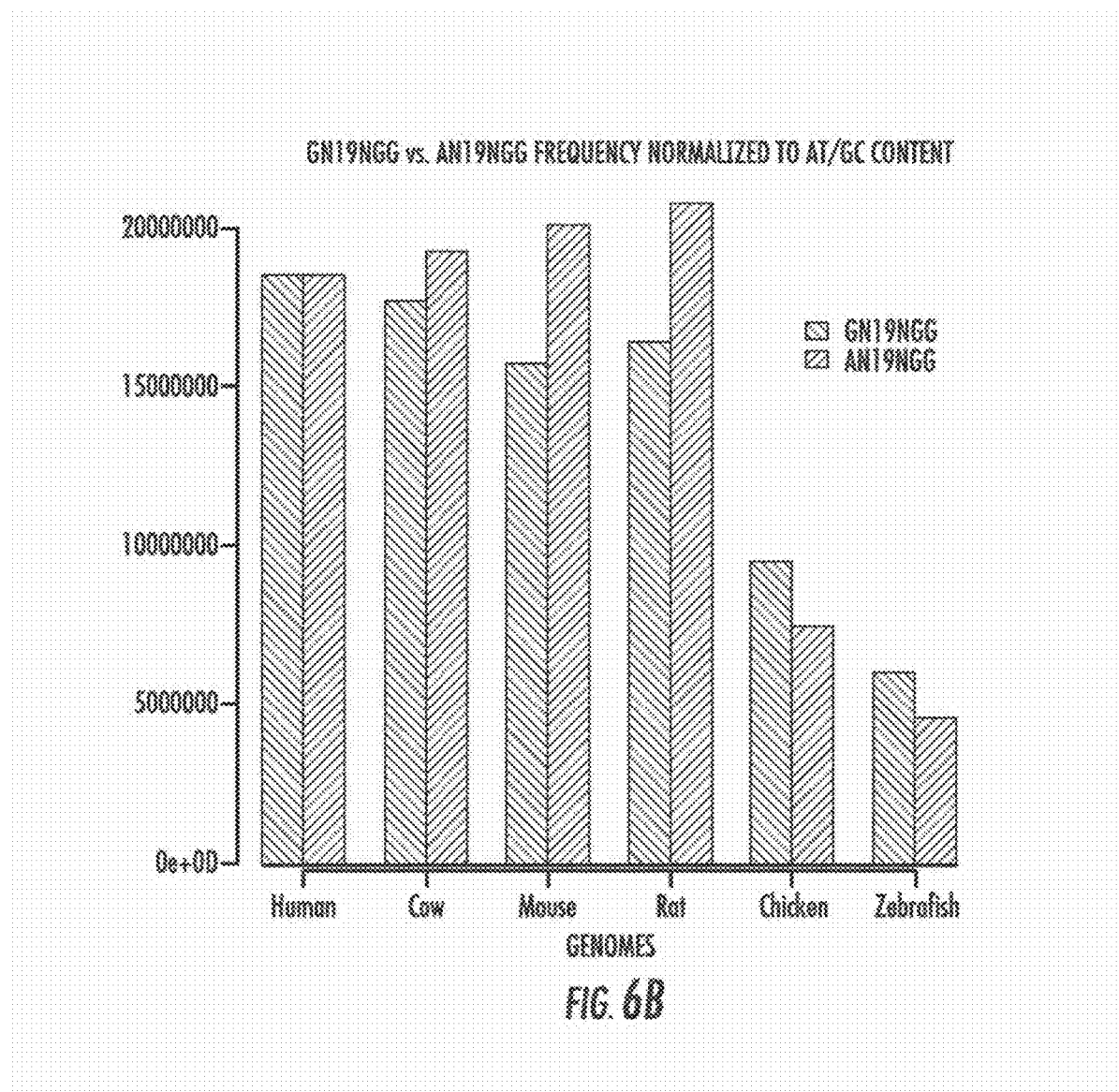
Figure 6C:
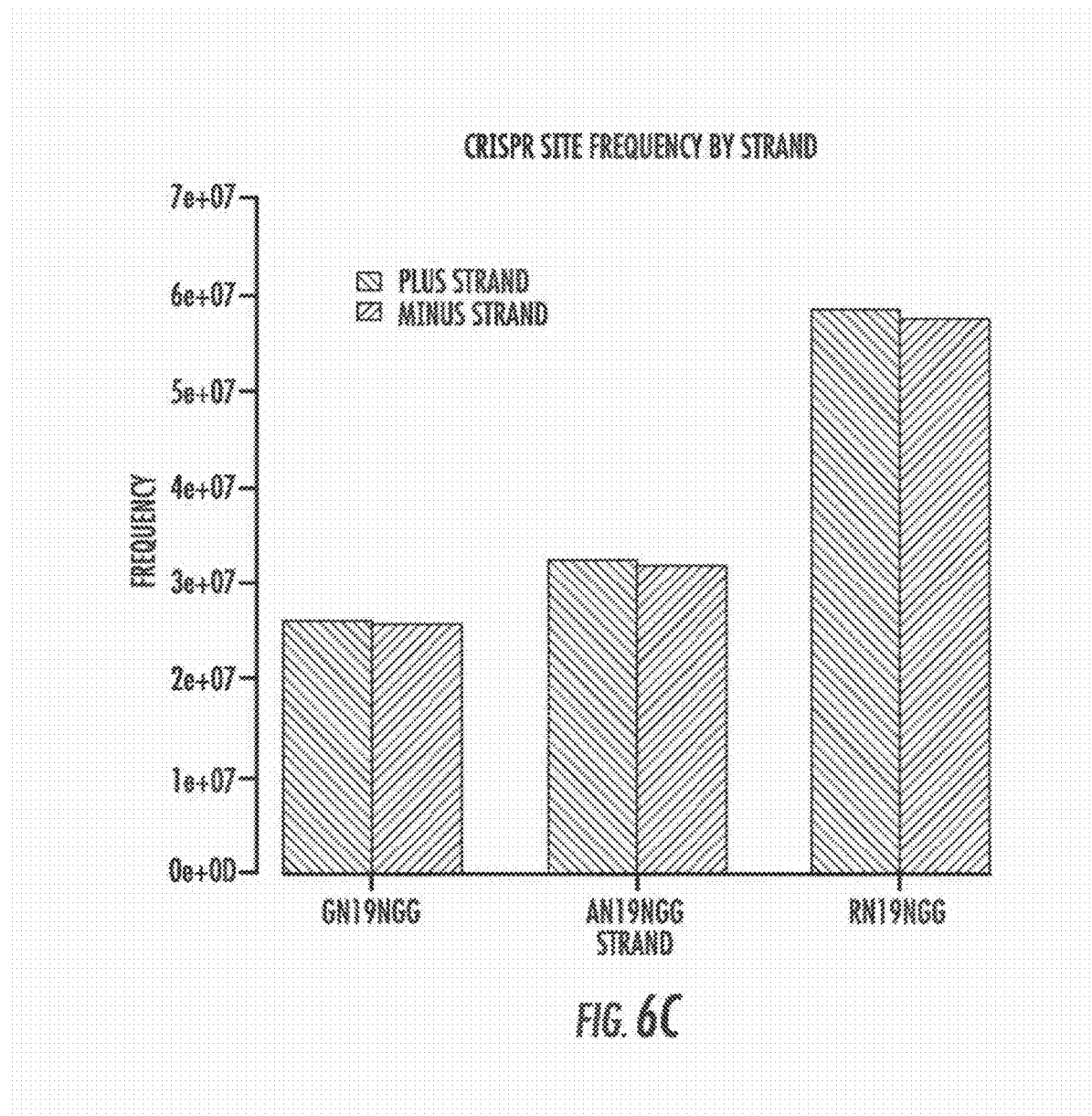
Figure 6D:
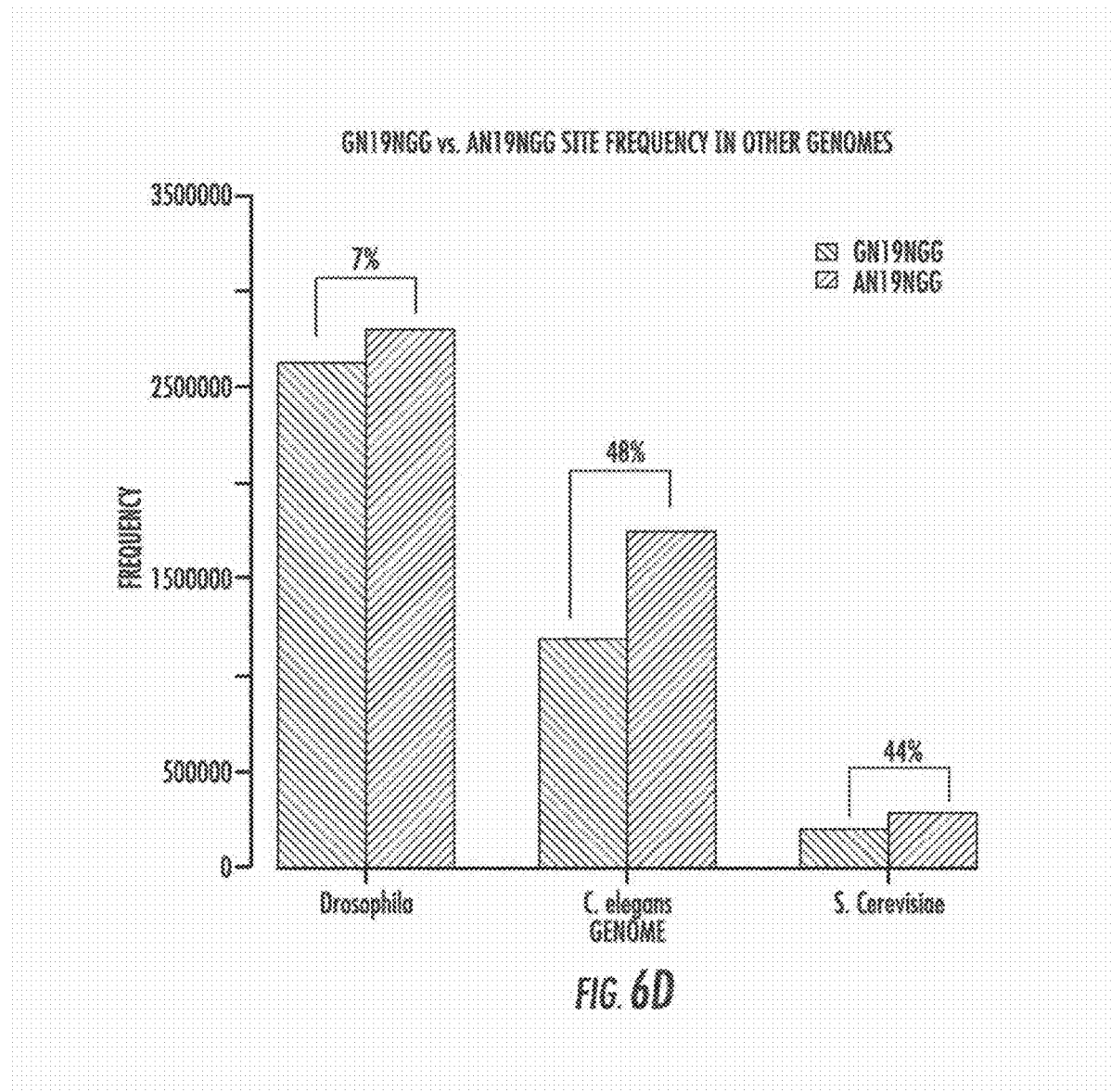
Figure 6E:
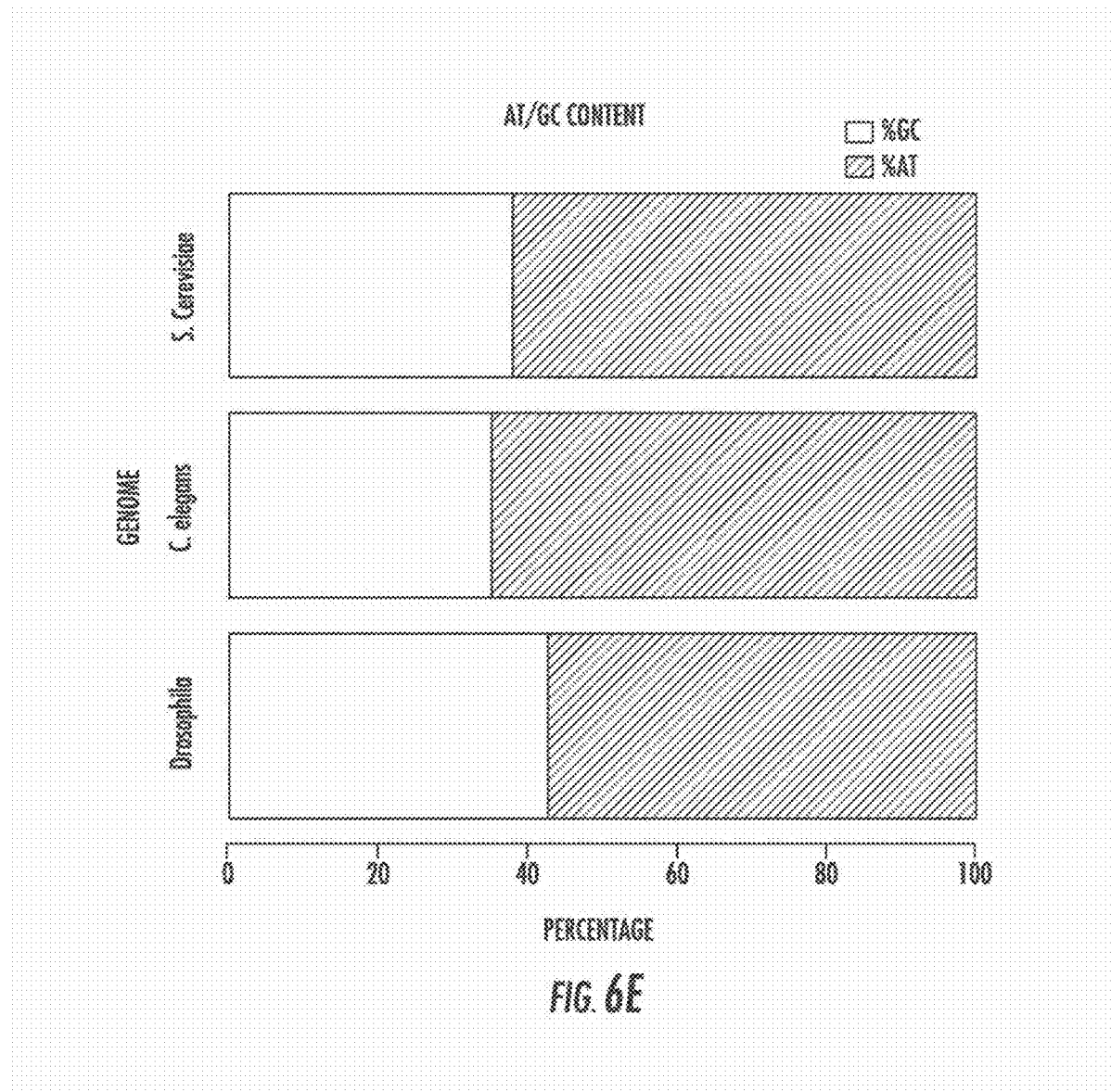
Figure 6F:
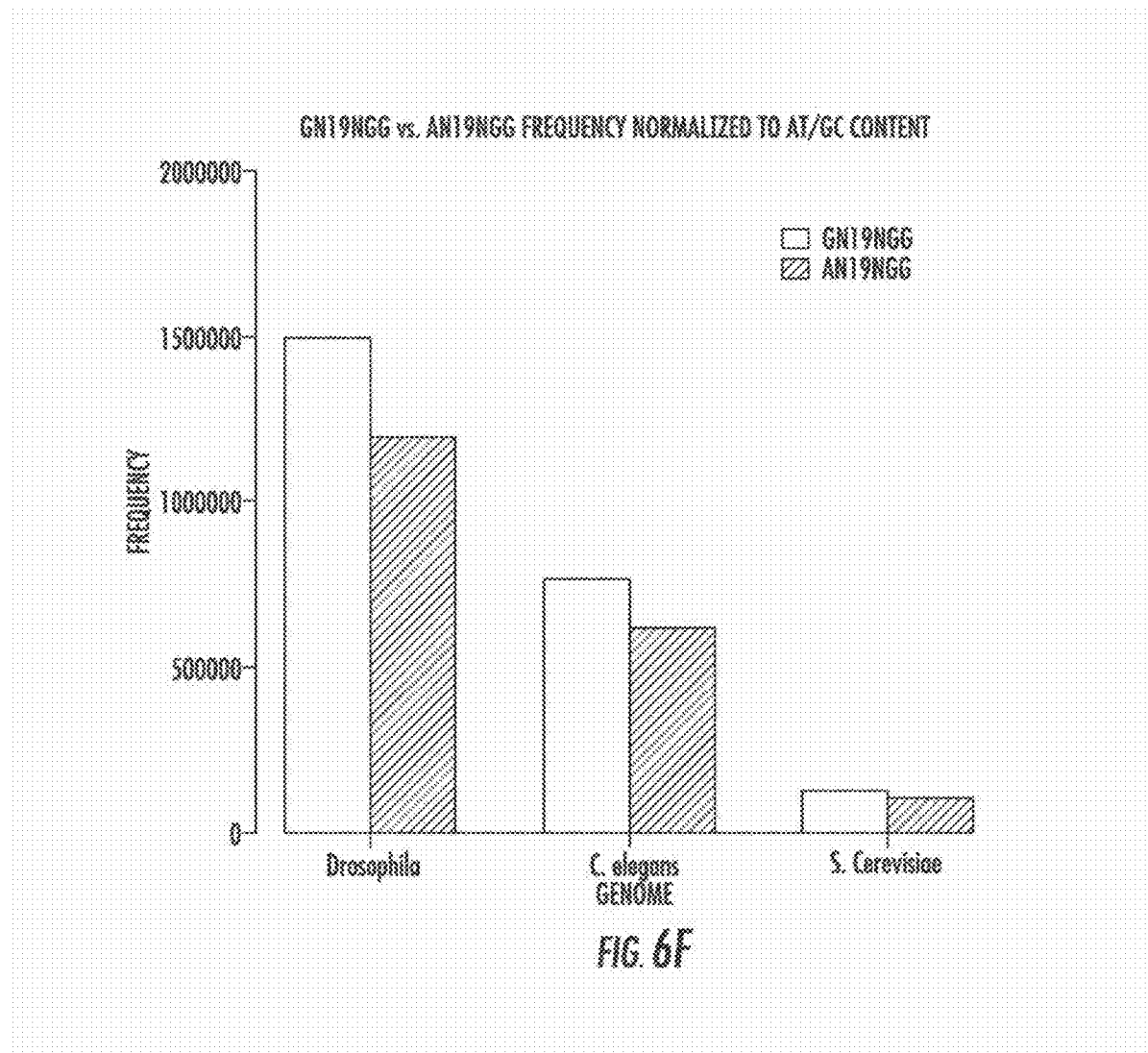
Figure 8A:
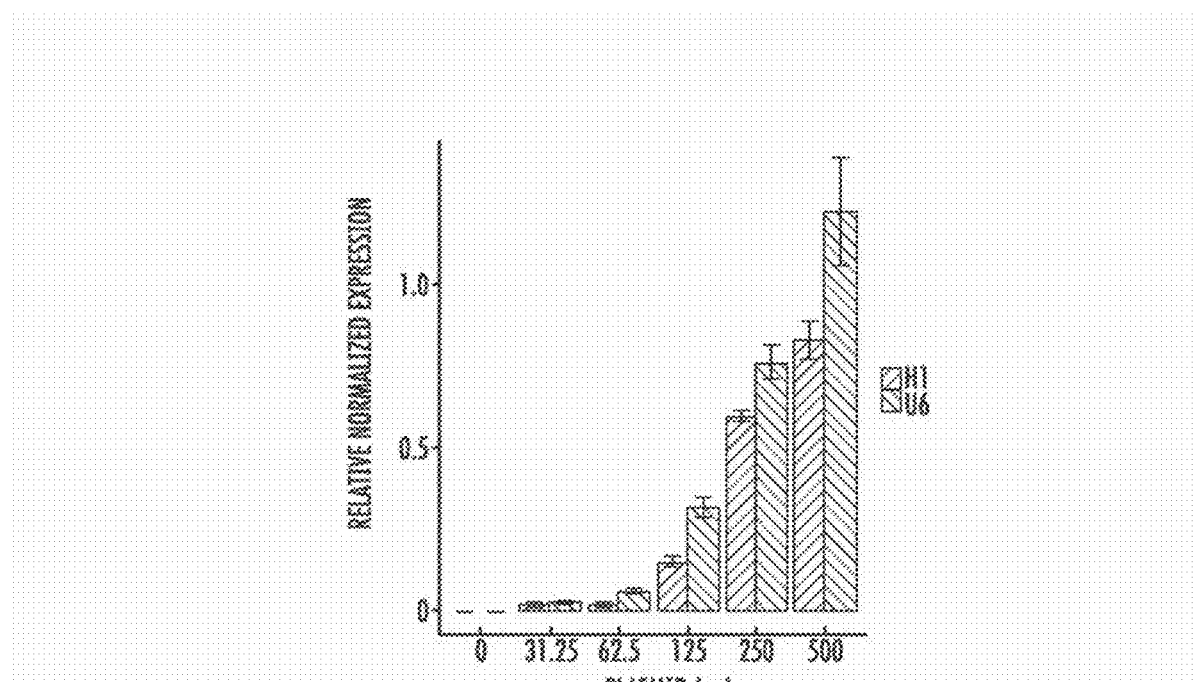
Figure 8B:
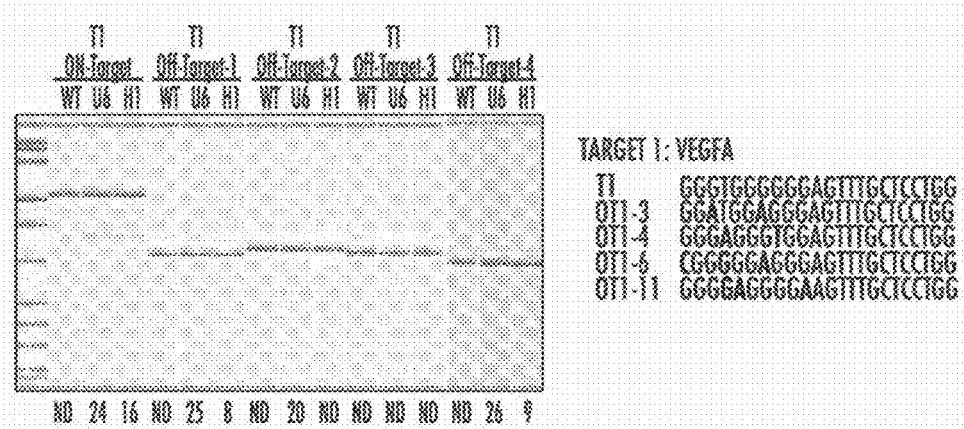
Figure 8C:
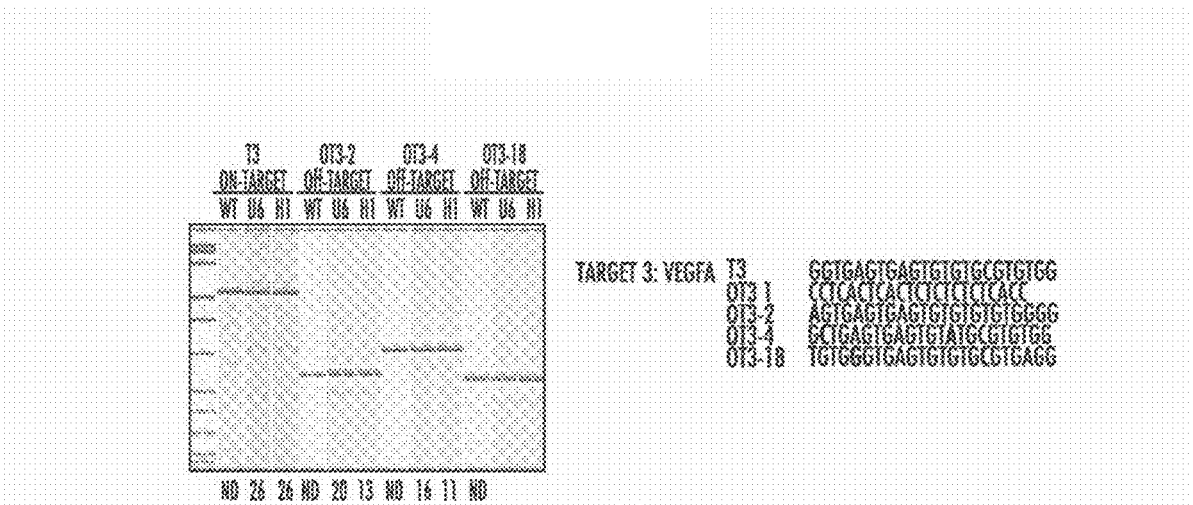
Figure 8D:
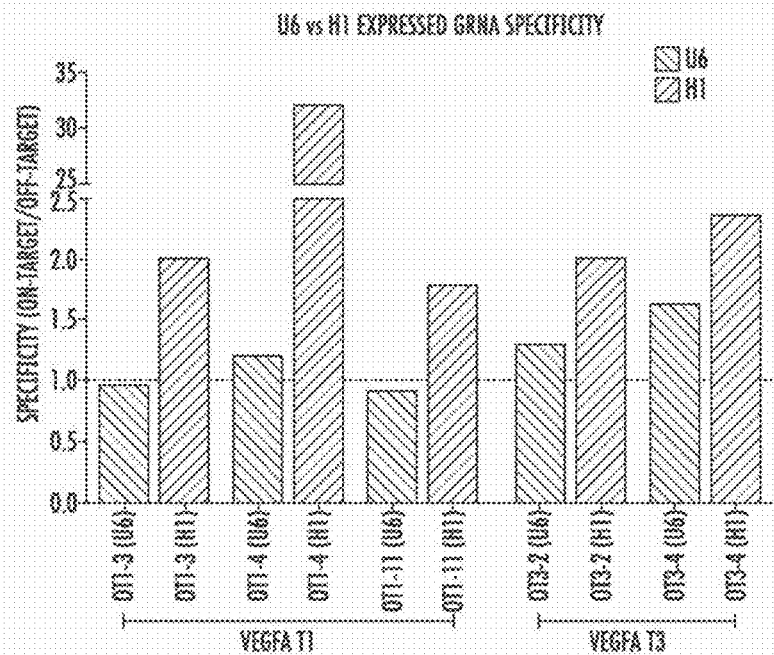
Figure 9A:
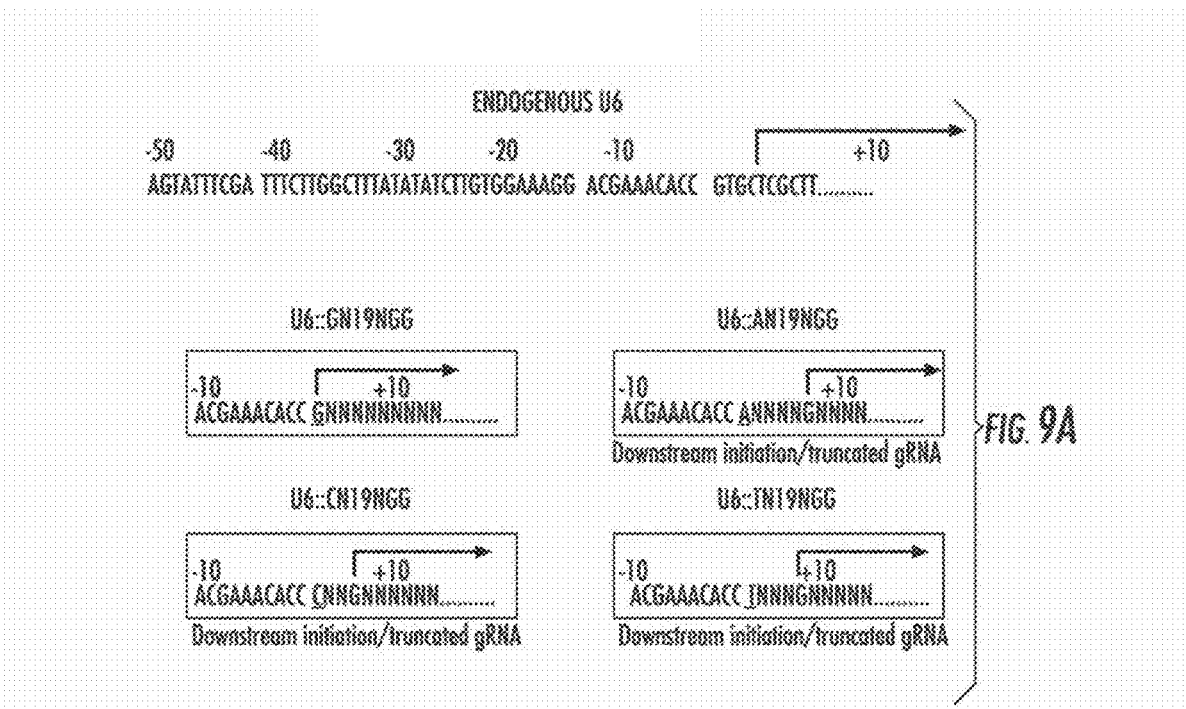
Figure 9B:
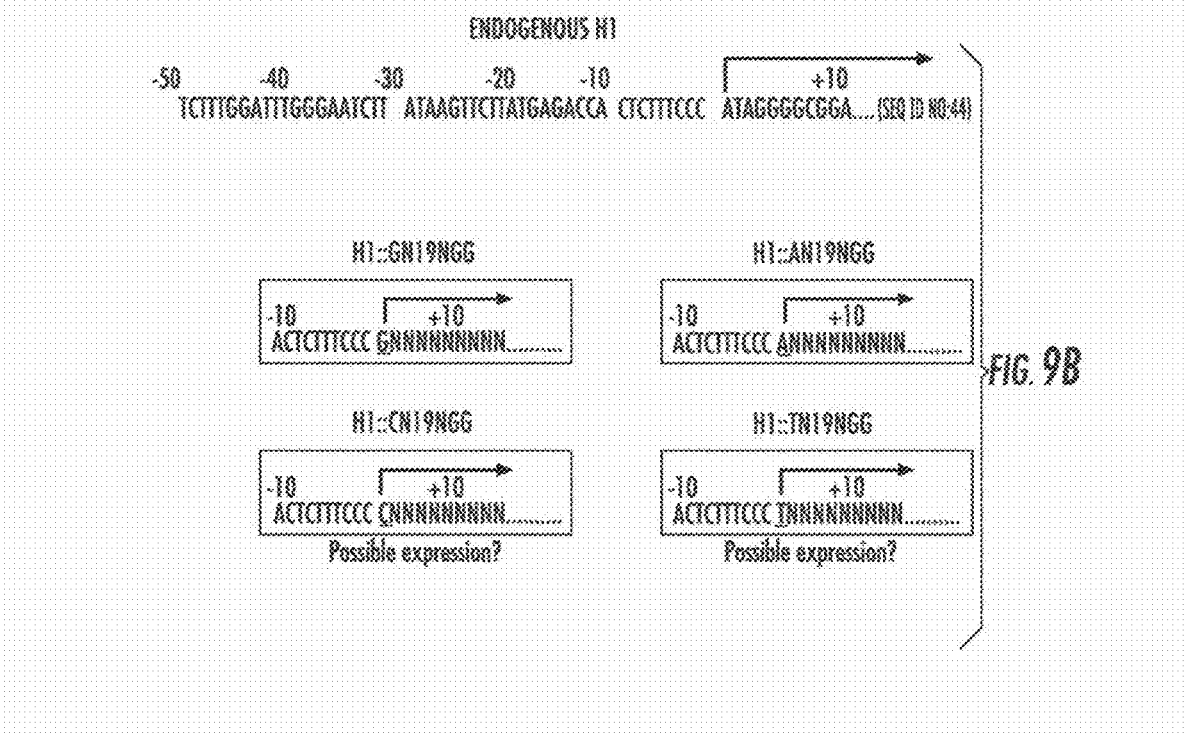
Figure 10E:
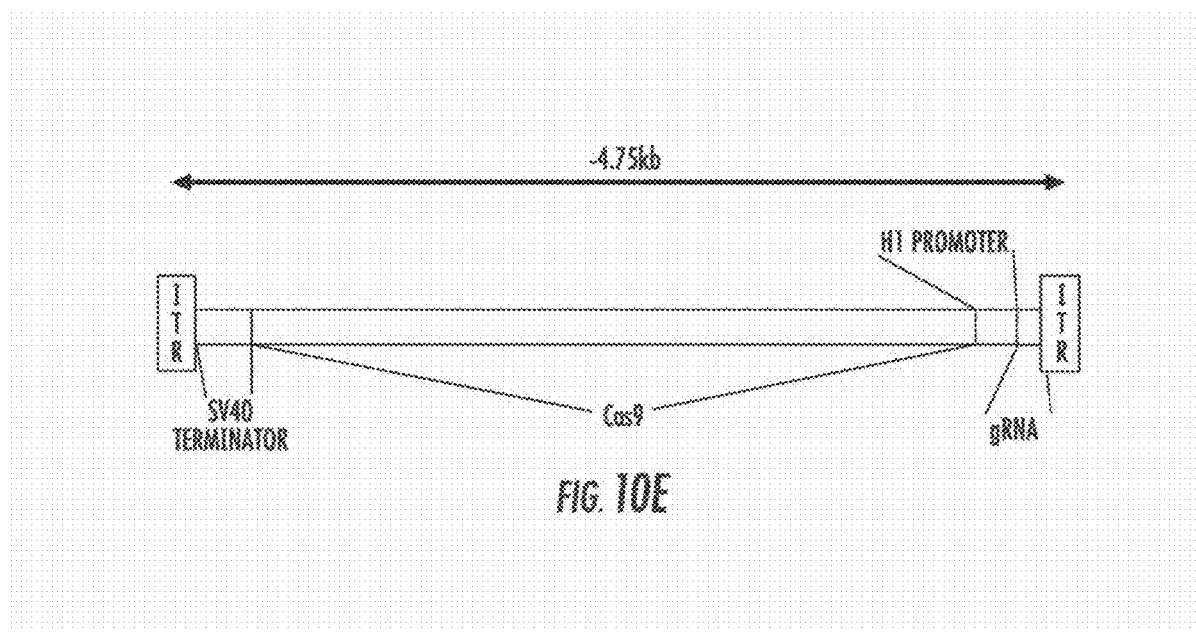
Figure 11A:
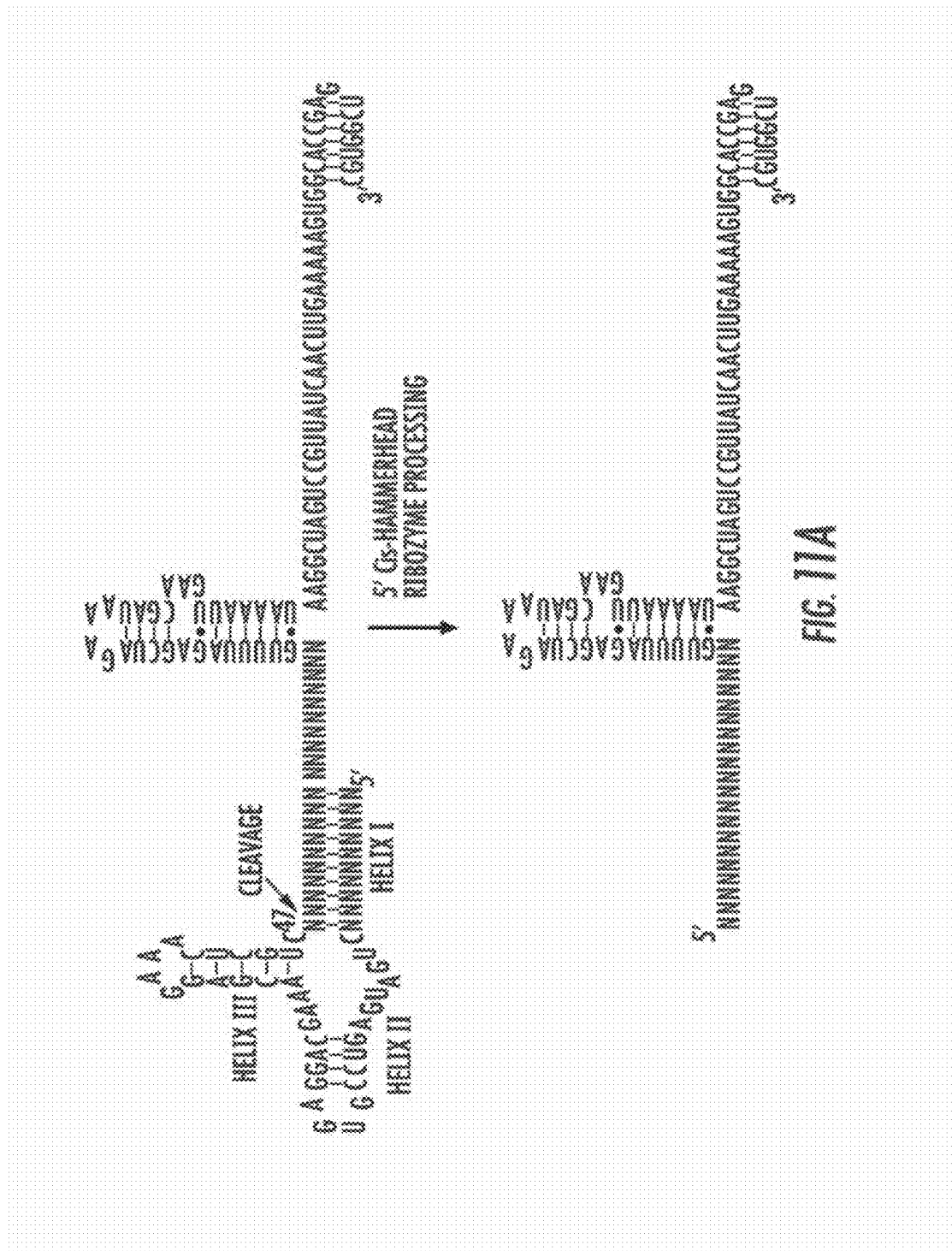
Figure 11B:
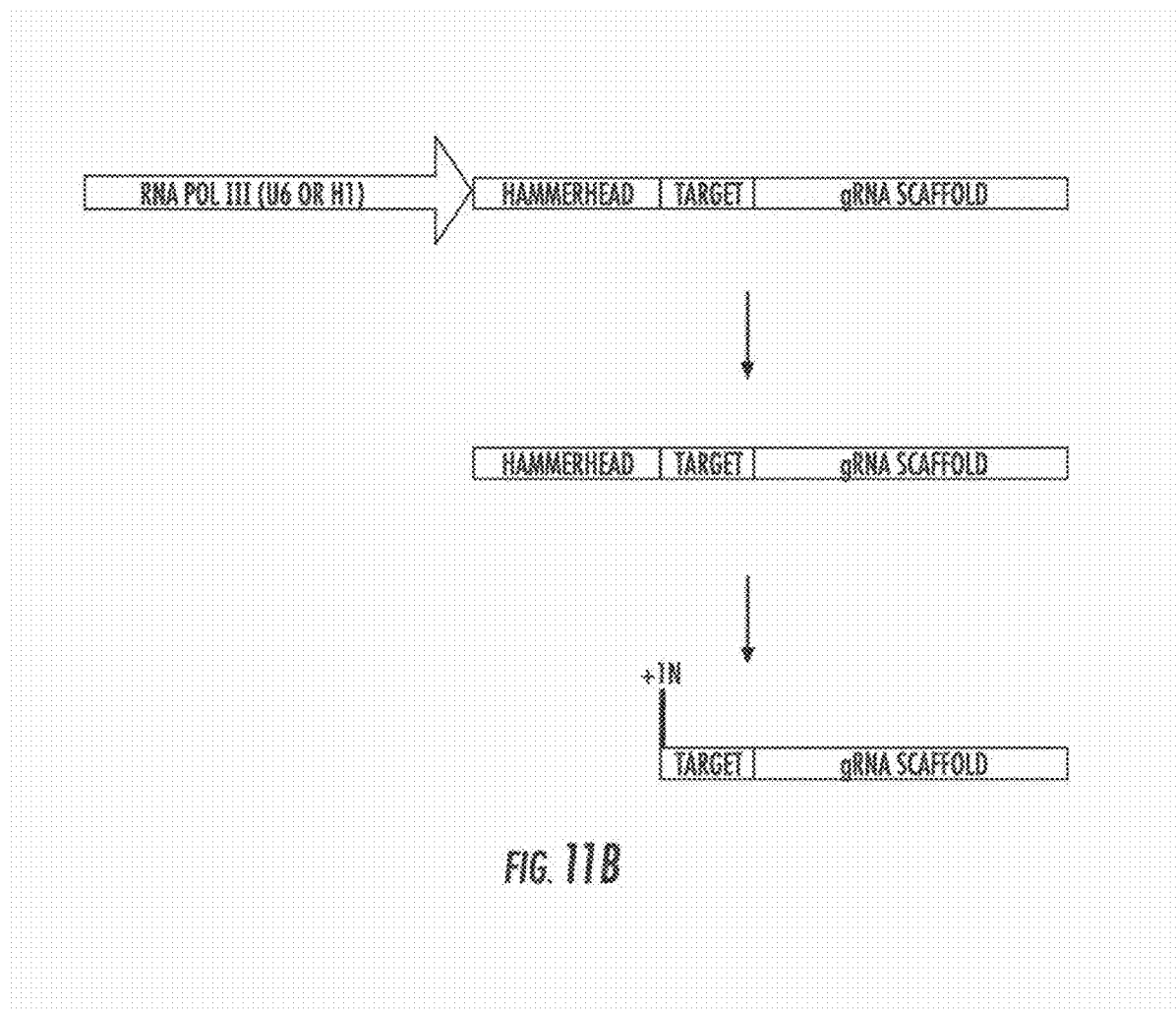
Figure 11C:
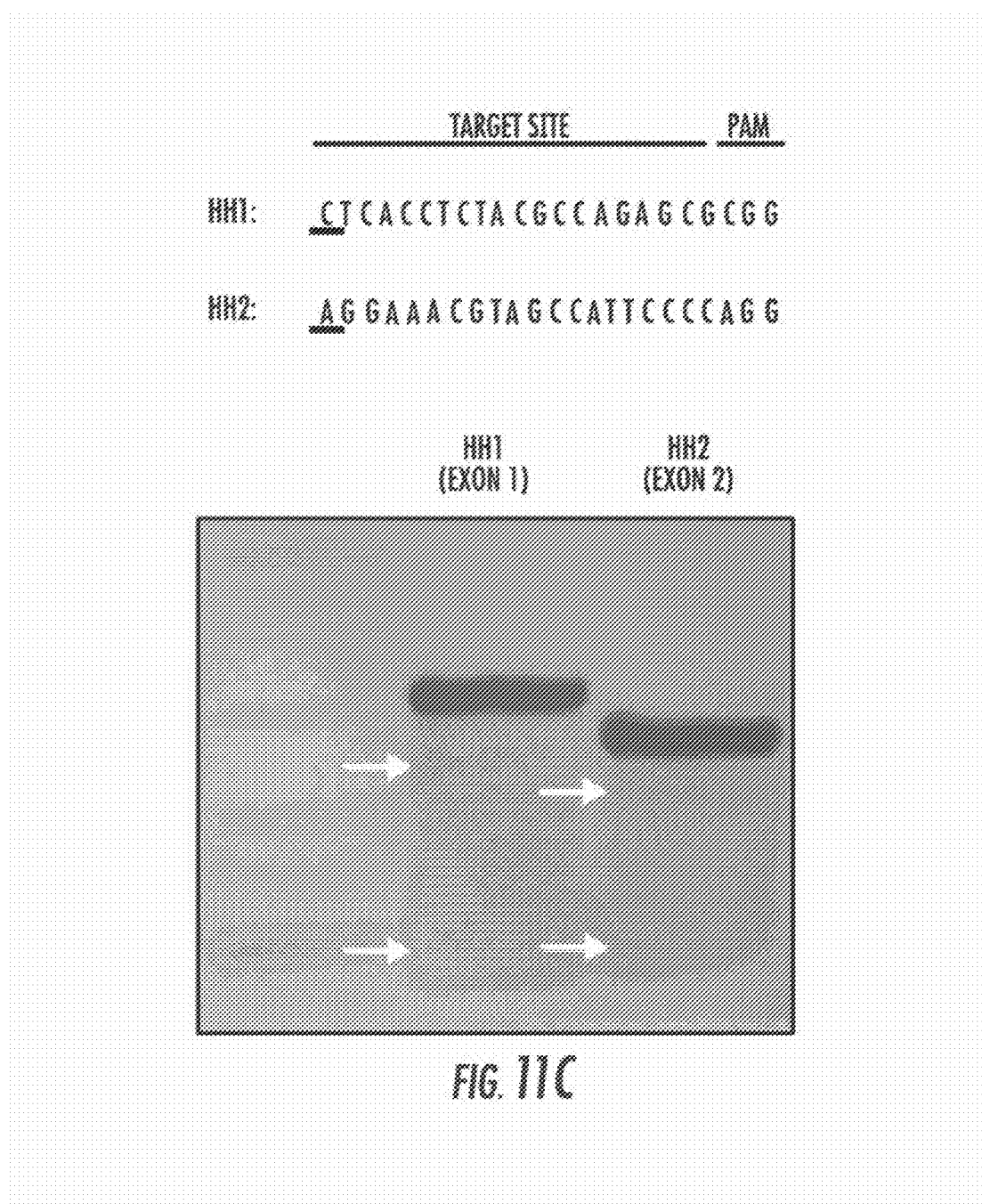
Figure 12:
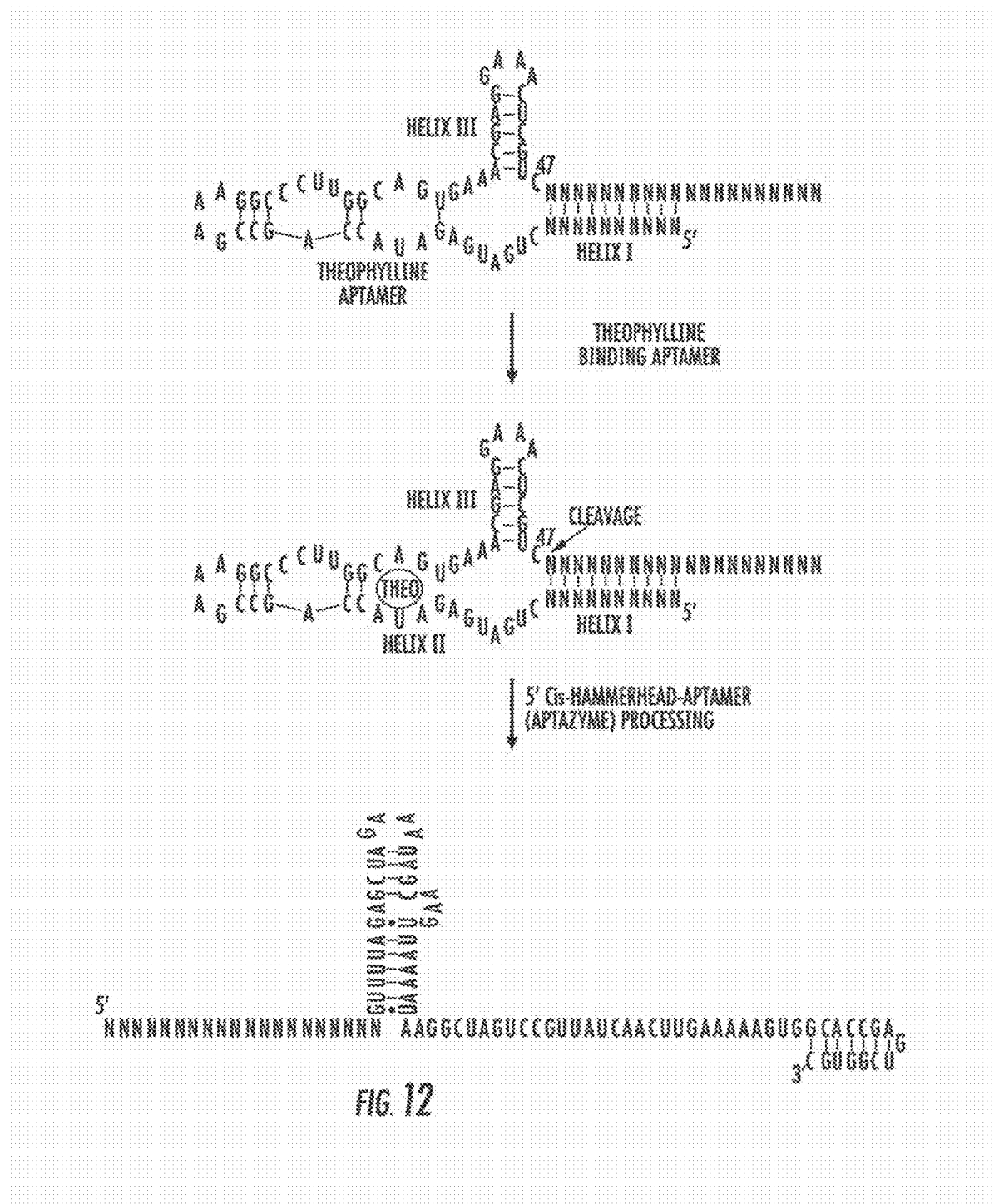
Figure 13:
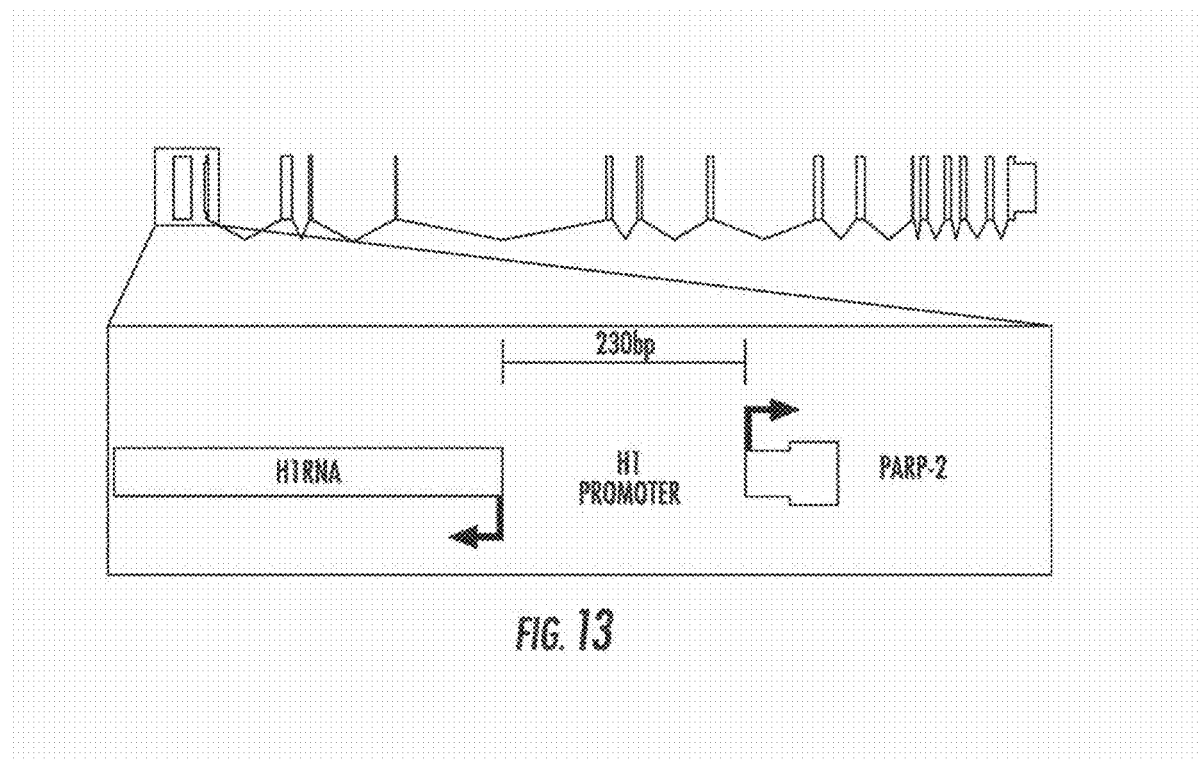
Figure 14:
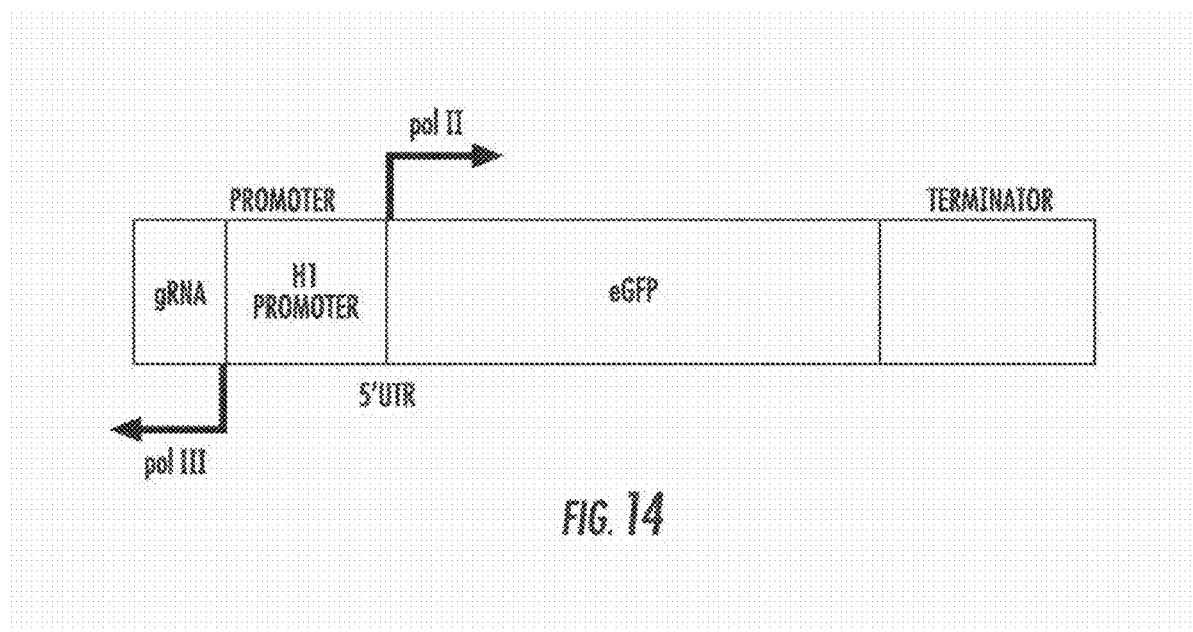
Figure 15:
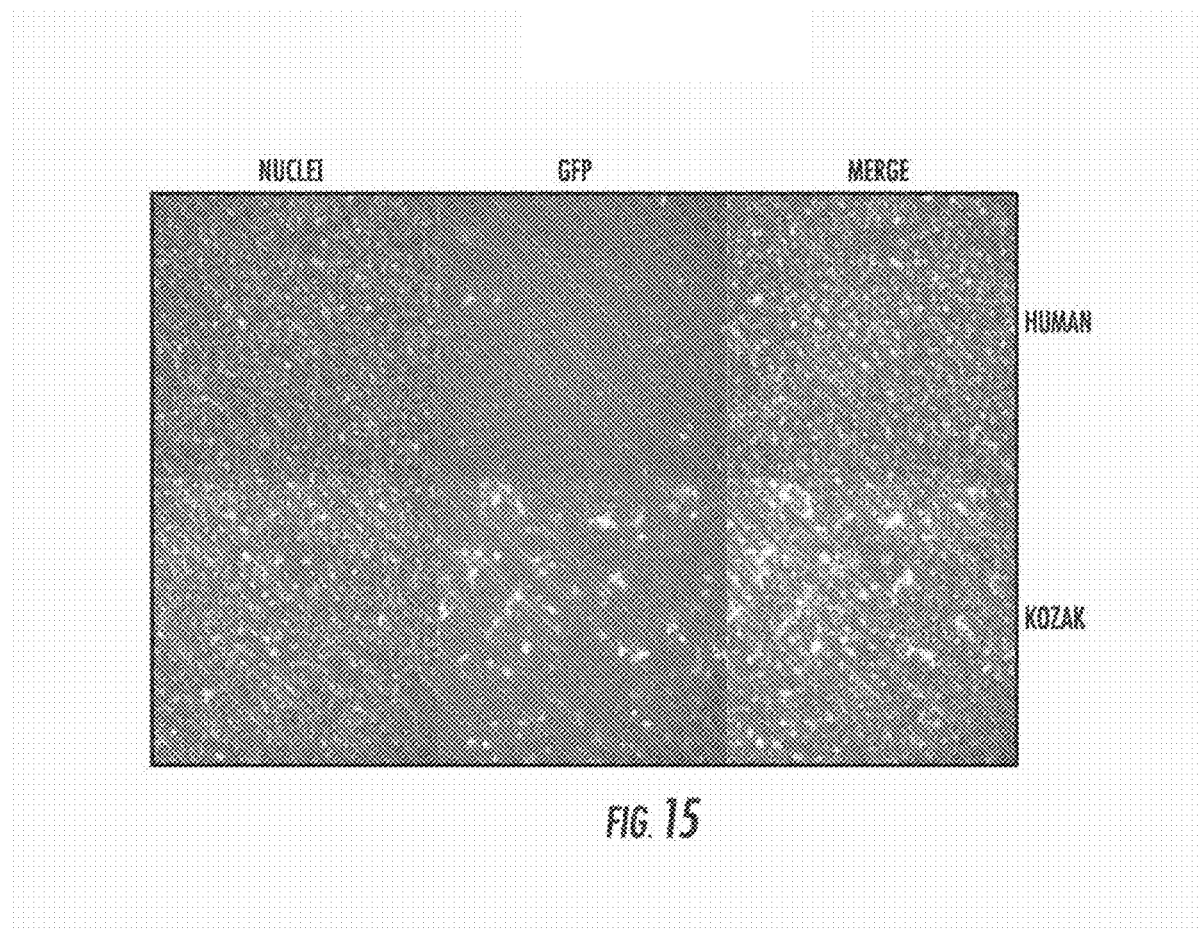
Figures 16A, 16B:
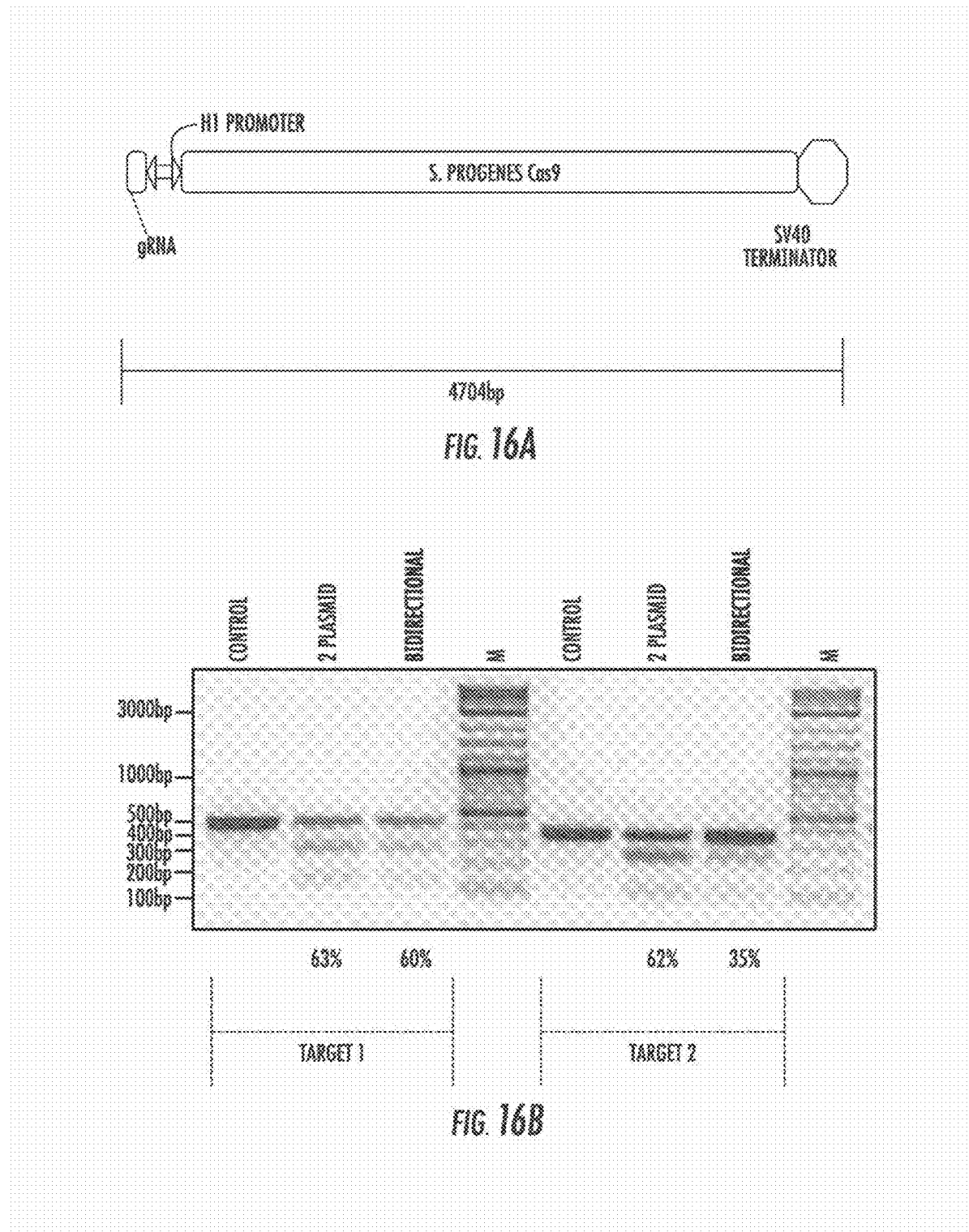
Figure 17:
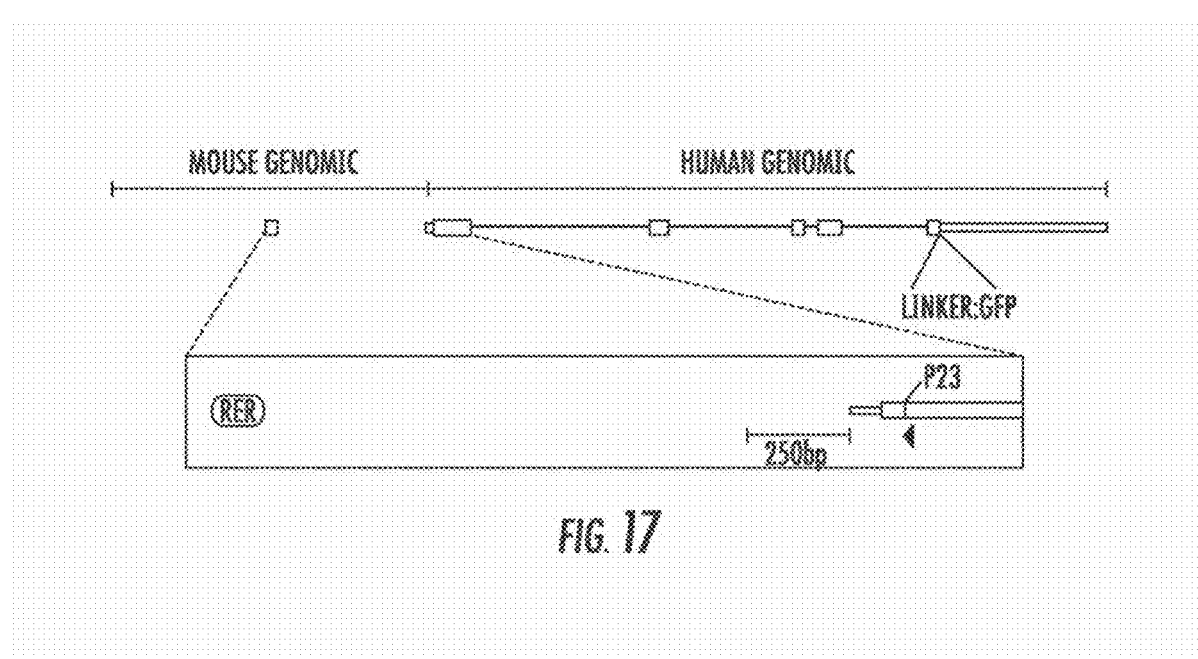
Figure 18A:
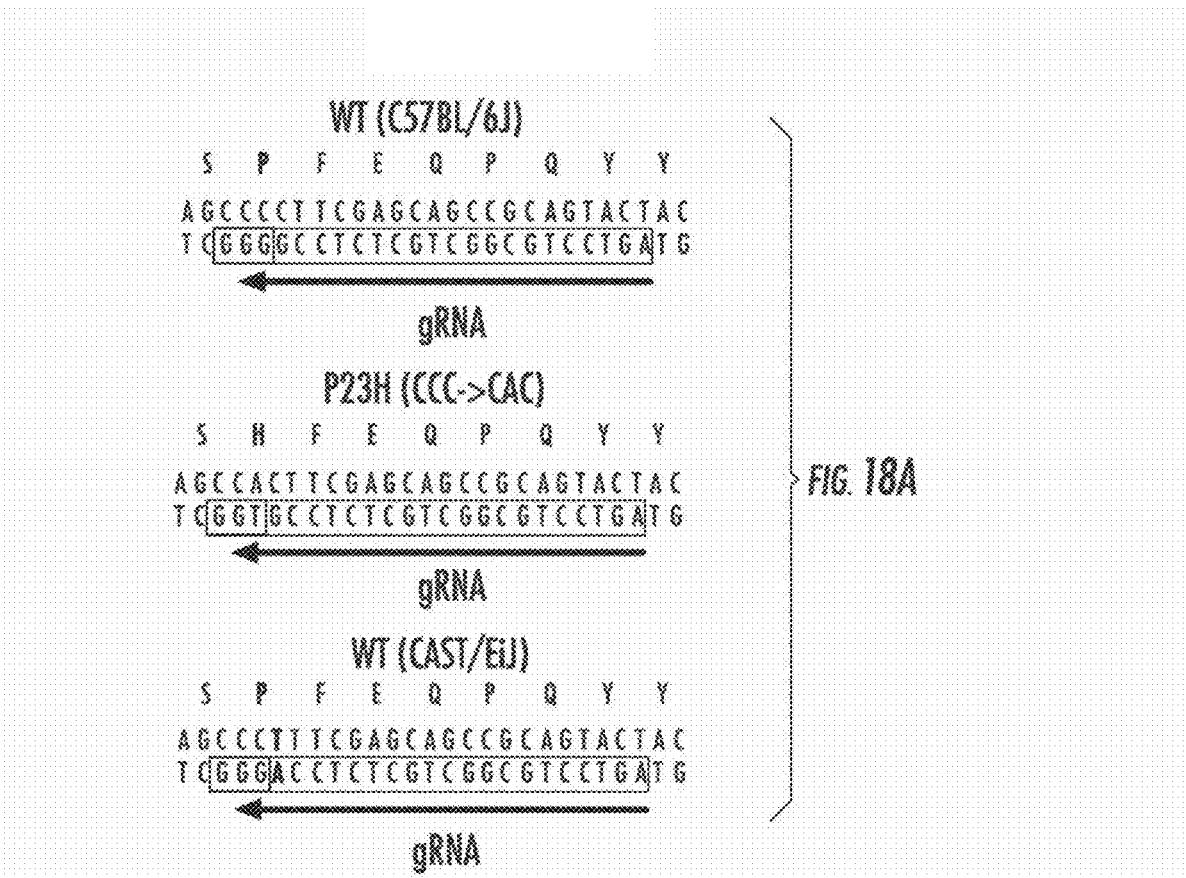
Figure 18B:
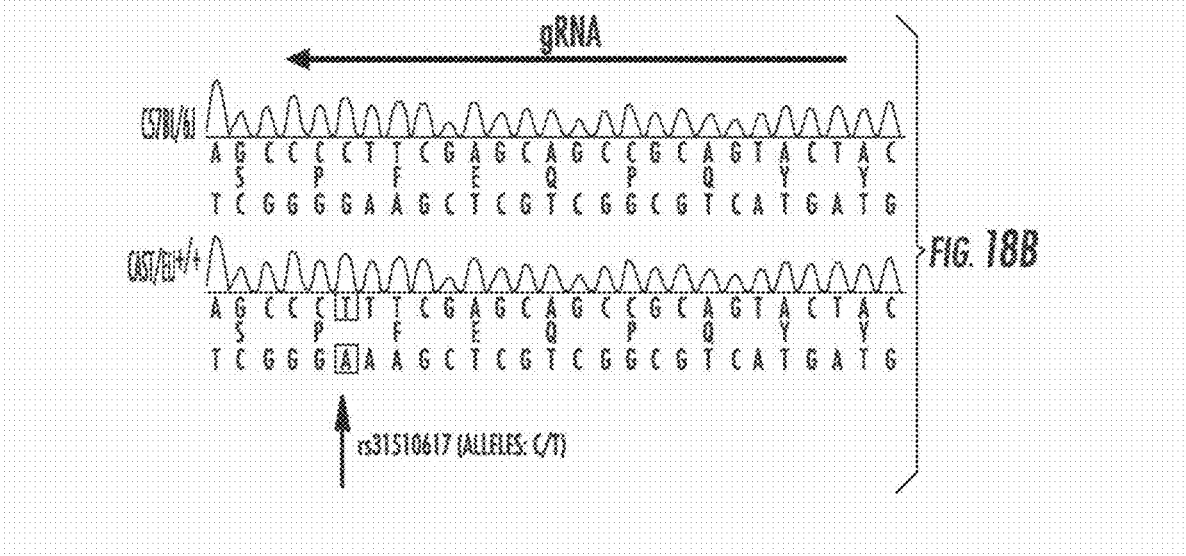
Figure 18C:
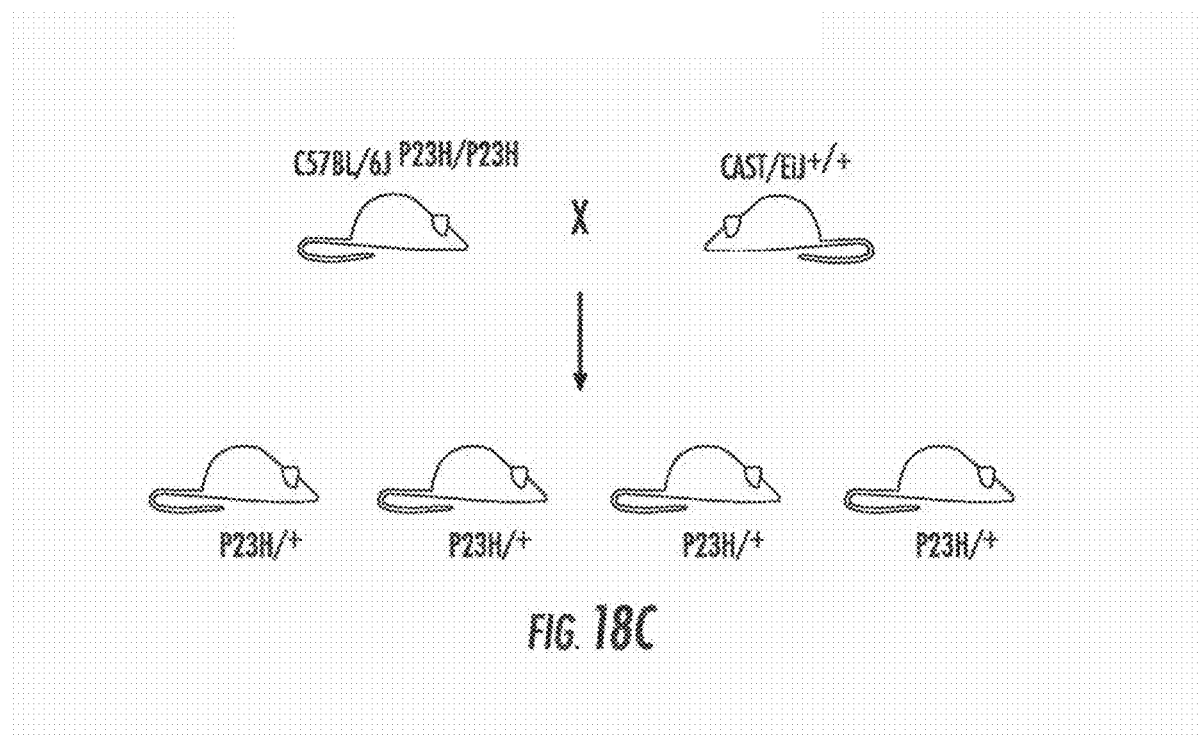
Figure 19:
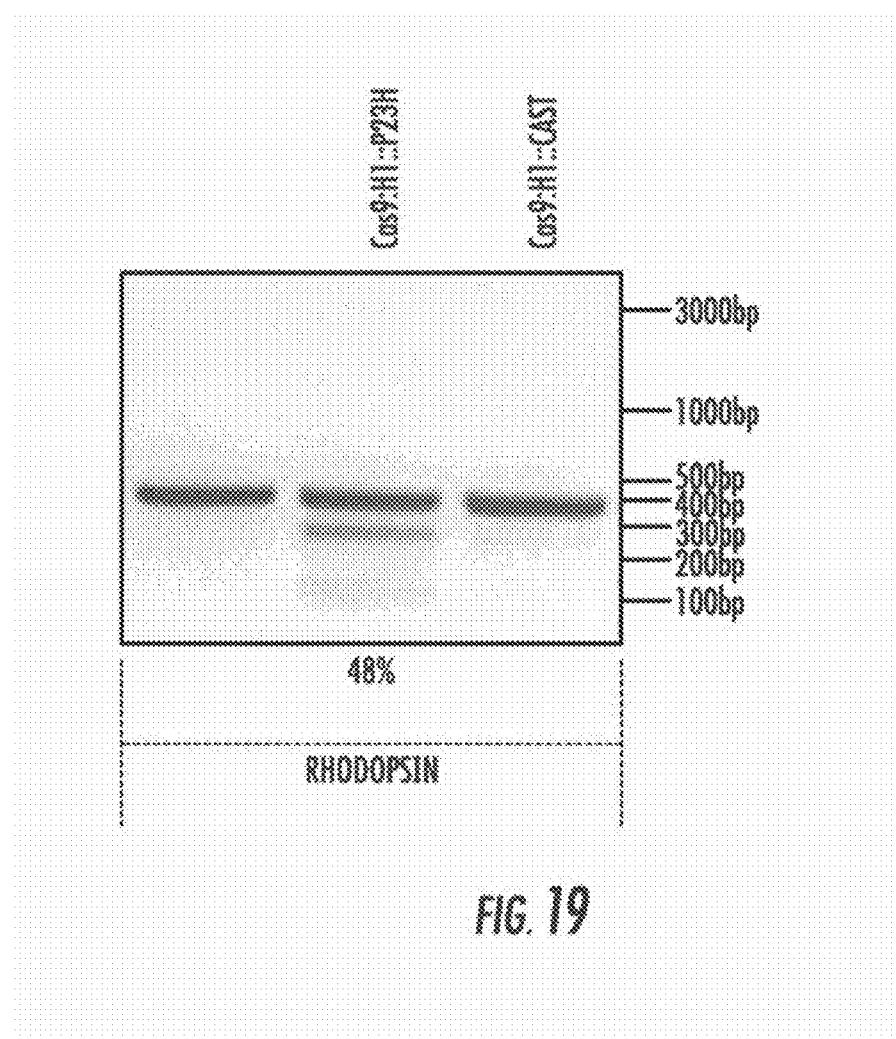

39(12):e82). A barplot of the cumulative mean CRISPR targeting density per human chromosome is shown in FIG. 5D. $GN_{19}NGG$ (orange), $AN_{19}NGG$ (blue), and $RN_{19}NGG$ (purple) indicate the respective CRISPR sites. The dotted line indicates the 35 bp reference. FIG. 5E shows the frequency and distance between adjacent CRISPR sites in the genome. Barplot of the frequency and distance of adjacent $GN_{19}NGG$ (orange) and $AN_{19}NGG$ (blue) sites is in the genome is shown. The mean and median values are inset within the plot. SeqLogo of all $GN_{19}NGG$ (top left), $AN_{19}NGG$ (top right), and $RN_{19}NGG$ (bottom) sites in the human genome are shown in FIG. 5F;

FIG. 6A, FIG. 6B, FIG. 6C, FIG. 6D, FIG. 6E, and FIG. 6F show AT/GC genome content and CRISPR site frequency: The percent AT (blue) or GC (orange) is indicated for human, cow, mouse, rat, chicken, and zebrafish genomes (FIG. 6A). The frequency of $GN_{19}NGG$ (orange) and $AN_{19}NGG$ (blue) sites normalized to AT/GC content are indicated (FIG. 6B). CRISPR site frequency by strand for $GN_{19}NGG$ (left), $AN_{19}NGG$ (middle), and $RN_{19}NGG$ (right) sites is shown in FIG. 6C. The plus strand (left column) is indicated by blue-green, and minus strand (right column) in purple-red. The $GN_{19}NGG$ (orange) and $AN_{19}NGG$ (blue) site frequency in *Drosophila*, *C. elegans*, and *S. cerevisiae* are indicated in FIG. 6D. FIG. 6E shows the percent AT (blue) or GC (orange) content and FIG. 6F shows the normalized frequency of CRISPR sites;

FIG. 7A, FIG. 7B, FIG. 7C, and FIG. 7D show CRISPR targeting of $AN_{19}NGG$ at an endogenous gene (MERTK) in H7 ES cells. A schematic diagram of the MERTK locus and various protein domains is shown in FIG. 7A. Target site in exon 2 is shown below in larger scale, indicating the CRISPR $AN_{19}NGG$ target site (sequence shown is SEQ ID NO: 32). Quantification of CRISPR targeting at exon2 by the Surveyor assay is shown in FIG. 7B. The CRISPR site in exon 2 is depicted above, with the various primers (arrows) used in the Surveyor assay; both F1:R1 and F2:R2 span the target site, while the control PCR product, F3:R3, is just outside the target site. The gel from the Surveyor assay is shown below with the three control products shown on the left, and targeting is shown on the right. Below the % indel frequency is indicated. FIG. 7C shows Sanger sequencing of mutant lines. Clonal lines were isolated and sequenced indicating that CRISPR targeting at the $AN_{19}NGG$ sites resulted in mutagenesis at this region. The aligned chromatograms show the 6 unique mutations that were cloned (wt is SEQ ID NO: 33; 412 is SEQ ID NO:34; 41 is SEQ ID NO:35; Δ2, +2 is SEQ ID NO:36; 46 is SEQ ID NO:37; 47 is SEQ ID NO:38). FIG. 7D shows Western Blot analysis for Mertk expression in H7-derived RPE cells. Lanes 1, 3, and 4 indicate knockout lines and lane 2 indicates expression from heterozygous line;

FIG. 8A, FIG. 8B, FIG. 8C, and FIG. 8D show an analysis of off-target hits induced at on-target and off-target sites by U6 or H1 expressed gRNAs. qRT-PCR analysis of the VEGFA T1 gRNA expression levels from titrating amounts of either the H1 promoter (blue) or U6 promoter (orange) is shown in FIG. 8A. On-target and off-target analysis of the VEGFA T1 is shown in FIG. 8B. Surveyor analysis is indicated on the left and the target sequences on the right with mismatches indicated in red (T1, SEQ ID NO:20; OT1-3, SEQ ID NO:21; OT1-4, SEQ ID NO:22; OT1-6, SEQ ID NO:23; OT1-11, SEQ ID NO:24). FIG. 8C is the same as FIG. 8B with the VEGFA T3 target (VEGFA T3, SEQ ID NO:25; OT3-1, SEQ ID NO:26; OT3-2, SEQ ID NO:27; OT3-4, SEQ ID NO:28; OT3-18, SEQ ID NO:29). On-target to off-target specificity of VEGFA T1 is shown in FIG. 8D. The ratio of the on-target mutagenesis/off-target mutagenesis between the H1 promoter (blue) or U6 promoter (orange) is shown. Values below the dotted line at 1.0 indicate greater off-target mutagenesis than on-target mutagenesis. For all parts, the on-target and off-target sites are labeled as in Fu et al. ((2013) *Nat. Biotechnol.* 31(9):822-6) and Cho et al. ((2014) *Genome Research* 24:132-141);

FIG. 9A and FIG. 9B show the properties of U6 versus H1 promoters in expressing gRNAs for CRISPR targeting. The top diagram in FIG. 9A shows the endogenous human U6 promoter and transcriptional start site (SEQ ID NO: 39). The bottom diagram in FIG. 9A indicates the use of the U6 promoter to drive gRNAs with different+1 nucleotides. Because U6 requires a G to initiate (top left), the panels that start with A (top right), C (bottom left), or T (bottom right) will likely initiate the first downstream G leading to a truncated gRNA (U6:GN19NGG is SEQ ID NO:40; U6:AN19NGG is SEQ ID NO:41; U6:CN19NGG is SEQ ID NO:42; U6:TN19NGG is SEQ ID NO:43). The top diagram in FIG. 9B shows the endogenous human H1 promoter and transcriptional start site (SEQ ID NO: 44). The bottom diagram in FIG. 9B indicates the use of the H1 promoter to drive gRNAs with different+1 nucleotides. H1 can initiate with a G (top left) or an A (top right) leading to full-length gRNAs. Also, H1 has been reported to allow for transcription initiating at C and T nucleotides, which would allow for full-length transcripts for any+1 nucleotide downstream of the H1 promoter (H1:$GN_{19}NGG$ is SEQ ID NO: 45; H1:AN19NGG is SEQ ID NO: 46; H1:CN19NGG is SEQ ID NO: 47; H1:TN19NGG is SEQ ID NO: 48);

FIG. 10A, FIG. 10B, FIG. 10C, FIG. 10D, and FIG. 10E show use of the H1 promoter as a bidirectional promoter to simultaneously express the Cas9 protein and guide RNA. The bidirectional H1 promoter is shown expressing Cas9 as a pol II transcript towards the left (minus strand), and a guide RNA as a pol III transcript towards the right (plus strand) (FIG. 10A). The overall expression cassette is approximately 4.4 kb. FIG. 10B shows the construct used for testing the ability to direct CRISPR-mediated cleavage from a bidirectional H1 construct. The bidirectional construct, using a gRNA targeting eGFP, was cloned into a plasmid and expressed in human stem cells expressing GFP. The loss of GFP is visually detected (middle panel, arrowheads) indicating the successful expression and targeting of GFP due to the expression construct (FIG. 10C). Successful CRISPR targeting is also shown through the Surveyor Assay with the presence of the two bands in lanes 2, and 3 (FIG. 10D). A bidirectional CRISPR construct using the H1 promoter to generate a compact targeting cassette of ~4.75b, which is within the packaging range of the adeno-associated virus, is shown in FIG. 10E. The SV40 terminator is shown in orange, and the construct is flanked by the inverted terminal repeat (ITR) sequences required for virus production;

FIG. 11A, FIG. 11B, and FIG. 11C shows a Hammerhead Ribozyme to generate the 5' end of a guide RNA. Depiction of a 5' cis-hammerhead ribozyme (SEQ ID NO: 49) and gRNA (SEQ ID NO: 50) is shown in FIG. 11A. The sequences of the hammerhead ribozyme are indicated, and the nucleotides important for catalysis are indicated (critical in red, important in orange). The location of cleavage is indicated by the arrow. Upon ribozyme cleavage (lower), the resulting gRNA is released, without constraint to any nucleotide at the newly formed 5' position. Constructs to express the hammerhead-gRNA are shown in FIG. 11B. A promoter, generally a pol III promoter like U6, H1, or T7, can be used to express the 5' cis-hammerhead ribozyme, which after self-cleavage will release the gRNA. Targeting of two loci are shown with the Surveyor Assay (HH1=SEQ ID NO: 51; HH2=SEQ ID NO: 52), with successful cleavage (arrows) by a 5' cis-hammerhead ribozyme (FIG. 11C);

FIG. 12 shows a regulatable CRISPR construct, using aptazymes to process gRNAs in the presence of specific aptamers. In particular, FIG. 12 depicts the theophylline aptamer (orange) fused to helix II of the hammerhead ribozyme forming the theophylline aptazyme, which is 5' of the gRNA (blue). Binding of theophylline stabilizes helix II that then allows for hammerhead self-cleavage, and freeing the gRNA (SEQ ID NO:50). The gRNA, along with Cas9, is now able to target cleavage by the CRISPR system. Hammerhead ribozyme, SEQ ID NO:55;

FIG. 13 shows genomic organization of the H1RNA and PARP-2 locus. Shown above is a depiction of the PARP-2 gene (blue) transcribed toward the right and the H1RNA gene (orange) transcribed to the left, drawn to scale. Below is an enlarged region of the promoter region for both genes;

FIG. 14 shows eGFP reporter for H1 pol II activity. The human H1 promoter sequence is orientated with pol II transcription of eGFP to the right. The three components to be optimized are indicated in italics;

FIG. 15 shows eGFP reporter expression. Top panels indicate endogenous H1 promoter, bottom panels indicate expression with Kozak sequence;

FIG. 16A and FIG. 16B show the bidirectional expression of Cas9 and gRNA. A schematic diagram of the bidirectional targeting construct is shown in FIG. 16A. Comparison of cleavage at two different loci using the standard two vector delivery (lanes 2 and 5) or delivery of single targeting plasmid (lanes 3 and 6) is shown in FIG. 16B. % genomic modification, as determined by T7EI assay, is indicated below each lane;

FIG. 17 shows the rhodopsin locus from the hRho:GFP knockin mouse. Above, the respective mouse and human sequences are indicated above the schematic of the rho promoter region to the end of the 3'UTR (drawn to scale). Below, enlarged region indicating the location of P23 and the gRNA, shown below (arrowhead);

FIG. 18A, FIG. 18B, and FIG. 18C show the specific targeting of the P23H allele in vivo. FIG. 18A shows P23 targeting (WT(C57BL/6J, SEQ ID NO:56; P23H (CCC→CAC), SEQ ID NO:57; WT(CAST/EiJ), SEQ ID NO:58). FIG. 18B shows the sequencing of rhodopsin from two wildtype mouse strains; the SNP is indicated by the arrow (C57BL/6J DNA sequence, SEQ ID NO:56; C57BL/6J protein sequence, SEQ ID NO:59; CAST/EiJ$^{+/+}$ DNA sequence, SEQ ID NO:58; CAST/EiJ$^{+/+}$ protein sequence, SEQ ID NO:59). FIG. 18C shows the P23H breeding scheme: the P23H homozygous mouse (black) is crossed with a WT Cast (white) and the resulting heterozygous pups (grey) will be treated by subretinal delivery of AAV5; and FIG. 19 shows allele-specific targeting of the rhodopsin locus. Comparison of cleavage of the C57BL/6J(P23H) allele vs a single base mismatch (Cast) is shown. % genomic modification determined by T7EI assay is indicated below.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Genome-editing technologies such as zinc fingers nucleases (ZFN) (Porteus, and Baltimore (2003) Science 300: 763; Miller et al. (2007) Nat. Biotechnol. 25:778-785; Sander et al. (2011) Nature Methods 8:67-69; Wood et al. (2011) Science 333:307) and transcription activator-like effectors nucleases (TALEN) (Wood et al. (2011) Science 333:307; Boch et al. (2009) Science 326:1509-1512; Moscou and Bogdanove (2009) Science 326:1501; Christian et al. (2010) Genetics 186:757-761; Miller et al. (2011) Nat. Biotechnol. 29:143-148; Zhang et al. (2011) Nat. Biotechnol. 29:149-153; Reyon et al. (2012) Nat. Biotechnol. 30:460-465) have empowered the ability to generate targeted genome modifications and offer the potential to correct disease mutations with precision. While effective, these technologies are encumbered by practical limitations as both ZFN and TALEN pairs require synthesizing large and unique recognition proteins for a given DNA target site. Several groups have recently reported high-efficiency genome editing through the use of an engineered type II CRISPR/Cas9 system that circumvents these key limitations (Cong et al. (2013) Science 339:819-823; Jinek et al. (2013) eLife 2:e00471; Mali et al. (2013) Science 339:823-826; Cho et al. (2013) Nat. Biotechnol. 31:230-232; Hwang et al. (2013) Nat. Biotechnol. 31:227-229). Unlike ZFNs and TALENs, which are relatively time consuming and arduous to make, the CRISPR constructs, which rely upon the nuclease activity of the Cas9 protein coupled with a synthetic guide RNA (gRNA), are simple and fast to synthesize and can be multiplexed. However, despite the relative ease of their synthesis, CRISPRs have technological restrictions related to their access to targetable genome space, which is a function of both the properties of Cas9 itself and the synthesis of its gRNA.

Cleavage by the CRISPR system requires complementary base pairing of the gRNA to a 20-nucleotide DNA sequence and the requisite protospacer-adjacent motif (PAM), a short nucleotide motif found 3' to the target site (Jinek et al. (2012) Science 337: 816-821). One can, theoretically, target any unique $N_{20}$-PAM sequence in the genome using CRISPR technology. The DNA binding specificity of the PAM sequence, which varies depending upon the species of origin of the specific Cas9 employed, provides one constraint. Currently, the least restrictive and most commonly used Cas9 protein is from S. pyogenes, which recognizes the sequence NGG, and thus, any unique 21-nucleotide sequence in the genome followed by two guanosine nucleotides ($N_{20}$NGG) can be targeted. Expansion of the available targeting space imposed by the protein component is limited to the discovery and use of novel Cas9 proteins with altered PAM requirements (Cong et al. (2013) Science 339: 819-823; Hou et al. (2013) Proc. Natl. Acad. Sci. U.S.A., 110 (39):15644-9), or pending the generation of novel Cas9 variants via mutagenesis or directed evolution. The second technological constraint of the CRISPR system arises from gRNA expression initiating at a 5' guanosine nucleotide. Use of the type III class of RNA polymerase III promoters has been particularly amenable for gRNA expression because these short non-coding transcripts have well-defined ends, and all the necessary elements for transcription, with the exclusion of the 1+ nucleotide, are contained in the upstream promoter region. However, since the commonly used U6 promoter requires a guanosine nucleotide to initiate transcription, use of the U6 promoter has further constrained genomic targeting sites to $GN_{19}NGG$ (Mali et al. (2013) *Science* 339:823-826; Ding et al. (2013) *Cell Stem Cell* 12:393-394).

Alternative approaches, such as in vitro transcription by T7, T3, or SP6 promoters, would also require initiating guanosine nucleotide(s) (Adhya et al. (1981) *Proc. Natl. Acad. Sci. U.S.A.* 78:147-151; Melton et al. (1984) *Nucleic Acids Res.* 12:7035-7056; Pleiss et al. (1998) *RNA* 4:1313-1317).

The presently disclosed subject matter relates to the discovery that use of the H1 promoter to express the guide-RNA (gRNA or sgRNA) more than doubles the precision of the CRISPR/Cas9 system in many genomes due to altered specificity of the 5' nucleotide. The ability to express and modify endogenous genes using the H1 promoter to express gRNAs can be used to target both $AN_{19}NGG$ and $GN_{19}NGG$ genomic sites. $AN_{19}NGG$ sites occur 15% more frequently than $GN_{19}NGG$ sites in the human genome and the increase in targeting space is also enriched at human genes and disease loci. Accordingly, the presently disclosed subject matter enhances the versatility of the CRISPR technology by more than doubling the targeting space within the human genome and other eukaryotic species. Moreover, this modification allows for higher-resolution targeting in the human genome than previously existing CRISPR, TALEN, or Zinc-finger technologies.

The presently disclosed subject matter also relates to the discovery that the use of the H1 promoter sequence as a bidirectional promoter to express Cas9 and the gRNA simultaneously allows for the generation of compact and fully-functional expression cassettes that can be inserted and delivered by viral vectors.

The presently disclosed subject matter also relates to the use of RNA ribozymes and regulatable aptazymes to express and regulate gRNA expression in vivo.

I. Expression of CRISPR Guide RNAS Using the H1 Promoter

A. Compositions

In some embodiments, the presently disclosed subject matter provides a non-naturally occurring CRISPR-Cas system comprising one or more vectors comprising: a) an H1 promoter operably linked to at least one nucleotide sequence encoding a CRISPR-Cas system guide RNA (gRNA), wherein the gRNA hybridizes with a target sequence of a DNA molecule in a cell, and wherein the DNA molecule encodes one or more gene products expressed in the cell; and b) a regulatory element operable in a cell operably linked to a nucleotide sequence encoding a Cas9 protein, wherein components (a) and (b) are located on the same or different vectors of the system, wherein the gRNA targets and hybridizes with the target sequence and the Cas9 protein cleaves the DNA molecule to alter expression of the one or more gene products.

In some embodiments, the presently disclosed subject matter provides a non-naturally occurring CRISPR-Cas system comprising one or more vectors comprising: a) an H1 promoter operably linked to at least one nucleotide sequence encoding a CRISPR-Cas system guide RNA (gRNA), wherein the gRNA hybridizes with a target sequence of a DNA molecule in a eukaryotic cell, and wherein the DNA molecule encodes one or more gene products expressed in the eukaryotic cell; and b) a regulatory element operable in a eukaryotic cell operably linked to a nucleotide sequence encoding a Type-II Cas9 protein, wherein components (a) and (b) are located on the same or different vectors of the system, whereby the gRNA targets and hybridizes with the target sequence and the Cas9 protein cleaves the DNA molecule, and whereby expression of the one or more gene products is altered. In one aspect, the target sequence can be a target sequence that starts with any nucleotide, for example, $N_{20}NGG$. In some embodiments, the target sequence comprises the nucleotide sequence $AN_{19}NGG$. In some embodiments, the target sequence comprises the nucleotide sequence $GN_{19}NGG$. In some embodiments, the target sequence comprises the nucleotide sequence $CN_{19}NGG$. In some embodiments, the target sequence comprises the nucleotide sequence $TN_{19}NGG$. In some embodiments, the target sequence comprises the nucleotide sequence $AN_{19}NGG$ or $GN_{19}NGG$. In another aspect, the Cas9 protein is codon optimized for expression in the cell. In another aspect, the Cas9 protein is codon optimized for expression in the eukaryotic cell. In a further aspect, the eukaryotic cell is a mammalian or human cell. In yet another aspect, the expression of the one or more gene products is decreased.

The presently disclosed subject matter also provides a non-naturally occurring CRISPR-Cas system comprising a vector comprising a bidirectional H1 promoter, wherein the bidirectional H1 promoter comprises: a) control elements that provide for transcription in one direction of at least one nucleotide sequence encoding a CRISPR-Cas system guide RNA (gRNA), wherein the gRNA hybridizes with a target sequence of a DNA molecule in a eukaryotic cell, and wherein the DNA molecule encodes one or more gene products expressed in the eukaryotic cell; and b) control elements that provide for transcription in the opposite direction of a nucleotide sequence encoding a Type-II Cas9 protein, whereby the gRNA targets and hybridizes with the target sequence and the Cas9 protein cleaves the DNA molecule, and whereby expression of the one or more gene products is altered. In one aspect, the target sequence can be a target sequence that starts with any nucleotide, for example, $N_{20}NGG$. In some embodiments, the target sequence comprises the nucleotide sequence $AN_{19}NGG$. In some embodiments, the target sequence comprises the nucleotide sequence $GN_{19}NGG$. In some embodiments, the target sequence comprises the nucleotide sequence $CN_{19}NGG$. In some embodiments, the target sequence comprises the nucleotide sequence $TN_{19}NGG$. In some embodiments, the target sequence comprises the nucleotide sequence $AN_{19}NGG$ or $GN_{19}NGG$. In another aspect, the Cas9 protein is codon optimized for expression in the cell. In another aspect, the Cas9 protein is codon optimized for expression in the eukaryotic cell. In a further aspect, the eukaryotic cell is a mammalian or human cell. In yet another aspect, the expression of the one or more gene products is decreased.

In some embodiments, the CRISPR complex comprises one or more nuclear localization sequences of sufficient strength to drive accumulation of the CRISPR complex in a detectable amount in the nucleus of a cell (e.g., eukaryotic cell). Without wishing to be bound by theory, it is believed that a nuclear localization sequence is not necessary for CRISPR complex activity in eukaryotes, but that including such sequences enhances activity of the system, especially as to targeting nucleic acid molecules in the nucleus. In some embodiments, the CRISPR enzyme is a type II CRISPR system enzyme. In some embodiments, the CRISPR enzyme is a Cas9 enzyme. In some embodiments, the Cas9 enzyme is S. pneumoniae. S. pyogenes, or S. thermophilus Cas9, and may include mutated Cas9 derived from these organisms. The enzyme may be a Cas9 homolog or ortholog.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell.

Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the presently disclosed subject matter in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed.

Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel (1990) Gene Expression Technology: Methods in Enzymology 185, Academic Press, San Diego, Calif. Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific.

In some embodiments, a vector comprises one or more pol III promoters, one or more pol II promoters, one or more pol I promoters, or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (e.g., Boshart et al. (1985) Cell 41:521-530), the SV40 promoter, the dihydrofolate reductase promoter, the β-actin promoter, the phosphoglycerol kinase (PGK) promoter, and the EF1α promoter.

Also encompassed by the term "regulatory element" are enhancer elements, such as WPRE; CMV enhancers; the R-U5' segment in LTR of HTLV-1 (Takebe et al. (1988) Mol. Cell. Biol. 8:466-472); SV40 enhancer: and the intron sequence between exons 2 and 3 of rabbit β-globin (O'Hare et al. (1981) Proc. Natl. Acad. Sci. USA. 78(3):1527-31). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). Advantageous vectors include lentiviruses and adeno-associated viruses, and types of such vectors can also be selected for targeting particular types of cells.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In aspects of the presently disclosed subject matter the terms "chimeric RNA", "chimeric guide RNA", "guide RNA", "single guide RNA" and "synthetic guide RNA" are used interchangeably and refer to the polynucleotide sequence comprising the guide sequence. The term "guide sequence" refers to the about 20 bp sequence within the guide RNA that specifies the target site and may be used interchangeably with the terms "guide" or "spacer".

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component.

As used herein the term "amino acid" includes natural and/or unnatural or synthetic amino acids, including glycine and both the D or L optical isomers, and amino acid analogs and peptidomimetics.

The practice of the present presently disclosed subject matter employs, unless otherwise indicated, conventional techniques of immunology, biochemistry, chemistry, molecular biology, microbiology, cell biology, genomics and recombinant DNA, which are within the skill of the art (Sambrook, Fritsch and Maniatis (1989) Molecular Cloning: A Laboratory Manual, 2nd edition; Ausubel et al., eds. (1987) Current Protocols in Molecular Biology); MacPherson et al., eds. (1995) Methods in Enzymology (Academic Press, Inc.): PCR 2; A Practical Approach); Harlow and Lane, eds. (1988) Antibodies. A Laboratory Manual; Freshney, ed. (1987) Animal Cell Culture).

Several aspects of the presently disclosed subject matter relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel (1990) Gene Expression Technology: Methods in Enzymology 185, Academic Press, San Diego. Calif. Alternatively, the recombinant expression vector can be transcribed and translated in vitro, for example using T7 promoter regulatory sequences and T7 polymerase.

Vectors may be introduced and propagated in a prokaryote. In some embodiments, a prokaryote is used to amplify copies of a vector to be introduced into a eukarvotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins.

Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson (1988) *Gene* 67: 31-40), pMAL (New England Biolabs. Beverly, Mass.) and pRIT5 (Pharmacia, Piscataway, N.J.)

that fuse glutathione S-transferase (GST), maltose E binding protein, or protein A, respectively, to the target recombinant protein.

Examples of suitable inducible non-fusion *E. coli* expression vectors include pTrc (Amrann et al. (1988) *Gene* 69:301-315) and pET 11d (Studier et al. (1990) Gene Expression Technology: Methods in Enzymology 185, Academic Press, San Diego, Calif.).

In some embodiments, a vector is a yeast expression vector. Examples of vectors for expression in yeast *Saccharomyces cerivisae* include pYepSec1 (Baldari, et al. (1987) *EMBO J.* 6: 229-234), pMFa (Kuijan and Herskowitz (1982) *Cell* 30: 933-943), pJRY88 (Schultz et al. (1987) *Gene* 54: 113-123), pYES2 (Invitrogen Corporation, San Diego, Calif.), and picZ (InVitrogen Corp, San Diego, Calif.).

In some embodiments, a vector is capable of driving expression of one or more sequences in mammalian cells using a mammalian expression vector. Examples of mammalian expression vectors include pCDM8 (Seed (1987) *Nature* 329: 840) and pMT2PC (Kaufman et al. (1987) *EMBO J.* 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook et al. (1989) Molecular Cloning: A Laboratory Manual. 2nd ed., Cold Spring Harbor Laboratory, Cold Spring Harbor Laboratory Press, Cold Spring Harbor. N.Y.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 1: 268-277), lymphoid-specific promoters (Calame and Eaton (1988) *Adv. Immunol.* 43: 235-275), in particular promoters of T cell receptors (Winoto and Baltimore (1989) *EMBO J.* 8: 729-733) and immunoglobulins (Baneiji et al. (1983) *Cell* 33: 729-740; Queen and Baltimore (1983) *Cell* 33: 741-748), neuron-specific promoters (e.g., the neurofilament promoter: Byrne and Ruddle (1989) *Proc. Natl. Acad. Sci. USA* 86: 5473-5477), pancreas-specific promoters (Edlund et al. (1985) *Science* 230: 912-916), and mammary gland-specific promoters (e.g., milk whey promoter; U.S. Pat. No. 4,873,316 and European Application Publication No. 264,166). Developmentally-regulated promoters are also encompassed. e.g., the murine hox promoters (Kessel and Gruss (1990) *Science* 249: 374-379) and the α-fetoprotein promoter (Campes and Tilghman (1989) *Genes Dev.* 3: 537-546).

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al. (1987) *J. Bacteriol.*, 169:5429-5433; and Nakata et al. (1989) *J. Bacteriol.*, 171:3553-3556), and associated genes. Similar interspersed SSRs have been identified in *Haloferax mediterranei, Streptococcus pyogenes, Anabaena,* and *Mycobacterium tuberculosis* (Groenen et al. (1993)*Mol. Microbiol.*, 10:1057-1065; Hoe et al. (1999) *Emerg. Infect. Dis.*, 5:254-263; Masepohl et al. (1996) *Biochim. Biophys. Acta* 1307:26-30: and Mojica et al. (1995) *Mol. Microbiol.*, 17:85-93). The CRISPR loci typically differ from other SSRs by the structure of the repeats, which have been termed short regularly spaced repeats (SRSRs) (Janssen et al. (2002) *OMICS J. Integ. Biol.*, 6:23-33; and Mojica et al. (2000) *Mol. Microbiol.*, 36:244-246). In general, the repeats are short elements that occur in clusters that are regularly spaced by unique intervening sequences with a substantially constant length (Mojica et al. (2000) *Mol. Microbiol.*, 36:244-246). Although the repeat sequences are highly conserved between strains, the number of interspersed repeats and the sequences of the spacer regions typically differ from strain to strain (van Embden et al. (2000) *J. Bacteriol.*, 182:2393-2401). CRISPR loci have been identified in more than 40 prokaryotes (e.g., Jansen et al. (2002) *Mol. Microbiol.*, 43:1565-1575; and Mojica et al. (2005) *J. Mol. Evol.* 60:174-82) including, but not limited to *Aeropyrum, Pyroaculum, Sulfolobus, Archaeoglobus, Halocarcula, Methanobacteriumn, Methanococcus, Methanosarcina, Methanopyrus, Pyrococcus, Picrophilus, Thernioplasnia, Corynebacterium, Mcobacterium, Streptomyces, Aquifrx, Porphvromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Mvrococcus, Campylobacter, Wolinella, Acinetobacier, Erwinia, Escherichia, Legionella, Methylococcus, Pasteurella, Photobacterium, Salmonella, Xanthomonas, Yersinia, Treponema,* and *Thermotoga.*

In general, "CRISPR system" refers collectively to transcripts and other elements involved in the expression of or directing the activity of CRISPR-associated ("Cas") genes, including sequences encoding a Cas gene, a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system).

In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". In aspects of the presently disclosed subject matter, an exogenous template polynucleotide may be referred to as an editing template. In an aspect of the presently disclosed subject matter the recombination is homologous recombination.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of S. pyogenes Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from S. pyogenes or S. pneumoniae.

In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura et al. (2000) *Nucl. Acids Res.* 28:292. Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%. 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length.

The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme).

A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CR ISPR enzyme are described in US20110059502, incorporated herein by reference. In some embodiments, a tagged CRISPR enzyme is used to identify the location of a target sequence.

In an aspect of the presently disclosed subject matter, a reporter gene which includes but is not limited to glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP), may be introduced into a cell to encode a gene product which serves as a marker by which to measure the alteration or modification of expression of the gene product. In a further embodiment of the presently disclosed subject matter, the DNA molecule encoding the gene product may be introduced into the cell via a vector. In a preferred embodiment of the presently disclosed subject matter the gene product is luciferase. In a further embodiment of the presently disclosed subject matter the expression of the gene product is decreased.

Generally, promoter embodiments of the present presently disclosed subject matter comprise: 1) a complete Pol III promoter, which includes a TATA box, a Proximal Sequence Element (PSE), and a Distal Sequence Element (DSE); and 2) a second basic Pol III promoter that includes a PSE and TATA box fused to the 5' terminus of the DSE in reverse orientation. The TATA box, which is named for its nucleotide sequence, is a major determinant of Pol III specificity. It is usually located at a position between nt. −23 and −30 relative to the transcribed sequence, and is a primary determinant of the beginning of the transcribed sequence. The PSE is usually located between nt. −45 and −66. The DSE enhances the activity of the basic Pol III promoter. In the H1 promoter, there is no gap between the PSE and the DSE.

Bidirectional promoters consists of: 1) a complete, conventional, unidirectional Pol III promoter that contains 3 external control elements: a DSE, a PSE, and a TATA box: and 2) a second basic Pol III promoter that includes a PSE and a TATA box fused to the 5' terminus of the DSE in reverse orientation. The TATA box, which is recognized by the TATA binding protein, is essential for recruiting Pol III to the promoter region. Binding of the TATA binding protein to the TATA box is stabilized by the interaction of SNAPc with the PSE. Together, these elements position Pol III correctly so that it can transcribe the expressed sequence. The DSE is also essential for full activity of the Pol III promoter (Murphy et al. (1992) *Mol. Cell Biol.* 12:3247-3261; Mittal et al. (1996)*Mol. Cell Biol.* 16:1955-1965; Ford and Hemandez (1997)*J. Biol. Chem.,* 272:16048-16055: Ford et al. (1998) *Genes. Dev.,* 12:3528-3540: Hovde et al. (2002) *Genes Dev.* 16:2772-2777). Transcription is enhanced up to 100-fold by interaction of the transcription factors Oct-1 and/or SBF/Staf with their motifs within the DSE (Kunkel and Hixon (1998) *Nucl. Acid Res.,* 26:1536-1543). Since the forward and reverse oriented basic promoters direct transcription of sequences on opposing strands of the double-stranded DNA templates, the positive strand of the reverse oriented basic promoter is appended to the 5' end of the negative strand of the DSE. Transcripts expressed under the control of the H1 promoter are terminated by an unbroken sequence of 4 or 5 Ts.

In the H1 promoter, the DSE is adjacent to the PSE and the TATA box (Myslinski et al. (2001) *Nucl. AcidRes.* 29:2502-2509). To minimize sequence repetition, this promoter was rendered bidirectional by creating a hybrid promoter, in which transcription in the reverse direction is controlled by appending a PSE and TATA box derived from the U6 promoter. To facilitate construction of the bidirectional H1 promoter, a small spacer sequence may also inserted between the reverse oriented basic promoter and the DSE.

B. Methods

In some embodiments, the presently disclosed subject matter also provides a method of altering expression of one or more gene products in a cell, wherein the cell comprises a DNA molecule encoding the one or more gene products, the method comprising introducing into the cell a non-naturally occurring CRISPR-Cas system comprising one or more vectors comprising: a) an H1 promoter operably linked to at least one nucleotide sequence encoding a CRISPR-Cas system guide RNA (gRNA), wherein the gRNA hybridizes with a target sequence of the DNA molecule; and b) a regulatory element operable in the cell operably linked to a nucleotide sequence encoding a Cas9 protein, wherein components (a) and (b) are located on the same or different vectors of the system, wherein the gRNA targets and hybridizes with the target sequence and the Cas9 protein cleaves the DNA molecule to alter expression of the one or more gene products.

In some embodiments, the presently disclosed subject matter also provides a method of altering expression of one or more gene products in a eukaryotic cell, wherein the cell comprises a DNA molecule encoding the one or more gene products, the method comprising introducing into the cell a non-naturally occurring CRISPR-Cas system comprising one or more vectors comprising: a) an H1 promoter operably linked to at least one nucleotide sequence encoding a CRISPR-Cas system guide RNA (gRNA), wherein the gRNA hybridizes with a target sequence of the DNA molecule; and b) a regulatory element operable in the eukaryotic cell operably linked to a nucleotide sequence encoding a Type-II Cas9 protein, wherein components (a) and (b) are located on the same or different vectors of the system, whereby the gRNA targets and hybridizes with the target sequence and the Cas9 protein cleaves the DNA molecule, and whereby expression of the one or more gene products is altered. In one aspect, the target sequence can be a target sequence that starts with any nucleotide, for example, $N_{20}NGG$. In some embodiments, the target sequence comprises the nucleotide sequence $AN_{19}NGG$. In some embodiments, the target sequence comprises the nucleotide sequence $GN_{19}NGG$. In some embodiments, the target sequence comprises the nucleotide sequence $CN_{19}NGG$. In some embodiments, the target sequence comprises the nucleotide sequence $TN_{19}NGG$. In some embodiments, the target sequence comprises the nucleotide sequence $AN_{19}NGG$ or $GN_{19}NGG$. In another aspect, the Cas9 protein is codon optimized for expression in the cell. In yet another aspect, the Cas9 protein is codon optimized for expression in the eukaryotic cell. In a further aspect, the eukaryotic cell is a mammalian or human cell. In another aspect, the expression of the one or more gene products is decreased.

The presently disclosed subject matter also provides a method of altering expression of one or more gene products in a eukaryotic cell, wherein the cell comprises a DNA molecule encoding the one or more gene products, the method comprising introducing into the cell a non-naturally occurring CRISPR-Cas system comprising a vector comprising a bidirectional H1 promoter, wherein the bidirectional H1 promoter comprises: a) control elements that provide for transcription in one direction of at least one nucleotide sequence encoding a CRISPR-Cas system guide RNA (gRNA), wherein the gRNA hybridizes with a target sequence of the DNA molecule; and b) control elements that provide for transcription in the opposite direction of a nucleotide sequence encoding a Type-II Cas9 protein, whereby the gRNA targets and hybridizes with the target sequence and the Cas9 protein cleaves the DNA molecule, and whereby expression of the one or more gene products is altered. In one aspect, the target sequence can be a target sequence that starts with any nucleotide, for example, $N_{20}NGG$. In some embodiments, the target sequence comprises the nucleotide sequence $AN_{19}NGG$. In some embodiments, the target sequence comprises the nucleotide sequence $GN_{19}NGG$. In some embodiments, the target sequence comprises the nucleotide sequence $CN_{19}NGG$. In some embodiments, the target sequence comprises the nucleotide sequence $TN_{19}NGG$. In another aspect, the target sequence comprises the nucleotide sequence $AN_{19}NGG$ or $GN_{19}NGG$. In another aspect, the Cas9 protein is codon optimized for expression in the cell. In yet another aspect, the Cas9 protein is codon optimized for expression in the eukaryotic cell. In a further aspect, the eukaryotic cell is a mammalian or human cell. In another aspect, the expression of the one or more gene products is decreased.

In some aspects, the presently disclosed subject matter provides methods comprising delivering one or more polynucleotides, such as or one or more vectors as described herein, one or more transcripts thereof, and/or one or proteins transcribed therefrom, to a host cell. In some aspects, the presently disclosed subject matter further provides cells produced by such methods, and organisms (such as animals, plants, or fungi) comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson (1992) *Science* 256:808-813: Nabel and Feigner (1993) TIBTECH 11:211-217: Mitani and Caskey (1993) TIBTECH 11:162-166; Dillon (1993) TIBTECH 11:167-175; Miller (1992) *Nature* 357:455-460: Van Brunt (1998) *Biotechnology* 6(10): 1149-1154: Vigne (1995) *Restorative Neurology and Neuroscience* 8:35-36: Kremer and Perricaudet (1995) *British Medical Bulletin* 51(1):31-44; Haddada et al. (1995) Current Topics in Microbiology and Immunology. Doerfler and Bohm (eds): and Yu et al. (1994) *Gene Therapy* 1:13-26.

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4.946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (e.g., Crystal (1995) *Science* 270:404-410; Blaese et al. (1995) *Cancer Gene Ther.* 2:291-297: Behr et al. (1994) *Bioconjugate Chem.* 5:382-389; Remy et al. (1994) *Bioconjugate Chem.* 5:647-654: Gao et al. (1995) *Gene Therapy* 2:710-722; Ahmad et al. (1992) *Cancer Res.* 52:4817-4820; U.S. Pat. Nos. 4,186, 183, 4,217,344, 4,235,871, 4,261,975, 4,485,054, 4,501,728, 4,774.085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (e.g., Buchscher et al. (1992) *J. Virol.* 66:2731-2739; Johann et al. (1992) *J. Virol.* 66:1635-1640: Sommnerfelt et al. (1990) *J. Virol.* 176:58-59: Wilson et al. (1989) *J. Virol.* 63:2374-2378: Miller et al. (1991) *J. Virol.* 65:2220-2224: PCT/US94/05700). In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (e.g., West et al. (1987) *Virology* 160:38-47; U.S. Pat. No. 4,797,368; WO 93/24641, Kotin (1994) *Human Gene Therapy* 5:793-801; Muzyczka (1994) *J. Clin. Invest.* 94:1351. Construction of recombinant AAV vectors are described in a number of publications, including U.S. Pat. No. 5,173,414: Tratschin et al. (1985) *Mol. Cell. Biol.* 5:3251-3260: Tratschin et al. (1984) *Mol. Cell. Biol.* 4:2072-2081; Hermonat and Muzyczka (1984) *Proc. Natl. Acad & Si. USA.* 81:6466-6470: and Samulski et al. (1989) *J. Virol.* 63:03822-3828.

Packaging cells are typically used to form virus particles that are capable of infecting a host cell. Such cells include 293 cells, which package adenovirus, and W2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panel, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55. Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts: 10.1 mouse fibroblasts, 293-T. 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr –/–, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7. HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R. MONO-MAC 6, MTD-A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1ArPNT 2, RenCa, RIN-5F, RMA/RMAS, Saos-2 cells, Sf-9, SkBr3, T2, T-47D. T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal. In some embodiments, the transgenic animal is a mammal, such as a mouse, rat, or rabbit. In certain embodiments, the organism or subject is a plant. Methods for producing transgenic animals are known in the art, and generally begin with a method of cell transfection, such as described herein.

In one aspect, the presently disclosed subject matter provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal.

In one aspect, the presently disclosed subject matter provides for methods of modifying a target polynucleotide in a eukaryotic cell. In some embodiments, the method comprises allowing a CRISPR complex to bind to the target polynucleotide to effect cleavage of the target polynucleotide thereby modifying the target polynucleotide, wherein the CRISPR complex comprises a CRISPR enzyme complexed with a guide sequence hybridized to a target sequence within the target polynucleotide.

In one aspect, the presently disclosed subject matter provides a method of modifying expression of a polynucleotide in a eukaryotic cell. In some embodiments, the method comprises allowing a CRISPR complex to bind to the polynucleotide such that the binding results in increased or decreased expression of the polynucleotide: wherein the CRISPR complex comprises a CRISPR enzyme complexed with a guide sequence hybridized to a target sequence within the polynucleotide.

In one aspect, the presently disclosed subject matter provides methods for using one or more elements of a CRISPR system. The CRISPR complex of the presently disclosed subject matter provides an effective means for modifying a target polynucleotide. The CRISPR complex of the presently disclosed subject matter has a wide variety of utility including modifying (e.g., deleting, inserting, translocating, inactivating, activating) a target polynucleotide in a multiplicity of cell types. As such the CRISPR complex of the presently disclosed subject matter has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif): that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Embodiments of the presently disclosed subject matter also relate to methods and compositions related to knocking out genes, amplifying genes and repairing particular mutations associated with DNA repeat instability and neurological disorders (Robert D. Wells, Tetsuo Ashizawa. Genetic Instabilities and Neurological Diseases, Second Edition, Academic Press, Oct. 13, 2011-Medical). Specific aspects of tandem repeat sequences have been found to be responsible for more than twenty human diseases (McIvor et al. (2010) *RNA Biol.* 7(5):551-8). The CRISPR-Cas system may be harnessed to correct these defects of genomic instability.

In yet another aspect of the presently disclosed subject matter, the CRISPR-Cas system may be used to correct ocular defects that arise from several genetic mutations further described in Traboulsi, ed. (2012) Genetic Diseases of the Eye, Second Edition, Oxford University Press.

Several further aspects of the presently disclosed subject matter relate to correcting defects associated with a wide range of genetic diseases. For example, genetic brain diseases may include but are not limited to Adrenoleukodystrophy, Agenesis of the Corpus Callosum, Aicardi Syndrome. Alpers' Disease. Alzheimer's Disease, Barth Syndrome. Batten Disease. CADASIL, Cerebellar Degeneration, Fabrv's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly.

In some embodiments, the condition may be neoplasia. In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion-related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

Examples of proteins associated with Parkinson's disease include but are not limited to α-synuclein, DJ-1, LRRK2, PINK1, Parkin, UCHL1, Synphilin-1, and NURR1.

Examples of addiction-related proteins may include ABAT for example.

Examples of inflammation-related proteins may include the monocyte chemoattractant protein-1 (MCP1) encoded by the Ccr2 gene, the C—C chemokine receptor type 5 (CCR5) encoded by the Ccr5 gene, the IgG receptor IIB (FCGR2b, also termed CD32) encoded by the Fcgr2b gene, or the Fc epsilon R1g (FCER1g) protein encoded by the Fcer1g gene, for example.

Examples of cardiovascular disease associated proteins may include IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), or CTSK (cathepsin K), for example.

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme EI catalytic subunit protein (UBE1C) encoded by the UBA3 gene, for example.

Examples of proteins associated Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1)

encoded by the FXR1 gene, or the fragile X mental retardation autosomal homolog 2 protein (FXR2) encoded by the FXR2 gene, for example.

Examples of proteins associated Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C—C motif) Ligand 2 protein (CCL2) encoded by the CCL2 gene, for example.

Examples of proteins associated Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related). EGFR (epidermal growth factor receptor), ERBB2 (v-erb-b2 erythroblastic leukemia viral oncogene homolog 2), ERBB3 (v-erb-b2 eiythroblastic leukemia viral oncogene homolog 3), ERBB4 (v-erb-b2 erythroblastic leukemia viral oncogene homolog 4), Notch 1, Notch2, Notch 3, or Notch 4, for example.

Examples of proteins associated with a secretase disorder may include PSENEN (presenilin enhancer 2 homolog (*C. elegans*)), CTSB (cathepsin B), PSEN1 (presenilin 1), APP (amyloid beta (A4) precursor protein), APHIB (anterior pharynx defective 1 homolog B (*C. elegans*)), PSEN2 (presenilin 2 (Alzheimer disease 4)), or BACEl (beta-site APP-cleaving enzyme 1), for example.

Examples of proteins associated with Amyotrophic Lateral Sclerosis may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins associated with prion diseases may include SODI (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins related to neurodegenerative conditions in prion disorders may include A2M (Alpha-2-Macroglobulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRA1D (Alpha-1D adrenergic receptor for Alpha-1D adrenoreceptor), for example.

Examples of proteins associated with immunodeficiency may include A2M [alpha-2-macroglobulin]: AANAT [arylalkylamine N-acetyltransferase]; ABCA1 [ATP-binding cassette, sub-family A (ABC1), member 1]; ABCA2 [ATP-binding cassette, sub-family A (ABC1), member 2]; or ABCA3 [ATP-binding cassette, sub-family A (ABC1), member 3]; for example.

Examples of proteins associated with Trinucleotide Repeat Disorders include AR (androgen receptor), FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS 1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydroxytryptamine (serotonin) receptor 2C), for example.

Examples of neurodevelopmental-associated sequences include A2BP1 (ataxin 2-binding protein 1), AADAT (aminoadipate aminotransferase), AANAT (arylalkylamine N-acetyltransferase), ABAT (4-aminobutyrate aminotransferase), ABCA1 (ATP-binding cassette, sub-family A (ABCI), member 1), or ABCA13 (ATP-binding cassette, sub-family A (ABC1), member 13), for example.

Further examples of preferred conditions treatable with the present system include may be selected from: Aicardi-Goutiéres Syndrome; Alexander Disease: Allan-Herndon-Dudlev Syndrome: POLG-Related Disorders; Alpha-Mannosidosis (Type II and III): Alström Syndrome: Angelman; Syndrome Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 (COFS 1): Cerebrotendinous Xanthomatosis; Comelia de Lange Syndrome; MAPT-Related Disorders: Genetic Prion Diseases; Dravet Syndrome; Early-Onset Familial Alzheimer Disease: Friedreich Ataxia [FRDA]; Fryns Syndrome; Fucosidosis; Fukuyama Congenital Muscular Dystrophy; Galactosialidosis; Gaucher Disease: Organic Acidemias; Hemophagocytic Lymphohistiocytosis; Hutchinson-Gilford Progeria Syndrome: Mucolipidosis 11; Infantile Free Sialic Acid Storage Disease: PLA2G6-Associated Neurodegeneration; Jervell and Lange-Nielsen Syndrome; Junctional Epidermolysis Bullosa; Huntington Disease; Krabbe Disease (Infantile): Mitochondrial DNA-Associated Leigh Syndrome and NARP; Lesch-Nyhan Syndrome; LIS1-Associated Lissencephaly; Lowe Syndrome: Maple Syrup Urine Disease: MECP2 Duplication Syndrome: ATP7A-Related Copper Transport Disorders: LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders: Acid Sphingonmyelinase Deficiency; Niemann-Pick Disease Type C; Glycine Encephalopathy: ARX-Related Disorders; Urea Cycle Disorders; COL1A 1/2-Related Osteogenesis Imperfecta: Mitochondrial DNA Deletion Syndromes: PLP1-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodysplasia Punctata Type 1; Roberts Syndrome; Sandhoff Disease; Schindler Disease—Type 1; Adenosine Deaminase Deficiency; Smith-Lemli-Opitz Syndrome: Spinal Muscular Atrophy, Infantile-Onset Spinocerebellar Ataxia: Hexosaminidase A Deficiency; Thanatophoric Dysplasia Type 1; Collagen Type VI-Related Disorders; Usher Syndrome Type I: Congenital Muscular Dystrophy; Wolf-Hirschhom Syndrome: Lysosomal Acid Lipase Deficiency: and Xeroderma Pigmentosum.

II. RNA Ribozymes and Regulatable Aptazymes to Express and Regulate GRNA Expression In Vivo The presently disclosed subject matter also relates to the use of RNA ribozymes and regulatable aptazymes to express and regulate gRNA expression in vivo, particularly the use of a 5' Hammerhead ribozyme for cis-processing of guide RNAs with unrestricted 1st nucleotide specificity and in vivo regulation ofgRNA function through RNA aptazymes.

Accordingly, the presently disclosed subject matter also provides an aptamer-regulated ribozyme, comprising: a) a cis-acting hammerhead ribozyme comprising a catalytic core and helix I, helix II, and helix III duplex regions extending therefrom, wherein the helix II duplex region and the helix III duplex region each comprise a loop region opposite the catalytic core, and wherein the helix II duplex region comprises an aptamer that binds to a ligand; b) a nucleotide sequence encoding a CRISPR-Cas system guide RNA (gRNA), wherein the gRNA hybridizes with a target sequence of a DNA molecule in a eukaryotic cell, and wherein the DNA molecule encodes one or more gene products expressed in the eukaryotic cell, wherein the nucleotide sequence comprises a 5' end and a 3' end, and wherein the 5' end of the nucleotide sequence is directly coupled to the helix III duplex region; wherein binding of the ligand to the aptamer produces a conformational change in the ribozyme such that the ribozyme undergoes self-cleavage between the 5' end of the nucleotide sequence and the helix III duplex region, whereby the gRNA is produced. An expression construct is also provided comprising: (i) a coding sequence which, when transcribed to RNA, produces the aptamer-regulated ribozyme; and (ii) one or more transcriptional regulatory sequences that regulate transcription of the RNA in a eukaryotic cell. A eukaryotic cell comprising the expression construct is also provided. A method of altering expression of one or more gene products in a eukaryotic cell is also provided, wherein the cell comprises a DNA molecule encoding the one or more gene products, the method comprising introducing the expression construct into the cell and contacting the cell with the ligand in an amount that alters the activity of the ribozyme, particularly wherein the cell is in mammalian or human subject. In one aspect, the ligand is theophylline.

Ribozymes are RNA molecules that catalyze a variety of chemical reactions such as self-cleavage or ligation (Long and Uhlenbeck (1993) *FASEB J.* 7:25-30). Various naturally occurring ribozymes have been identified in viruses, viroids, and protozoans. One of the first catalytic RNAs was discovered in the satellite RNA of the tobacco ring spot viroid (sTRSV) (De la Pena et al. (2003) *EMBO J.* 22: 5561-70). In vivo this pathogenic viroid was shown to act in cis and self-cleave during replication. Since the discovery of the first ribozyme, various classes of natural ribozymes, including hairpin and hammerhead ribozymes, have been identified and extensively characterized.

The hammerhead ribozyme (hRz) is one of the most extensively studied ribozymes (Long and Uhlenbeck (1993) *Faseb J.* 7: 25-30; Pley et al. (1994) *Nature* 372:68-74; Hammann et al. (2001) *Proc. Natl. Acad. Sci. USA* 98: 5503-8; Blount and Uhlenbeck (2005) *Annu. Rev. Biophys. Biomol. Struct.* 34:415-40). It is comprised of three helical regions that converge on a highly conserved catalytic core of eleven nucleotides (nts) (Khvorova et al. (2003) *Nat. Struct. Biol.* 10:708-12; Salehi-Ashtiani and Szostak (2001) *Nature* 414: 82-4). Cleavage is sequence-specific and targets a 5'-NUX-3' triplet, where N is any base, U is uracil, and X is any base except guanine. The optimal NUX for efficient and fast cleavage is GUC. Ribozyme cleavage is catalyzed when the 2' hydroxyl group from X directly 3' of the cleavage site is deprotonated. This nucleophile then attacks the scissile phosphate and, through a penta-coordinated trigonal bi-pyramidal transition state, produces a 5' and 3' product (Blount and Uhlenbeck (2005) *Annu. Rev. Biophys. Biomol. Struct.* 34:415-40).

Folding of the hRz into an active conformation is postulated to proceed through dual divalent ion binding events. A high affinity binding event occurs at 500 µM and orders the first set of tertiary interactions. The second low affinity addition of ion occurs at 10 mM and restructures the hRz stem orientations such that helix I folds away from helix III and interacts with helix II (Hammann et al. (2001) *Proc. Natl. Acad. Sci. USA* 98: 5503-8). HRzs with conserved catalytic cores that do not maintain specific stem loops are called minimal hammerhead ribozymes (mhRzs). While mhRzs are active at high divalent ion concentrations (10 mM), at lower concentrations mhRzs are effectively inert (De la Pena et al. (2003) *EMBO* 1, 22: 5561-70; Khvorova et al. (2003) *Nat. Struct. Biol.* 10:708-12). Crystal structures of natural hRz depict a "Y"-shaped molecule that has two of the stem loops interacting as "kissing loops" (Pley et al. (1994) *Nature.* 372:68-74). These tertiary interactions between unpaired bases in the stem loops are proposed to stabilize the catalytically active conformation and obviate high divalent ion conditions. Researchers have demonstrated restored in vitro catalytic activity at biologically-relevant divalent ion concentrations, between 100 and 500 µM, by reincorporating the loops into mhRz designs (De la Pena et al. (2003) *EMBO J.* 1 22: 5561-70; Khvorova et al. (2003) *Nat. Struct. Biol.* 10:708-12; Canny et al. (2004) *J. Am. Chem. Soc.* 126: 10848-9; Penedo et al. (2004) *RNA* 10: 880-8; Saksmerprome et al. (2004) *RNA* 10:1916-24; Weinberg and Rossi (2005) *FEBS Lett.* 579:1619-24). Through elucidation of the design rules for in vivo catalytic activity, hRz are now poised to be effective regulators of gene expression.

Accordingly, a hammerhead ribozyme contains a core, three stems that extend from the core. The terms "stem" and "helix" may be used interchangeably herein. Accordingly, the three stems extending from the core are referred to herein as stem I, stem II, and stem III (or helix I, helix II, and helix III), and at least one loop, which is located on the opposite end of a stem from the core. In embodiments of cis-acting ribozymes, the ribozyme contains two loops, one located at the end of stem II (or helix II) and the other located at the end of stem II (or helix III).

As used herein, a "cis-cleaving hammerhead ribozyme" is a hammerhead ribozyme that, prior to cleavage, is comprised of a single polynucleotide. A cis-cleaving hammerhead ribozyme is capable of cleaving itself.

A stem (or helix) is a nucleic acid motif that extends from the ribozyme core, at least a portion of which is double-stranded. In certain embodiments, there is a loop at the opposite end of the stem from the ribozyme core, and this loop connects the two strands of the double-stranded stem. In certain embodiments, a stem comprises 2 to 20 complementary base pairs. In certain embodiments, a stem comprises 3, 4, 5, 6, 7, 8, or 9 complementary base pairs.

In certain embodiments, at least 30% of the nucleotides in a stem are part of a complementary base pair. The remaining base pairs may be mismatched, non-complementary base pairs, or may be part of a bulge. In certain embodiments, at least 40% of the nucleotides in a stem are part of a complementary base pair. In certain embodiments, at least 50% of the nucleotides in a stem are part of a complementary base pair. In certain embodiments, at least 60% of the nucleotides in a stem are part of a complementary base pair. In certain embodiments, at least 70% of the nucleotides in a stem are part of a complementary base pair. In certain embodiments, at least 80% of the nucleotides in a stem are part of a complementary base pair. In certain embodiments, at least 90% of the nucleotides in a stem are part of a complementary base pair. In certain embodiments, at least 95% of the nucleotides in a stem are part of a complementary base pair. In certain embodiments, at least 99% of the nucleotides in a stem are part of a complementary base pair. In certain embodiments, 100% of the nucleotides in a stem are part of a complementary base pair.

A loop is a sequence of nucleotides that is not paired with another strand and is located at the distal end of a stem that is opposite the core. In certain embodiments, a loop is between 1 to 20 nucleotides long. In certain embodiments, a loop is between 2 and 10 nucleotides long. In certain embodiments, a loop is between 3 and 8 nucleotides long. The loop is numbered according to the stem to which it is attached. Therefore, loop I is located at the end of stem I opposite the core, loop II is located at the end of stem II opposite the core, and loop III is located at the end of stem III opposite the core.

As used herein, a "stem/loop" refers to the entire stem (or helix), along with any bulges within that stem, and the loop at the end of the stem. For example, stem/loop II includes stem II, including any bulges within stem II, and loop II. If a stem lacks a loop, then stem/loop refers to the stem, along with any bulges within that stem. As used herein, a "bulge" is a sequence of nucleotides that is not paired with another strand and is flanked on both sides by double-stranded nucleic acid sequences. In certain embodiments, a bulge is located within a stem. When a bulge is located within a stem, the nucleotides of the bulge are considered to be part of the stem. In certain embodiments, a hammerhead ribozyme comprises more than one bulge. In certain embodiments, a bulge within a stem is located two base pairs from the core. In certain embodiments, one or both strands of the stem contain a bulge.

As used herein, a nucleotide sequence encoding a CRISPR-Cas system gRNA comprises a 5' end and a 3' end, and the 5' end of the nucleotide sequence is directly coupled to the helix III duplex region. "Directly coupled" means that the loop, relative to active ribozyme structure in the absence of the aptamer, is interrupted at one only backbone phosphodiester bond between two residues of the loop, the backbone phosphodiester bond being replaced with phosphodiester bonds to the 5' and 3' ends of the aptamer. In the active form of the aptamer-regulated ribozyme, the 5' and 3' residues of the information transmission domain are based paired to one another to form a duplex region in order to preserve the structure of the otherwise interrupted loop.

"Ligand" or "analyte" or grammatical equivalents herein is meant to refer to any molecule or compound to be detected and that can interact with an aptamer to be designed and/or selected as described here. Suitable ligands or analytes include, but are not limited to, small chemical molecules such as environmental or clinical chemicals, pollutants or biomolecules, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including prokaryotic (such as pathogenic bacteria) and eukaryotic cells, including mammalian tumor cells), viruses, spores, etc. Illustrative analytes that are proteins include, but are not limited to, enzymes; drugs; cells; antibodies; antigens; cellular membrane antigens and receptors (neural, hormonal, nutrient, and cell surface receptors) or their natural ligands.

The hammerhead ribozyme (hRz) is an RNA motif which is capable of sustaining either in trans or in cis cleavage of a phosphodiester bond. The cis-acting hammerhead ribozyme (chRz) is a catalytic RNA that undergoes self-cleavage of its own backbone to produce two RNA products. Cis-acting hammerhead ribozymes contain three base-paired stems and a highly conserved core of residues required for cleavage. The cleavage reaction proceeds by an attack of a 2' hydroxyl oxygen of a catalytic site cytosine on the phosphorus atom attached to the 3' carbon of the same residue. This breaks the sugar phosphate backbone and produces a 2',3' cyclic phosphate.

The minimal hammerhead sequence that is required for the self-cleavage reaction includes approximately 13 conserved or invariant "core" nucleotides, most of which are not involved in forming canonical Watson-Crick base-pairs. The core region is flanked by stems I, II and III, which are in general comprised of canonical Watson-Crick base-pairs but are otherwise not constrained with respect to sequence.

Cleavage specificity of the trans-acting hammerhead ribozyme (thRz) is controlled by the hybridizing arms of the ribozyme, which anneal with the substrate in a complementary fashion and direct cleavage of the scissile phosphodiester bond. This activity is specifically directed to occur after the third nucleotide of the cleavage triplet.

The present presently disclosed subject matter provides aptamer-regulated trans-acting hammerhead ribozymes and aptamer-regulated cis-acting hammerhead ribozymes. The subject aptamer-regulated thRzs and chRzs are a versatile class of ribozymes that can be readily engineered to be responsive to a variety of ligands, and are useful in many applications. For example, aptamer-regulated thRzs and chRzs can be designed to modulate the activity of targeted genes in a ligand-dependent manner, and are therefore useful for modulating the expression of endogenous or heterologous genes.

The ribozyme domain (also herein the effector domain) can have at least two conformational states, an "off" state and an "on" state, that is defined by its activity level (reaction rate, for example) for either undergoing self-cleavage in the case of chRzs, or cleaving a target sequence in the case of thRzs. The effector domains of the presently disclosed subject matter can be switched between their "on" and "off" conformational states in response to ligand binding to the aptamer domain. Aptamer-regulated ribozymes of the presently disclosed subject matter, therefore, act as a switch whose activity is turned "on" and "off" in response to ligand binding. In certain embodiments, the ribozyme domain's function is starkly dependent on the presence or absence of the ligand, or can show a more dose-response like dependency on concentration of the ligand available to bind to the aptamer domain.

The choice of ligand to which the aptamer binds, and the ribozyme therefore is regulated by, are vast. In certain instances, the ligand is a small molecule having a molecular weight less than 2500 amu. These can be naturally or non-naturally occurring molecules, including peptides, small organic molecules (including drugs and certain metabolites and intermediates, cofactors, etc.), and metal ions merely to illustrate. Exemplary ligands that bind to an aptamer include, without limitation, small molecules, such as drugs, metabolites, intermediates, cofactors, transition state analogs, ions, metals, nucleic acids, and toxins. Aptamers may also bind natural and synthetic polymers, including proteins, peptides, nucleic acids, polysaccharides, glycoproteins, hormones, receptors and cell surfaces such as cell walls and cell membranes. The binding of a ligand to an aptamer, which is typically RNA, alters the base-pairing with the information transmission domain that is carried over as a structural change in the ribozyme domain and alters its ability to mediate cleavage of a phosphodiester bond (either self-cleavage or cleavage of a target sequence). Therefore, ligand binding affects the effector domain's ability to mediate gene inactivation, transcription, translation, or otherwise interfere with the normal activity of the target gene or mRNA, for example.

An aptamer will most typically have been obtained by in vitro selection for binding of a target molecule. However, in vivo selection of an aptamer is also possible. Aptamers have specific binding regions which are capable of forming complexes with an intended target molecule in an environment wherein other substances in the same environment are not complexed to the nucleic acid. The specificity of the binding is defined in terms of the comparative dissociation constants ($K_d$) of the aptamer for its ligand as compared to the dissociation constant of the aptamer for other materials in the environment or unrelated molecules in general. A ligand is one which binds to the aptamer with greater affinity than to unrelated material. Typically, the $K_d$ for the aptamer with respect to its ligand will be at least about 10-fold less than the $K_d$ for the aptamer with unrelated material or accompanying material in the environment. Even more preferably, the $K_d$ will be at least about 50-fold less, more preferably at least about 100-fold less, and most preferably at least about 200-fold less. An aptamer will typically be between about 10 and about 300 nucleotides in length. More commonly, an aptamer will be between about 30 and about 100 nucleotides in length.

Aptamers are readily made that bind to a wide variety of molecules. Each of these molecules can be used as a modulator of the associated ribozyme using the methods of the presently disclosed subject matter. For example, organic molecules, nucleotides, amino acids, polypeptides, target features on cell surfaces, ions, metals, salts, saccharides, have all been shown to be suitable for isolating aptamers that can specifically bind to the respective ligand. For instance, organic dyes such as Hoechst 33258 have been successfully used as target ligands for in vitro aptamer selections (Werstuck and Green (1998) *Science* 282:296-298). Other small organic molecules like dopamine, theophylline, sulforhodamine B, and cellobiose have also been used as ligands in the isolation of aptamers. Aptamers have also been isolated for antibiotics such as kanamycin A, lividomycin, tobramycin, neomycin B, viomycin, chloramphenicol and streptomycin. For a review of aptamers that recognize small molecules, see Famulok (1999) *Science* 9:324-9.

In certain embodiments, the ligand of the aptamer of an aptamer-regulated ribozyme of the presently disclosed subject matter is a cell-permeable, small organic molecule. Small organic molecules which do not have a general inhibitory effect on translation are preferred as ligands. The small molecule preferably also exhibits in vivo persistence sufficient for achieving the desired level of inhibition of translation. The molecules also can be screened to identify those that are bioavailable after, for example, oral administration. In certain embodiments of the presently disclosed subject matter, the ligand is nontoxic. The ligand may optionally be a drug, including, for example, a steroid. However, in some of the methods of controlling gene expression, it is preferable that the ligand be pharmacologically inert. In some embodiments, the ligand is a polypeptide whose presence in the cell is indicative of a disease or pathological condition. In other embodiments, the ligand for an aptamer is an antibiotic, such as chloramphenicol. In an alternative embodiment, the ligand of the aptamer is an organic dye such as Hoeschst dye 33258. In still another embodiment, the ligand may be a metal ion. In a specific embodiment, the aptamer domain of an aptamer-regulated nucleic acid responds to binding to caffeine.

Aptamers are typically developed to bind particular ligands by employing known in vivo or in vitro (most typically, in vitro) selection techniques known as SELEX (Ellington et al. (1990) *Nature* 346, 818-22; and Tuerk et al. (1990) *Science* 249, 505-10). Methods of making aptamers are also described in, for example, U.S. Pat. No. 5,582,981; PCT Publication No. WO 00/20040; U.S. Pat. No. 5,270, 163; Lorsch and Szostak (1994) *Biochemistry* 33:973; Mannironi et al. (1997) *Biochemistry* 36:9726; Blind (1999) *Proc. Natl. Acad. Sci. U.S.A.* 96:3606-3610; Huizenga and Szostak (1995) *Biochemistry* 34:656-665; PCT Publication Nos. WO 99/54506, WO 99/27133, WO 97/42317 and U.S. Pat. No. 5,756,291.

Generally, in their most basic form, in vitro selection techniques for identifying aptamers involve first preparing a large pool of oligonucleotides of the desired length that contain at least some region that is randomized or mutagenized. For instance, a common oligonucleotide pool for aptamer selection might contain a region of 20-100 randomized nucleotides flanked on both ends by an about 15-25 nucleotide long region of defined sequence useful for the binding of PCR primers. The oligonucleotide pool is amplified using standard PCR techniques, although any means that will allow faithful, efficient amplification of selected nucleic acid sequences can be employed. The DNA pool is then in vitro transcribed to produce RNA transcripts. The RNA transcripts may then be subjected to affinity chromatography, although any protocol which will allow selection of nucleic acids based on their ability to bind specifically to another molecule (e.g., a protein or any target molecule) may be used. In the case of affinity chromatography, the transcripts are most typically passed through a column or contacted with magnetic beads or the like on which the target ligand has been immobilized. RNA molecules in the pool which bind to the ligand are retained on the column or bead, while nonbinding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand. Once an aptamer sequence has been successfully identified, the aptamer may be further optimized by performing additional rounds of selection starting from a pool of oligonucleotides comprising the mutagenized aptamer sequence. For use in the present presently disclosed subject matter, the aptamer is preferably selected for ligand binding in the presence of salt concentrations and temperatures which mimic normal physiological conditions.

One can generally choose a suitable ligand without reference to whether an aptamer is yet available. In most cases, an aptamer can be obtained which binds the ligand of choice by someone of ordinary skill in the art. The unique nature of the in vitro selection process allows for the isolation of a suitable aptamer that binds a desired ligand despite a complete dearth of prior knowledge as to what type of structure might bind the desired ligand.

For an aptamer to be suitable for use in the present presently disclosed subject matter, the binding affinity of the aptamer for the ligand must be sufficiently strong and the structure formed by the aptamer when bound to its ligand must be significant enough so as to switch an aptamer-regulated ribozyme of the presently disclosed subject matter between "on" and "off" states or tune the functional level of an aptamer-regulated ribozyme.

The association constant for the aptamer and associated ligand is preferably such that the ligand functions to bind to the aptamer and have the desired effect at the concentration of ligand obtained upon administration of the ligand. For in vivo use, for example, the association constant should be such that binding occurs well below the concentration of ligand that can be achieved in the serum or other tissue. Preferably, the required ligand concentration for in vivo use is also below that which could have undesired effects on the organism.

Accordingly, certain embodiments provide methods of designing and selecting aptamers or aptamer domains that are responsive to one or more pre-selected or pre-determined ligands. The subject aptamer-regulated ribozymes may also be "tuned" so that their switching behavior is more or less responsive to ligand binding. Aptamer-regulated ribozymes may also be "tuned" so that the binding affinity of the aptamer domain is more or less sensitive to its ligand. For instance, the thermodynamic properties of intramolecular duplex formation and other 2° and 3° structures in the aptamer-regulated ribozymes may be altered so that the aptamer domain is more or less amenable to ligand binding, i.e., such as may be manifest in the dissociation constant ($K_d$) or other kinetic parameters (such as $K_{on}$ and $K_{off}$ rates). Alternatively, allosteric changes in the ribozyme domain may be more or less responsive to ligand binding upon alterations in hybridization and other intramolecular interactions that may effect 2° and 3° structures of the ribozyme domain. Forward engineering strategies for altering the thermodynamic properties of nucleic acid structures are well known in the art. For instance, increased complementary nucleic acid pairing may increase the stability of a ribozyme domain or aptamer domain.

III. Methods for Treating Neurodegenerative Diseases

The presently disclosed subject matter also provides methods for treating neurodegenerative diseases, disorders, or conditions. In some embodiments, the presently disclosed subject matter provides a method for treating an ocular neurodegenerative disease in a subject in need thereof, the method comprising: (a) providing a non-naturally occurring CRISPR-Cas system comprising one or more vectors comprising: i) an H1 promoter operably linked to at least one nucleotide sequence encoding a CRISPR-Cas system guide RNA (gRNA), wherein the gRNA hybridizes with a target sequence of a DNA molecule in a cell of the subject, and wherein the DNA molecule encodes one or more gene products expressed in the cell; and ii) a regulatory element operable in a cell operably linked to a nucleotide sequence encoding a Cas9 protein, wherein components (i) and (ii) are located on the same or different vectors of the system, wherein the gRNA targets and hybridizes with the target sequence and the Cas9 protein cleaves the DNA molecule to alter expression of the one or more gene products; and (b) administering to the subject an effective amount of the system.

By "neurodegenerative disease, disorder, or condition" is meant a disease, disorder, or condition (including a neuropathy) associated with degeneration or dysfunction of neurons or other neural cells, such as retinal photoreceptor cells. A neurodegenerative disease, disorder, or condition can be any disease, disorder, or condition in which decreased function or dysfunction of neurons, or loss or neurons or other neural cells, can occur.

Such diseases, disorders, or conditions include, but are not limited to, glaucoma, and neurodegenerative diseases, disorders, or conditions of the nervous systems, such as or associated with amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease, Huntington's disease, Parkinson's disease, Parkinson's-plus diseases, multiple system atrophy, progressive supranuclear palsy, corticobasal degeneration, dementia with Lewy bodies, frontotemporal dementia, demyelinating diseases, Guillain-Barre syndrome, multiple sclerosis, Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, epilepsy, and AIDS demential complex.

Other neurodegenerative diseases, disorders, or conditions of the nervous systems, such as or associated with alcoholism, Alexander's disease, Alper's disease, ataxia telangiectasia, Batten disease (also known as Spielmeyer-Vogt-Sjogren-Batten disease), Canavan disease, Cockayne syndrome, diabetic neuropathy, frontotemporal lobar degeneration, HIV-associated dementia, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, such as retinitis pigmentosa and associated diseases, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), Steele-Richardson-Olszewski disease, and tabes dorsalis.

Examples of ocular-related neurodegeneration include, but are not limited to, glaucoma, lattice dystrophy, retinitis pigmentosa, age-related macular degeneration (AMD), photoreceptor degeneration associated with wet or dry AMD, other retinal degeneration such as retinitis pigmentosa (RP), optic nerve drusen, optic neuropathy, and optic neuritis, such as optic neuritis resulting from multiple sclerosis. In some embodiments, the ocular neurodegenerative disease is selected from the group consisting of glaucoma, retinal degeneration, and age-related macular degeneration. In some embodiments, the ocular neurodegenerative disease is retinitis pigmentosa (RP).

Non-limiting examples of different types of glaucoma that can be prevented or treated according to the presently disclosed subject matter include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochromic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alpha-chymotrypsin glaucoma), toxic glaucoma, and glaucoma associated with intraocular tumors, retinal detachments, severe chemical burns of the eye, and iris atrophy. In certain embodiments, the neurodegenerative disease, disorder, or condition is a disease, disorder, or condition that is not associated with excessive angiogenesis, for example, a glaucoma that is not neovascular glaucoma.

As used herein, the term "disorder" in general refers to any condition that would benefit from treatment with a compound against one of the identified targets, or pathways, including any disease, disorder, or condition that can be treated by an effective amount of a compound against one of the identified targets, or pathways, or a pharmaceutically acceptable salt thereof.

As used herein, the term "treating" can include reversing, alleviating, inhibiting the progression of, preventing or reducing the likelihood of the disease, disorder, or condition to which such term applies, or one or more symptoms or manifestations of such disease, disorder or condition (e.g., a disease or disorder that causes dysfunction and/or death of retinal photoreceptor cells). In some embodiments, the treatment reduces the dysfunction and/or death of retinal photoreceptor cells. For example, the treatment can reduce the dysfunction and/or death of retinal photoreceptor cells by at least 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99% or more as compared to the dysfunction and/or death of retinal photoreceptor cells in a subject before undergoing treatment or in a subject who does not undergo treatment. In some embodiments, the treatment completely inhibits dysfunction and/or death of retinal photoreceptor cells in the subject. As used herein, a "retinal photoreceptor cell" is a specialized type of neuron found in the retina that is capable of phototransduction. In some embodiments, at least one gene product is rhodopsin.

In some embodiments, the system is packaged into a single adeno-associated virus (AAV) particle before administering to the subject. In some embodiments, administering to the subject occurs by subretinal injection. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The terms "subject" and "patient" are used interchangeably herein. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease.

IV. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Methods

Plasmid Construction: To generate the H1 gRNA-expressing constructs (see Tables 1, 2, and 3 below), overlapping oligonucleotides were assembled to create the H1 promoter fused to the 76 bp gRNA scaffold and pol III termination signal. In between the H1 promoter and the gRNA scaffold, a BamHI site was incorporated to allow for the insertion of a targeting sequence. The H1::gRNA scaffold::pol III terminator sequence was then TOPO cloned into pCR4-Blunt (Invitrogen, Carlsbad, Calif.), and sequenced verified; the resulting vector is in the reverse orientation (see below). To generate the various gRNAs used in this study, overlapping oligonucleotides were annealed and amplified by PCR using two-step amplification Phusion Flash DNA polymerase (Thermo Fisher Scientific, Rockford, Ill.), and subsequently purified using Carboxylate-Modified Sera-Mag Magnetic Beads (Thermo Fisher Scientific) mixed with 2× volume 25% PEG and 1.5M NaCl. The purified PCR products were then resuspended in $H_2O$ and quantitated using a NanoDrop 1000 (Thermo Fisher Scientific). The gRNA-expressing constructs were generated using the Gibson Assembly (New England Biolabs, Ipswich, Mass.) (Gibson et al. (2009) *Nature Methods* 6:343-345) with slight modifications for either the AflII digested plasmid (#41824, Addgene, Cambridge Mass.) for U6 expression, or BamHI digestion of plasmid just described for H1 expression. The total reaction volume was reduced from 20 µl to 20 µl.

Cell culture: The hESC line H7 and IMR-90 iPS cells (WiCell, Madison Wis.) were maintained by clonal propagation on growth factor reduced Matrigel (BD Biosciences, Franklin Lakes, N.J.) in mTeSR1 medium (Stem Cell Technologies, Vancouver, BC), in a 10% $CO_2$/5% $O_2$ incubator according to previously described protocols (Walker et al. (2010) *Nat. Commun.* 1:71; Maruotti et al. (2013) *Stem Cells Translational Medicine* 2:341-354). For passaging, hESC colonies were first incubated with 5 µM blebbistatin (Sigma-Aldrich, St. Louis, Mo.) in mTesR1, and then collected after 5-10 min treatment with Accutase (Sigma-Aldrich). Cell clumps were gently dissociated into a single cell suspension and pelleted by centrifugation. Thereafter, hPSCs were re-suspended in mTeSR1 with blebbistatin and plated at approximately 1,000-1,500 cells/$cm^2$. Two days after passage, medium was replaced with mTeSR1 (without blebbistatin) and changed daily.

Human embryonic kidney (HEK) cell line 293T (Life Technologies, Grand Island, N.Y.) was maintained at 37° C. with 5% $CO_2$/20% $O_2$ in Dulbecco's modified Eagle's Medium (DMEM) (Invitrogen) supplemented with 10% fetal bovine serum (Gibco, Life Technologies, Grand Island, N.Y.) and 2 mM GlutaMAX (Invitrogen).

Gene Targeting of H7 Cells: hESC cells were cultured in 10 µM Rho Kinase inhibitor (DDD00033325, EMD Millipore, Billerica, Mass.) 24 h prior to electroporation. Electroporation was performed using the Neon kit (Invitrogen), according to the manufacturer instruction. Briefly, on the day of electroporation, hESC were digested with Accutase (Sigma-Aldrich) for 1-2 min until colonies lifted. Importantly, colonies were not dissociated into a single cell suspension. After colonies were harvested, wet pellets were kept on ice for 15 min, and then resuspended in electroporation buffer containing gene targeting plasmids. Electroporation parameters were as follows: voltage: 1400 ms; interval: 30 ms; 1 pulse. Following electroporation, cell colonies were slowly transferred to mTeSR1 medium containing 10 µM Rho Kinase inhibitor, and then kept at room temperature for 20 min before plating on Matrigel-coated dishes and further cultured.

For analysis of clonally derived colonies, electroporated hESC were grown to subconfluence, passaged as described in the previous paragraph and plated at a density of 500 cells per 35 mm dish. Subsequently, single colonies were isolated by manual picking and further cultured.

For 293T cell transfection, ~100,000 cells/well were seeded in 24-well plates (Falcon, Corning, N.Y.) 24 hours prior to transfection. Cells were transfected in quadruplicates using Lipofectamine LTX Plus Reagent (Invitrogen) according to manufacturer's recommended protocol. For each well of a 24-well plate, 400 ng of the Cas9 plasmid and 200 ng of the gRNA plasmid were mixed with 0.5 µl of Plus Reagent and 1.5 µl of Lipofectamine LTX reagent.

Generation of Constitutively Expressed GFP ESC Lines: The H7 human ESC line (WiCell) was maintained in mTeSR1 (Stem Cell Technologies) media on Matrigel substrate. Prior to cell passaging, cells were subjected to a brief pre-treatment with blebbistatin (>5 min) to increase cell viability, treated with Accutase for 7 min, triturated to a single cell suspension, quenched with an equal volume of mTesR, pelleted at 80×g for 5 min and resuspended in mTesR containing blebbistatin. $1\times10^6$ cells were pelleted, media carefully removed and cells placed on ice for 10-15 min. 10 µg of AAV-CAGGSEGFP donor vector (#22212, Addgene) containing homology to the AAVS1 safe-harbor locus, plus 5 µg each of hAAVS1 1R+L TALENs (#35431 and 35432, Addgene) (Hockemeyer et al. (2009) *Nat. Biotechnol.* 27: 851-857; Sanjana et al. (2012) *Nature Protocols* 7: 171-192) in R-buffer were electroporated with a 100 µl tip-type using the Neon Transfection System (Life Technologies) with the following parameters: 1500V, 20 ms pulse and 1 pulse. Cells were then added gently to 1 ml of medium and incubated at room temperature for 15 min and then plated onto Matrigel-coated 35 mm dishes containing mTeSR and 50 µM blebbistatin. After 2 days, cells were seeded at a density of 1×10$^4$ after which time stable clonal sublines were manually selected with a fluorescence equipped Nikon TS100 epifluorescence microscope.

Surveyor Assay and Sequencing Analysis for Genome Modification: For Surveyor analysis, genomic DNA was extracted by resuspending cells in QuickExtract solution (Epicentre, Madison, Wis.), incubating at 65° C. for 15 min, and then at 98° C. for 10 min. The extract solution was cleaned using DNA Clean and Concentrator (Zymo Research, Irvine, Calif.) and quantitated by NanoDrop (Thermo Fisher Scientific). The genomic region surrounding the CRISPR target sites was amplified from 100 ng of genomic DNA using Phusion DNA polymerase (New England Biolabs). Multiple independent PCR reactions were pooled and purified using Qiagen MinElute Spin Column following the manufacturer's protocol (Qiagen, Valencia, Calif.). An 8 µl volume containing 400 ng of the PCR product in 12.5 mM Tris-HCl (pH 8.8), 62.5 mM KCl and 1.875 mM MgCl$_2$ was denatured and slowly reannealed to allow for the formation of heteroduplexes: 95° C. for 10 min, 95° C. to 85° C. ramped at −1.0° C./sec, 85° C. for 1 sec, 85° C. to 75° C. ramped at −1.0° C./sec, 75° C. for 1 sec, 75° C. to 65° C. ramped at −1.0° C./sec, 65° C. for 1 sec, 65° C. to 55° C. ramped at −1.0° C./sec, 55° C. for 1 sec, 55° C. to 45° C. ramped at −1.0° C./sec, 45° C. for 1 sec, 45° C. to 35° C. ramped at −1.0° C./sec, 35° C. for 1 sec, 35° C. to 25° C. ramped at −1.0° C./sec, and then held at 4° C. 1 µl of Surveyor Enhancer and 1 µl of Surveyor Nuclease (Transgenomic, Omaha, Nebr.) were added to each reaction, incubated at 42° C. for 60 min, after which, 1 µl of the Stop Solution was added to the reaction. 1 µl of the reaction was quantitated on the 2100 Bioanalyzer using the DNA 1000 chip (Agilent, Santa Clara, Calif.). For gel analysis, 2 µl of 6× loading buffer (New England Biolabs) was added to the remaining reaction and loaded onto a 3% agarose gel containing ethidium bromide. Gels were visualized on a Gel Logic 200 Imaging System (Kodak, Rochester, N.Y.), and quantitated using ImageJ v. 1.46. NHEJ frequencies were calculated using the binomial-derived equation:

$$\% \text{ gene modification} = 1 - \sqrt{1 - \frac{(a+b)}{(a+b+c)}} \times 100$$

where the values of "a" and "b" are equal to the integrated area of the cleaved fragments after background subtraction and "c" is equal to the integrated area of the un-cleaved PCR product after background subtraction (Guschin et al. (2010) *Methods in Molecular Biology* 649: 247-256).

Flow Cytometry: Following blebbistatin treatment, subconfluent hESC colonies were harvested by Accutase treatment, dissociated into a single cell suspension and pelleted. Cells were then resuspended in Live Cell Solution (Invitrogen) containing Vybrant DyeCycle ruby stain (Invitrogen) and analyzed on an Accuri C6 flow cytometer (BD Biosciences).

Quantitative Real-Time qPCR: 293T cells were seeded at 250,000 cells/well in 12-well plates (Falcon) 24 hours prior to transfection. Cells were transfected in triplicate using Lipofectamine LTX with Plus Reagent (Invitrogen) according to manufacturer's recommended protocol with a 6-dose titration of the gRNA plasmid: 0 ng, 31.25 ng, 62.5 ng, 125 ng, 250 ng, or 500 ng in each well. 48 hours posttransfection, total RNA was isolated using RNAzol RT (Molecular Research Center, Cincinnati, Ohio), and purified using Direct-zol RNA MiniPrep (Zymo). 500 ng of total RNA was dsDNase (ArticZymes; Plymouth Meeting, PA USA) treated to remove residual genomic DNA contamination and reverse transcribed in a 20 µl reaction using Superscript III reverse transcriptase (Invitrogen) following the manufacturer's recommendations. For each reaction, 0.10 µM of the following oligonucleotides were used to prime each reaction;

```
gRNA scaffold-
                                       (SEQ ID NO: 1)
CTTCGATGTCGACTCGAGTCAAAAAGCACCGACTCGGTGCCAC, U6 snRNA-
                                       (SEQ ID NO: 2)
AAAATATGGAACGCTTCACGAATTTG.
```

The underlined scaffold sequence denotes an anchor sequence added for transcript stability. Each qPCR reaction was carried out in a Biorad CFX 96 real-time PCR machine in a 10 µl volume using the SsoAdvanced™ Universal SYBR® Green Supermix (Biorad) containing 250 nM of oligonucleotide primers and 1 microliter of a 1:15 dilution of the RT reaction product from above. Reactions were carried out for 40 cycles with 95° C. denaturation, 54° C. annealing temperature and 60° C. extension steps. The following primers were used for detecting the guide RNA and reference gene respectively:

```
F1for-
                                       (SEQ ID NO: 3)
GTTTTAGAGCTAGAAATAGCAAGTTAA
and guideRNAscaffrev-
                                       (SEQ ID NO: 4)
AAGCACCGACTCGGTGCCAC
and U6snRNAF-
                                       (SEQ ID NO: 5)
CTCGCTTCGGCAGCACATATACT
and U6snRNARev-
                                       (SEQ ID NO: 6)
ACGCTTCACGAATTTGCGTGTC.
```

Relative normalized expression for each guide RNA sample and the s.e.m was calculated using the Biorad's integrated CFX manager software.

Bioinformatics: To determine all the potential CRISPR sites in the human genome, a custom Perl script was used to search both strands and overlapping occurrences of the 23-mer CRISPR sequence sites GN$_{19}$NGG or AN$_{19}$NGG. To calculate the mean and median distance values, the predicted CRISPR cut site was first defined as occurring between the third and fourth bases upstream of the PAM sequence. After sorting the sequences, the distances between all adjacent gRNAs in the genome were then calculated. This data was imported into R to calculate the mean and median statistical values, and to plot the data. To calculate the mean density, the gRNA cut sites were binned across the genome and calculated for the frequency of occurrences. This data was plotted in R using the ggplot2 package or Circos to generate a circular plot (Krzywinski et al. (2009) *Genome Research* 19:1639-1645). To calculate the occurrences in human genes or at disease loci, BEDTools utility IntersectBED (Quinlan and Hall (2010) *Bioinformatics* 26:841-842) was used to find the occurrence of overlaps with either a RefSeq BED file retrieved from the UCSC Genome Browser or a BED file from OMIM (Online Mendelian Inheritance in Man, OMIM. McKusick-Nathans Institute of Genetic Medicine, Johns Hopkins University (Baltimore, Md.), 2013). The genomes used in this study were human (hg19), mouse (mm10), rat (rn5), cow (bosTau7), chicken (galGa14), zebrafish (dr7), *drosophila* (dm3), *C. elegans* (ce10), and *S. cerevisiae* (sacCer3).

TABLE 1 gRNA targeting sequences and properties - eGFP targeting constructs indicating the eGFP coordinates, gRNA promoter, 5' nucleotide, targeting strand, PAM motif, GC content, Tm, and thermodynamic stability

| Construct | Promoter | 5' nucleotide | Strand | PAM | GC* (%) | Tm* (° C.) | 3' Stability (kcal/mol) (ΔG)** |
|---|---|---|---|---|---|---|---|
| GFP_213-191 | U6 | G | − | GGG | 65 | 68.0 | 7.9 |
| GFP_a214-192 | H1 | A | − | AGG | 65 | 66.0 | 7.6 |
| GFP_219-197 | U6 | G | − | AGG | 65 | 69.4 | 11.1 |
| GFP_285-307 | U6 | G | + | AGG | 55 | 63.8 | 7.0 |
| GFP_a292-314 | H1 | A | + | CGG | 45 | 57.3 | 8.1 |
| GFP_315-293 | U6 | G | − | TGG | 55 | 62.8 | 6.7 |
| GFP_360-382 | U6 | G | + | AGG | 60 | 67.0 | 8.2 |
| GFP_361-383 | U6 | G | + | GGG | 55 | 64.8 | 7.0 |
| GFP_583-561 | U6 | G | − | GGG | 80 | 78.9 | 8.6 |
| GFP_a584-562 | H1 | A | − | GGG | 75 | 76.9 | 9.8 |
| GFP_612-590 | U6 | G | − | CGG | 55 | 57.6 | 6.4 |
| GFP_a676_698 | H1 | A | + | CGG | 70 | 72.5 | 6.1 |
| GFP_705_683 | U6 | G | − | CGG | 60 | 63.0 | 7.8 |

*calculated based on 20 bp target sequence
**calculated for the five 3' nucleotides based on predicted DNA:DNA hybridization values

TABLE 2 gRNA targeting sequences and properties - AAVS-1 targeting sequences indicating the gRNA promoter, 5' nucleotide, targeting strand, PAM motif, GC content, Tm, and thermodynamic stability

| Construct | Promoter | 5' nucleotide | Strand | PAM | GC* (%) | Tm* (° C.) | 3' Stability (kcal/mol) (ΔG)** |
|---|---|---|---|---|---|---|---|
| AAVS1-g1 | U6 | G | + | GGG | 70 | 67.3 | 6.7 |
| AAVS1-g2 | U6 | G | + | TGG | 65 | 64.7 | 7.8 |
| AAVS1-g3 | U6 | G | − | GGG | 60 | 65.5 | 10.9 |
| AAVS1-a1 | H1 | A | − | CGG | 45 | 54.3 | 6.0 |
| AAVS1-a2 | H1 | A | − | TGG | 60 | 65.5 | 12.4 |
| AAVS1-a3 | H1 | A | − | CGG | 45 | 55.3 | 8.2 |

TABLE 3 gRNA targeting sequences and properties - sequence of the 20 base gRNA constructs targeting eGFP

| Construct | CRISPR target | SEQ ID NO: |
|---|---|---|
| GFP_213-191 | 5'GCACTGCACGCCGTAGGTCA-3' | 7 |
| GFP_a214-192 | 5'-AGCACTGCACGCCGTAGGTC-3' | 8 |
| GFP_219-197 | 5'-GCTGAAGCACTGCACGCCGT-3' | 9 |
| GFP_285-307 | 5'-GGGCGCACCATCTTCTTCA-3' | 10 |
| GFP_a292-314 | 5'-ACCATCTTCTTCAAGGACGA-3' | 11 |
| GFP_315-293 | 5'-GCCGTCGTCCTTGAAGAAGA-3' | 12 |
| GFP_360-382 | 5'-GGTGAACCGCATCGAGCTGA-3' | 13 |
| GFP_361-383 | 5'-GTGAACCGCATCGAGCTGAA-3' | 14 |
| GFP_583-561 | 5'-GCACGGGCCGTCGCCGATG-3' | 15 |
| GFP_a584-562 | 5'-AGCACGGGCCGTCGCCGAT-3' | 16 |
| GFP_612-590 | 5'-GGTGCTCAGGTAGTGGTTGT-3' | 17 |

TABLE 3-continued gRNA targeting sequences and properties - sequence of the 20 base gRNA constructs targeting eGFP

| Construct | CRISPR target | SEQ ID NO: |
|---|---|---|
| GFP_a676_698 | 5'-ACCGCCGCCGGGATCACTCT-3' | 18 |
| GFP_705_683 | 5'-GTCCATGCCGAGAGTGATCC-3' | 19 |

Results

In order to expand the current limitations of CRISPR/Cas9 targeting, it was tested whether, instead of U6, H1 pol III could be used as an alternative promoter (Baer et al. (1990) Nucleic Acids Res. 18:97-103). Because H1 can express transcripts with either purine (nucleotide R) located at the +1 position, it was hypothesized that along with the S. pyogenes Cas9, the CRISPR targeting space could be expanded by allowing for cleavage at both $AN_{19}NGG$ and $GN_{19}NGG$ sites (FIG. 1A). To demonstrate site-specific cleavage by H1 expressed gRNAs, a reporter assay was developed to measure CRISPR-mediated cleavage of a GFP target gene integrated at the AAVS-1 locus in the H7 human embryonic stem cell line (hESC; FIG. 1B) (Hockemeyer et al. (2009) Nat. Biotechnol. 27:851-857). The loss of GFP fluorescence due to coding sequence disruption was measured as a proxy for error-prone non-homologous end joining (NHEJ) frequency; notably, the assay would underestimate NHEJ, as in-frame mutations or indels that do not disrupt GFP fluorescence would not be detected (FIG. 1B and FIG. 1C). H7 cells were electroporated with equimolar ratios of Cas9 and gRNA expression plasmids and cells were visualized for GFP fluorescence after colony formation. In contrast to the negative control electroporation, all gRNA constructs from the U6 and H1 promoters tested showed a mosaic loss of GFP signals in cells undergoing targeted mutation (FIG. 1C and data not shown). Quantitation of total cell number with a nuclear stain enabled cell-based analysis of GFP fluorescence by flow cytometry. Although 100% of constructs resulted in NHEJ, as demonstrated by loss of GFP fluorescence, the range of efficiencies varied for both U6 and H1 constructs (FIG. 1C, right and data not shown). By expressing gRNAs from either the U6 or H1 promoters, this demonstrates that mutagenesis of the GFP gene can occur at $GN_{19}NGG$ or $AN_{19}NGG$ sites, respectively.

To confirm and broaden these results with another cell line, a GFP expressing HEK-293 cell line expressing GFP at the same locus was targeted with the same gRNA constructs as above. By Surveyor analysis (Qiu et al. (2004) BioTechniques 36:702-707), a range of editing efficiencies that varied by promoter type and targeting location was detected (FIG. 1D and FIG. 2). By using unmodified IMR90.4 induced pluripotent cells (hiPSCs), the ability to modify an endogenous gene by targeting the AAVS-1 locus within the intronic region of the PPP1R12C gene was also confirmed. Targeted cleavage from H1 and U6 driven gRNAs was observed with comparable efficiencies as measured by the Surveyor Assay (FIG. 3A, FIG. 3B, and FIG. 3C).

In order to determine the potential increase in targeting space, bioinformatic analysis was performed to assess the available CRISPR sites in the human genome. While $AN_{19}NGG$ sites might be predicted to occur roughly at the same frequency as $GN_{19}NGG$ sites, it was found that they are actually 15% more common (FIG. 4A, FIG. 4B, FIG. 4C, FIG. 4D, FIG. 5A, FIG. 5B, FIG. 5C, FIG. 5D, FIG. 5E, and FIG. 5F); thus changing specificity from $GN_{19}NGG$ to $RN_{19}NGG$ more than doubles the number of available sites (approximately 115% increase). With a few exceptions (chr16, chr17, chr19, chr20, and chr22), $AN_{19}NGG$ sites are present at higher frequencies than $GN_{19}NGG$ sites on each chromosome. To compare the average genome-wide targeting densities, the mean distances between adjacent CRISPR sites in the genome were calculated for $GN_{19}NGG$ (59 bp), $AN_{19}NGG$ (47 bp), and $RN_{19}NGG$ sites (26 bp) (FIG. 4B). Additionally, $AN_{19}NGG$ sites were even more enriched at relevant regions of targeting in the human genome. A 20% increase in $AN_{19}NGG$ sites in human genes, and a 21% increase at disease loci obtained from the OMIM database were found (FIG. 4C). 1165 miRNA genes from the human genome also were examined and it was found that 221 of these genes could be targeted through one or more $AN_{19}NGG$ sites, but not through a $GN_{19}NGG$ site (data not shown). Given that the efficiency of homologous recombination negatively correlates with increasing distance from cut sites, the increase in CRISPR targeting sites by use of the H1 promoter should facilitate more precise genomic targeting and mutation correction (Ran et al. (2013) Cell 6:1380-1389).

As CRISPR technology is increasingly utilized for genomic engineering across a wide array of model organisms, the potential impact of the use of the H1 promoter in other genomes was determined. This analysis was carried out on 5 other vertebrate genomes that had high genomic conservation at the H1 promoter (Mouse; Rat; Chicken; Cow; and Zebrafish). In all cases, a higher number of $AN_{19}NGG$ compared to $GN_{19}NGG$ sites was found: +9% Cow; +14% Chicken; +19% Rat; +21% Mouse; and +32% Zebrafish (FIG. 4C). One explanation for this prevalence could be due to the higher AT content (FIG. 6A, FIG. 6B, FIG. 6C, FIG. 6D, FIG. 6E, and FIG. 6F). In the human genome, normalizing the $GN_{19}NGG$ and ANt9NGG site occurrences to AT content brings the frequencies closer to parity, although this does not hold true for all genomes (FIG. 6A and FIG. 6F). Nevertheless, this demonstrates the utility of using the H1 promoter, which more than doubles the currently available CRISPR targeting space in the human genome, and similarly in all other genomes tested.

Next, the ability to target an $AN_{19}NGG$ site in an endogenous gene with the H1 promoter construct was demonstrated. Using H7 cells, the second exon of the MERTK locus, a gene involved with phagocytosis in the retinal pigment epithelium and macrophages and that when mutated causes retinal degeneration, was targeted (D'Cruz et al. (2000) Human Molecular Genetics 9:645-651) (FIG. 7A and FIG. 7B). To estimate the overall targeting efficiency, DNA was harvested from a population of cells that were electroporated, and the Surveyor Assay was performed. The region surrounding the target sites was amplified with two independent PCR reactions and a 9.5% and 9.7% indel frequency was calculated (FIG. 7B). Next, 42 randomly chosen clones were isolated and tested for mutation by Surveyor analysis (data not shown). Sequencing revealed that 7/42 (16.7%) harbored mutations clustering within 3-4 nucleotides upstream of the target PAM site. 6/7 clones had unique mutations (1 clone was redundant) and 3 of these were bi-allelic frame-shift mutations resulting in a predicted null MERTK allele that was confirmed by Western Blot analysis (FIG. 7C and FIG. 7D). Taken together, these results demonstrate the ability to effectively target an $AN_{19}NGG$ site located at an endogenous locus.

Since the occurrence of off-target mutations with the CRISPR-Cas9 system has become an increasing concern, how use of the H1 promoter might affect off-targeting was examined, using the above-described GFP gRNA constructs as a model system. Surveyor Analysis was used to examine three genomic loci that were bioinformatically predicted to be off-target sites (GFP_11-33, GFP_219-197, and GFP_315-293). Two of these constructs (GFP_219-197, and GFP_315-293) were $GN_{19}NGG$ target sites, allowing for expression with both promoters. One (GFP_11-33), an $AN_{19}NGG$ site, was expressed from the U6 promoter by appending a 5'-G nucleotide. In all three off-target loci examined, any off-target cleavage was unable to be detected (data not shown). However, the lack of detectable off-targets could result from the initial selection of the GFP gRNA targets, in which sites were selected based upon low homology to other genomic loci. Thus, it was reasoned that a more stringent challenge would be to compare gRNA expression from H1 and U6 promoters at targeting sites specifically known to elicit high levels of off-target hits (Fu et al. (2013) *Nat. Biotechnol.* 31:822-826; Pattanayak et al. (2013) *Nat. Biotechnol.* 31(9):839-43; Cho et al. (2014) *Genome Research* 24:132-141). Furthermore, the 5' nucleotide flexibility of the H1promoter allowed for a direct comparison of identical gRNAs targeting $GN_{19}NGG$ sites between U6 and H1 promoters. Two sites previously reported from Fu et al. (2013) were tested: VEGFA site 1 (T1) and VEGFA site 3 (T3) (Table 4, FIG. 8A, FIG. 8B, FIG. 8C, and FIG. 8D) ((Fu et al. (2013) *Nat. Biotechnol.* 31:822-826; Cho et al. (2014) *Genome Research* 24:132-141). Because increased gRNA and Cas9 concentrations have been shown to result in increased off-target hits ((Fu et al. (2013) *Nat. Biotechnol.* 31:822-826; Pattanayak et al. (2013) *Nat. Biotechnol.* 31(9): 839-43; Hsu et al. (2013) *Nat. Biotechnol.* 31(9):827-32), it was reasoned that the lower gRNA expression level from the H1 promoter (Boden et al. (2003) *Nucleic Acids Res.* 31:5033-5038; An et al. (2006) *Molecular Therapy: The Journal of the American Society of Gene Therapy* 14:494-504; Makinen et al. (2006) *The Journal of Gene Medicine* 8:433-44) might also reduce off-target effects. Using qRT-PCR, the relative levels of VEGFA T1 gRNA from the H1 and U6 promoters were tested, confirming the expected reduced level of expression from the H1 promoter (FIG. 8A). For the VEGFA T1 site, the efficiency of cutting at the on-target loci, as well as four off-target loci, was tested. In comparison with the U6 promoter, cutting at the on-target loci was comparable or slightly reduced; however, the H1 promoter expressed gRNAs were notable more stringent at the examined off-target loci indicating greater specificity (Off-target 1: 8% vs. 25%; Off-target 2: undetectable vs. 20%; and Off-target 4: 9% vs. 26%) (Table 4, FIG. 8A, FIG. 8B, FIG. 8C, and FIG. 8D). At the VEGFA T3 site, equal targeting between the two promoter constructs (26%) was detected, but again lower levels of off-target cutting were observed with the H1 promoter (Table 4, FIG. 8A, FIG. 8B, FIG. 8C, and FIG. 8D). While further studies on H1 and U6 promoters expressed gRNAs need to be performed, the data suggests possibly greater specificity from H1 expressed gRNAs.

An additional off-targeting related advantage of use of the H1 promoter approach relates to the recently described and promising approach of employing cooperative offset nicking with the D10A Cas9 mutant to mitigate potential off-target effects ((Ran et al. (2013) *Cell* 6:1380-1389; Mali et al. (2013) *Nat. Biotechnol.* 31(9):833-8). This approach has stringent targeting needs as it requires identification of two flanking CRISPR sites, oriented on opposing strands, and within approximately 20 bp of the cut site (Ran et al. (2013) *Cell* 154(6):1380-9). The additional targeting density provided by use of the H1 promoter would be expected to aid in the identification of suitable flanking sites.

Accumulating evidence for *S. pyogenes* Cas9 targeting in vitro and in vivo indicates that the Cas9:gRNA recognition extends throughout the entire 20 base pair targeting site. First, in testing >$10^{12}$ distinct variants for gRNA specificity in vitro, one study found that the +1 nucleotide plays a role in target recognition. Furthermore, positional specificity calculations from this data show that the 5' nucleotide contributes a greater role in target recognition than its 3' neighbor, indicating that the "seed" model for CRISPR specificity might overly simplify the contribution of PAM-proximal nucleotides (Pattanayak et al. (2013) *Nat. Biotechnol.* 31(9):839-4328). Secondly, alternative uses such as CRISPR interference (CRISPRi), which repurposes the CRISPR system for transcriptional repression, found that 5' truncations in the gRNA severely compromised repression, and 5' extensions with mismatched nucleotides—such as mismatched G bases for U6 expression—also reduce the repression efficiency, suggesting that both length (20 nt) and 5' nucleotide context are important for proper Cas9 targeting (Ran et al. (2013) *Cell* 154(6):1380-9; Mali et al. (2013) *Nat. Biotechnol.* 31(9):833-8; Larson et al. (2013) *Nature Protocols* 8:2180-2196; Qi et al. (2013) *Cell* 152:1173-1183; Shan et al. (2013) *Nat. Biotechnol.* 31:686-688). Finally, crystal structure data further supports the experimental data and importance of the 5' nucleotide in Cas9, as significant contacts are made with the 5' nucleotide of the gRNA and 3' end of the target DNA (Jinek et al. (2014) *Science* 343: 6176); Nishimasu et al. (2014) *Cell* 156:935-949).

For increased targeting space, the use of alternate Cas9 proteins has been shown to be effective, as in *N. meningitides* and *S. thermophiles* (Hou et al. (2013) *Proc. Natl. Acad. Sci. U.S.A.* 110(39):15644-9; Esvelt et al. (2013) *Nature Methods* 10(11):1116-21). However, despite the potential of these alternative proteins, the PAM restrictions from the other type II systems that have been reported have more stringent requirements (data not shown; Cong et al. (2013) *Science* 339:819-823; Hou et al. (2013) *Proc. Natl. Acad. Sci. USA.*, 110(39):15644-9). In contrast, modified gRNA expression by use of the H1 promoter would be expected to greatly expand the targeting repertoire with any Cas9 protein irrespective of PAM differences. When the respective gRNAs targets for orthologous Cas9 proteins ($AN_{23}NNNNGATT$ vs. $GN_{23}NNNNGATT$ for *N. meningitides* and $AN_{17}NNAGAAW$ vs. $N_{17}NNAGAAW$ for *S. thermophiles*) was quantitated, a 64% and 69% increase in the gRNA sites with a 5'-A nucleotide were found, indicating an even greater expansion of targeting space through use of the H1 promoter with alternate Cas9 proteins (Table 5). As suggested in plants, use of different promoters can expand the frequency of CRISPR sites. While the U6 promoter is restricted to a 5' guanosine nucleotide, the U3 promoter from rice is constrained to a 5' adenosine nucleotide further highlighting the need for different promoters in different systems to increase targeting space (Shan et al. (2013) *Nat. Biotechnol.* 31:686-688). Conveniently, sole use of the H1 promoter can be leveraged to target $AN_{19}NGG$ and $GN_{19}NGG$ sites (and possibly $CN_{19}NGG$ or $TN_{19}NGG$ sites (Tuschl (2002) *Nat. Biotechnol.* 20: 446-448)) via a single promoter system (FIG. 9A and FIG. 9B). This in turn can be employed to expand targeting space of both current and future Cas9 variants with altered sites restrictions.

With enhanced CRISPR targeting through judicious site selection, improved Cas9 variants, optimized gRNA architecture, or additional cofactors, an increase in specificity throughout the targeting sequence will likely result, placing greater importance on the identity of the 5' nucleotide. As a research tool, this will allow for greater manipulation of the genome while minimizing confounding mutations, and for future clinical applications, high targeting densities coupled with high-fidelity target recognition will be paramount to delivering safe and effective therapeutics.

TABLE 4

Frequency of indels induced at on-target and off-target sites by U6 or H1 expressed gRNAs

| Target | Promoter | Full-length target | Indel mutation frequency (%) | Seq ID NO: |
|---|---|---|---|---|
| VEGFA-T1 | U6 | GGGTGGGGGGAGTTTGCTCCtGG | 24 | 20 |
| VEGFA-T1 | H1 | GGGTGGGGGGAGTTTGCTCCtGG | 16 | 20 |
| OT1-3 | U6 | GGATGGAGGGAGTTTGCTCCtGG | 25 | 21 |
| OT1-3 | H1 | GGATGGAGGGAGTTTGCTCCtGG | 8 | 21 |
| OT1-4 | U6 | GGGAGGGTGGAGTTTGCTCCtGG | 20 | 22 |
| OT1-4 | H1 | GGGAGGGTGGAGTTTGCTCCtGG | Not detected | 22 |
| OT1-6 | U6 | CGGGGGAGGGAGTTTGCTCCtGG | Not detected | 23 |
| OT1-6 | H1 | CGGGGGAGGGAGTTTGCTCCtGG | Not detected | 23 |
| OT1-11 | U6 | GGGGAGGGGAAGTTTGCTCCtGG | 26 | 24 |
| OT1-11 | H1 | GGGGAGGGGAAGTTTGCTCCtGG | 9 | 24 |
| VEGFA-T3 | U6 | GGTGAGTGAGTGTGTGCGTGtGG | 26 | 25 |
| VEGFA-T3 | H1 | GGTGAGTGAGTGTGTGCGTGtGG | 26 | 25 |
| OT3-1 | U6 | GGTGAGTGAGTGTGTGTGTGaGG | 20 | 26 |
| OT3-2 | H1 | AGTGAGTGAGTGTGTGTGTGaGG | 13 | 27 |
| OT3-4 | U6 | GCTGAGTGAGTGTATGCGTGtGG | 16 | 28 |
| OT3-4 | H1 | GCTGAGTGAGTGTATGCGTGtGG | 11 | 28 |
| OT3-18 | U6 | TGTGGGTGAGTGTGTGCGTGaGG | Not detected | 29 |
| OT3-18 | H1 | TGTGGGTGAGTGTGTGCGTGaGG | Not detected | 29 |

TABLE 5

Bioinformatic analysis of alternative Cas9 targeting sites in the human genome. Columns moving from left to right indicate the Cas9 species of origin, the CRISPR target site, the frequency of occurrence in the unmasked human genome, and the frequency of occurrence in the repeat-masked human genome. The percent increase is indicated next the appropriate values in bold.

| Cas9 | Target site | Frequency (unmasked) | Frequency (masked) |
|---|---|---|---|
| S. pyogenes | $GN_{19}NGG$ | 69,041,571 | 33,076,776 |
|  | $AN_{19}NGG$ | 81,077,137 (17%) | 37,795,743 (14%) |
| N. meningitis | $GN_{23}NNNNGATT$ | 4,055,280 | 3,227,027 |
|  | $AN_{23}NNNNGATT$ | 6,942,105 (71%) | 1,966,548 (64%) |
| T. thermophilus | $GN_{17}NNAGAAW$ | 5,400,222 | 2,723,164 |
|  | $AN_{17}NNAGAAW$ | 10,383,453 (92%) | 4,593,021 (69%) |

Discussion

Increasing CRISPR targeting space and reducing the potential for off-target effects have broad implications for genomic engineering. For increased targeting space, the use of alternate Cas9 proteins has been shown to be effective, as in *S. thermophilus* (NNAGAAW) and *N. meningitides* (NNNNGATT), yet PAM restrictions from other type II systems reported so far have more stringent requirements and therefore reduce the sequence space available for targeting when used alone (data not shown and Cong et al. (2013) *Science* 339:819-823; Hou et al. (2013) *Proc. Natl. Acad. Sci. USA.*, 110(39):15644-9). In contrast, modified gRNA expression by use of the H1 promoter would be expected to greatly expand the targeting repertoire with any Cas9 protein. In plants, while the U6 promoter is restricted to a 5' guanosine nucleotide, the U3 promoter from rice is constrained to a 5' adenosine nucleotide. As recently suggested, use of both promoters could expand the frequency of CRISPR sites in plant genomes (Shan et al. (2013) *Nat. Biotechnol.* 31:686-688). Conveniently, sole use of the H1 promoter can be leveraged to target $AN_{19}NGG$ and $GN_{19}NGG$ sites in vertebrate genomes via a single promoter system. This in turn can be employed to expand targeting space of both current and future Cas9 variants with altered sites restrictions.

Similarly with ZFN or TALEN technologies, one approach to mitigate potential off-target effects might be to employ cooperative offset nicking with the Cas9 mutant (D10A) (Mali et al. (2013) *Nat. Biotechnol.* 31(9):833-8; Ran et al. (2013) *Cell* 154(6):1380-9). This requires identification of two flanking CRISPR sites on opposing strands, and the additional targeting density provided by $AN_{19}$ NGG sites would be expected to augment this approach. An added benefit over the U6 promoter may also be to reduce spurious cleavage; as several groups have reported that increased gRNA and Cas9 concentrations correlate with an increase in the propensity for off-target mutations (Pattanayak et al. (2013) *Nat. Biotechnol.* 31(9):839-43; Hsu et al. (2013) *Nat. Biotechnol.*, 31(9):827-32; Fu et al. (2013) *Nat. Biotechnol.* 31(9):822-6), the lower level of expression provided by the H1 promoter may result in reduced off-target cutting. Additionally, Pattanayak et al. reported that Cas9:gRNA recognition extends throughout the entire 20 base pair targeting site (Pattanayak et al. (2013) *Nat. Biotechnol.* 31(9):839-43). In testing $>10^{12}$ distinct variants for gRNA specificity, the authors found that the +1 nucleotide contributed to target recognition, indicating that the "seed" model (PAM-proximal nucleotides) for CRISPR specificity is overly simplified. With enhanced CRISPR targeting through judicious site selection, improved Cas9 variants, optimized gRNA architecture, or additional cofactors, an increase in specificity throughout the 23 bp targeting sequence will likely result, placing greater importance on the identity of the 5' nucleotide. As a research tool, this will allow for greater manipulation of the genome while minimizing confounding mutations, and for future clinical applications, high targeting densities coupled with high-fidelity target recognition will be paramount to delivering safe and effective therapeutics.

Example 2

FIG. 10A, FIG. 10B, FIG. 10C, FIG. 10D, and FIG. 10E show use of the H1 promoter as a bidirectional promoter to simultaneously express the Cas9 protein and guide RNA. The bidirectional H1 promoter is shown expressing Cas9 as a pol II transcript towards the left (minus strand), and a guide RNA as a pol III transcript towards the right (plus strand). The overall expression cassette is approximately 4.4 kb (FIG. 10A). To test the ability to direct CRISPR-mediated cleavage from a bidirectional H1 construct, the bidirectional construct, using a gRNA targeting eGFP, was cloned into a plasmid and expressed in human stem cells expressing GFP (FIG. 10B). The loss of GFP was visually detected (FIG. 10C; middle panel, arrowheads) indicating the successful expression and targeting of GFP due to the expression construct. Successful CRISPR targeting was also shown through the Surveyor Assay with the presence of the two bands in lanes 2, and 3 (FIG. 10D). A bidirectional CRISPR construct using the H1 promoter to generate a compact targeting cassette of ~4.75b, which is within the packaging range of the adeno-associated virus (FIG. 10E). The SV40 terminator is shown in orange, and the construct is flanked by the inverted terminal repeat (ITR) sequences required for virus production;

Methods

Plasmid Construction: To generate the H1 bidirectional construct, the human codon optimized Cas9 gene, and an SV40 terminator was fused to the 230 bp H1 promoter (SEQ ID NO:54) where the pol II transcript is endogenously found (minus strand). In between the H1 promoter and the gRNA scaffold, an AvrII site was engineered to allow for the insertion of targeting sequence. The SV40[rev]::hcas9[rev]::H1::gRNA scaffold::pol III terminator sequence was then cloned into an NdeI/XbaI digest pUC19 vector. To generate the various gRNAs used in this study, overlapping oligonucleotides were annealed and amplified by PCR using two-step amplification Phusion Flash DNA polymerase (Thermo Fisher Scientific, Rockford, Ill.), and subsequently purified using Carboxylate-Modified Sera-Mag Magnetic Beads (Thermo Fisher Scientific) mixed with 2× volume 25% PEG and 1.5M NaCl. The purified PCR products were then resuspended in $H_2O$ and quantitated using a NanoDrop 1000 (Thermo Fisher Scientific). The gRNA-expressing constructs were generated using the Gibson Assembly (New England Biolabs, Ipswich, Mass.) (Gibson et al. (2009) *Nature Methods* 6:343-345) with slight modifications. The total reaction volume was reduced from 20 µl to 2 µl.

Cell Culture: The hESC line H7 and IMR-90 iPS cells (WiCell, Madison Wis.) were maintained by clonal propagation on growth factor reduced Matrigel (BD Biosciences, Franklin Lakes, N.J.) in mTeSR1 medium (Stem Cell Technologies, Vancouver, BC), in a 10% $CO_2$/5% $O_2$ incubator according to previously described protocols (Walker et al. (2010) *Nat. Commun.* 1:71; Maruotti et al. (2013) *Stem Cells Translational Medicine* 2:341-354). For passaging, hESC colonies were first incubated with 5 µM blebbistatin (Sigma-Aldrich, St. Louis, Mo.) in mTesR1, and then collected after 5-10 min treatment with Accutase (Sigma-Aldrich). Cell clumps were gently dissociated into a single cell suspension and pelleted by centrifugation. Thereafter, hPSCs were re-suspended in mTeSR1 with blebbistatin and plated at approximately 1,000-1,500 cells/$cm^2$. Two days after passage, medium was replaced with mTeSR1 (without blebbistatin) and changed daily.

Human embryonic kidney (HEK) cell line 293T (Life Technologies, Grand Island, N.Y.) was maintained at 37° C. with 5% $CO_2$/20% $O_2$ in Dulbecco's modified Eagle's Medium (DMEM) (Invitrogen) supplemented with 10% fetal bovine serum (Gibco, Life Technologies, Grand Island, N.Y.) and 2 mM GlutaMAX (Invitrogen).

Gene Targeting of H7 Cells: hESC cells were cultured in 10 µM Rho Kinase inhibitor (DDD00033325, EMD Millipore, Billerica, Mass.) 24 h prior to electroporation. Electroporation was performed using the Neon kit (Invitrogen), according to the manufacturer instruction. Briefly, on the day of electroporation, hESC were digested with Accutase (Sigma-Aldrich) for 1-2 min until colonies lifted. Importantly, colonies were not dissociated into a single cell suspension. After colonies were harvested, wet pellets were kept on ice for 15 min, and then resuspended in electroporation buffer containing gene targeting plasmids. Electroporation parameters were as follows: voltage: 1400 ms; interval: 30 ms; 1 pulse. Following electroporation, cell colonies were slowly transferred to mTeSR1 medium containing 10 µM Rho Kinase inhibitor, and then kept at room temperature for 20 min before plating on Matrigel-coated dishes and further cultured.

For analysis of clonally derived colonies, electroporated hESC were grown to subconfluence, passaged as described in the previous paragraph and plated at a density of 500 cells per 35 mm dish. Subsequently, single colonies were isolated by manual picking and further cultured.

Generation of Constitutively Expressed GFP ESC Lines: The H7 human ESC line (WiCell) was maintained in mTeSR1 (Stem Cell Technologies) media on Matrigel substrate. Prior to cell passaging, cells were subjected to a brief pre-treatment with blebbistatin (>5 min) to increase cell viability, treated with Accutase for 7 min, triturated to a single cell suspension, quenched with an equal volume of mTesR, pelleted at 80×g for 5 min and resuspended in mTeSR containing blebbistatin. 1×10$^6$ cells were pelleted, media carefully removed and cells placed on ice for 10-15 min. 10 µg of AAV-CAGGSEGFP donor vector (#22212, Addgene) containing homology to the AAVS1 safe-harbor locus, plus 5 µg each of hAAVS1 1R+L TALENs (#35431 and 35432, Addgene) (Hockemeyer et al. (2009) *Nat. Biotechnol.* 27: 851-857; Sanjana et al. (2012) *Nature Protocols* 7: 171-192) in R-buffer were electroporated with a 100 µl tip-type using the Neon Transfection System (Life Technologies) with the following parameters: 1500V, 20 ms pulse and 1 pulse. Cells were then added gently to 1 ml of medium and incubated at room temperature for 15 min and then plated onto Matrigel-coated 35 mm dishes containing mTeSR and 5 µM blebbistatin. After 2 days, cells were seeded at a density of 1×10$^4$ after which time stable clonal sublines were manually selected with a fluorescence equipped Nikon TS100 epifluorescence microscope.

Surveyor Assay and Sequencing Analysis for Genome Modification: For Surveyor analysis, genomic DNA was extracted by resuspending cells in QuickExtract solution (Epicentre, Madison, Wis.), incubating at 65° C. for 15 min, and then at 98° C. for 10 min. The extract solution was cleaned using DNA Clean and Concentrator (Zymo Research, Irvine, Calif.) and quantitated by NanoDrop (Thermo Fisher Scientific). The genomic region surrounding the CRISPR target sites was amplified from 100 ng of genomic DNA using Phusion DNA polymerase (New England Biolabs). Multiple independent PCR reactions were pooled and purified using Qiagen MinElute Spin Column following the manufacturer's protocol (Qiagen, Valencia, Calif.). An 8 µl volume containing 400 ng of the PCR product in 12.5 mM Tris-HCl (pH 8.8), 62.5 mM KCl and 1.875 mM MgCl$_2$ was denatured and slowly reannealed to allow for the formation of heteroduplexes: 95° C. for 10 min, 95° C. to 85° C. ramped at −1.0° C./sec, 85° C. for 1 sec, 85° C. to 75° C. ramped at −1.0° C./sec, 75° C. for 1 sec, 75° C. to 65° C. ramped at −1.0° C./sec, 65° C. for 1 sec, 65° C. to 55° C. ramped at −1.0° C./sec, 55° C. for 1 sec, 55° C. to 45° C. ramped at −1.0° C./sec, 45° C. for 1 sec, 45° C. to 35° C. ramped at −1.0° C./sec, 35° C. for 1 sec, 35° C. to 25° C. ramped at −1.0° C./sec, and then held at 4° C. 1 µl of Surveyor Enhancer and 1 µl of Surveyor Nuclease (Transgenomic, Omaha, Nebr.) were added to each reaction, incubated at 42° C. for 60 min, after which, 1 µl of the Stop Solution was added to the reaction. 1 µl of the reaction was quantitated on the 2100 Bioanalyzer using the DNA 1000 chip (Agilent, Santa Clara, Calif.). For gel analysis, 2 µl of 6× loading buffer (New England Biolabs) was added to the remaining reaction and loaded onto a 3% agarose gel containing ethidium bromide. Gels were visualized on a Gel Logic 200 Imaging System (Kodak, Rochester, N.Y.), and quantitated using ImageJ v. 1.46. NHEJ frequencies were calculated using the binomial-derived equation:

$$\% \text{ gene modification} = 1 - \sqrt{1 - \frac{(a+b)}{(a+b+c)}} \times 100$$

where the values of "a" and "b" are equal to the integrated area of the cleaved fragments after background subtraction and "c" is equal to the integrated area of the un-cleaved PCR product after background subtraction (Guschin et al. (2010) *Methods in Molecular Biology* 649: 247-256).

Example 3

FIG. 11A, FIG. 11B, and FIG. 11C show a Hammerhead Ribozyme to generate the 5' end of a guide RNA. A 5' cis-hammerhead ribozyme (SEQ ID NO: 49) and gRNA (SEQ ID NO: 50) are depicted in FIG. 11A. The sequences of the hammerhead ribozyme are indicated, and the nucleotides important for catalysis are indicated (critical in red, important in orange). The location of cleavage is indicated by the arrow. Upon ribozyme cleavage (lower), the resulting gRNA is released, without constraint to any nucleotide at the newly formed 5' position. Constructs shown to express the hammerhead-gRNA are shown in FIG. 11B. A promoter, generally a pol III promoter like U6, H1, or T7, can be used to express the 5' cis-hammerhead ribozyme, which after self-cleavage will release the gRNA. Targeting of two loci are shown in FIG. 11C with the Surveyor Assay (HH1+CGG PAM sequence=SEQ ID NO: 51; HH2+AGG PAM sequence=SEQ ID NO: 52), with successful cleavage (arrows) by a 5' cis-hammerhead ribozyme.

FIG. 12 shows a regulatable CRISPR construct, using aptazymes to process gRNAs in the presence of specific aptamers. In particular, FIG. 12 depicts the theophylline aptamer (orange) fused to helix II of the hammerhead ribozyme forming the theophylline aptazyme, which is 5' of the gRNA (blue). Binding of theophylline stabilizes helix II that then allows for hammerhead self-cleavage, and freeing the gRNA. The gRNA, along with Cas9, is now able to target cleavage by the CRISPR system.

Methods

Plasmid Construction: To generate the 5' cis-hammerhead construct driven by the U6, H1, or T7 promoter, the hammerhead sequence (GTACGTTTCCTCTGATGAGTC-CCAAATAGGACGAAACGCGCTTCGGTGCG TC; SEQ ID NO:53) was placed downstream of the promoter, and upstream of the gRNA target and scaffold. To form helix I, 10 nucleotides complementary to the gRNA target sequence were placed 5' of the hammerhead sequence, which would then bind to the complementary sequence found in the gRNA (FIG. 12). To generate the various gRNAs used in this study, overlapping oligonucleotides were annealed and amplified by PCR using two-step amplification Phusion Flash DNA polymerase (Thermo Fisher Scientific, Rockford, Ill.), and subsequently purified using Carboxylate-Modified Sera-Mag Magnetic Beads (Thermo Fisher Scientific) mixed with 2× volume 25% PEG and 1.5M NaCl. The purified PCR products were then resuspended in H$_2$O and quantitated using a NanoDrop 1000 (Thermo Fisher Scientific). The gRNA-expressing constructs were generated using the Gibson Assembly (New England Biolabs, Ipswich, Mass.) (Gibson et al. (2009) *Nature Methods* 6:343-345) with slight modifications. The total reaction volume was reduced from 20 µl to 2 µl.

Cell Culture: The hESC line H7 and IMR-90 iPS cells (WiCell, Madison Wis.) were maintained by clonal propagation on growth factor reduced Matrigel (BD Biosciences, Franklin Lakes, N.J.) in mTeSR1 medium (Stem Cell Technologies, Vancouver, BC), in a 10% CO$_2$/5% O2 incubator according to previously described protocols (Walker et al. (2010) *Nat. Commun.* 1:71; Maruotti et al. (2013) *Stem Cells Translational Medicine* 2:341-354). For passaging, hESC colonies were first incubated with 5 µM blebbistatin (Sigma-Aldrich, St. Louis, Mo.) in mTeSR1, and then collected after 5-10 min treatment with Accutase (Sigma-Aldrich). Cell clumps were gently dissociated into a single cell suspension and pelleted by centrifugation. Thereafter, hPSCs were re-suspended in mTeSR1 with blebbistatin and plated at approximately 1,000-1,500 cells/cm$^2$. Two days after passage, medium was replaced with mTeSR1 (without blebbistatin) and changed daily.

Human embryonic kidney (HEK) cell line 293T (Life Technologies, Grand Island, N.Y.) was maintained at 37° C. with 5% CO$_2$/20% O2 in Dulbecco's modified Eagle's Medium (DMEM) (Invitrogen) supplemented with 10% fetal bovine serum (Gibco, Life Technologies, Grand Island, N.Y.) and 2 mM GlutaMAX (Invitrogen).

Gene Targeting of H7 Cells: hESC cells were cultured in 10 µM Rho Kinase inhibitor (DDD00033325, EMD Millipore, Billerica, Mass.) 24 h prior to electroporation. Electroporation was performed using the Neon kit (Invitrogen), according to the manufacturer instruction. Briefly, on the day of electroporation, hESC were digested with Accutase (Sigma-Aldrich) for 1-2 min until colonies lifted. Importantly, colonies were not dissociated into a single cell suspension. After colonies were harvested, wet pellets were kept on ice for 15 min, and then resuspended in electroporation buffer containing gene targeting plasmids. Electroporation parameters were as follows: voltage: 1400 ms; interval: 30 ms; 1 pulse. Following electroporation, cell colonies were slowly transferred to mTeSR1 medium containing 10 µM Rho Kinase inhibitor, and then kept at room temperature for 20 min before plating on Matrigel-coated dishes and further cultured.

For analysis of clonally derived colonies, electroporated hESC were grown to subconfluence, passaged as described in the previous paragraph and plated at a density of 500 cells per 35 mm dish. Subsequently, single colonies were isolated by manual picking and further cultured.

Generation of Constitutively Expressed GFP ESC Lines: The H7 human ESC line (WiCell) was maintained in mTeSR1 (Stem Cell Technologies) media on Matrigel substrate. Prior to cell passaging, cells were subjected to a brief pre-treatment with blebbistatin (>5 min) to increase cell viability, treated with Accutase for 7 min, triturated to a single cell suspension, quenched with an equal volume of mTesR, pelleted at 80×g for 5 min and resuspended in mTesR containing blebbistatin. 1×10$^6$ cells were pelleted, media carefully removed and cells placed on ice for 10-15 min. 10 µg of AAV-CAGGSEGFP donor vector (#22212, Addgene) containing homology to the AAVS1 safe-harbor locus, plus 5 µg each of hAAVS1 1R+L TALENs (#35431 and 35432, Addgene) (Hockemeyer et al. (2009) *Nat. Biotechnol.* 27: 851-857; Sanjana et al. (2012) *Nature Protocols* 7: 171-192) in R-buffer were electroporated with a 100 µl tip-type using the Neon Transfection System (Life Technologies) with the following parameters: 1500V, 20 ms pulse and 1 pulse. Cells were then added gently to 1 ml of medium and incubated at room temperature for 15 min and then plated onto Matrigel-coated 35 mm dishes containing mTeSR and 5 µM blebbistatin. After 2 days, cells were seeded at a density of 1×10$^4$ after which time stable clonal sublines were manually selected with a fluorescence equipped Nikon TS100 epifluorescence microscope.

Surveyor Assay and Sequencing Analysis for Genome Modification: For Surveyor analysis, genomic DNA was extracted by resuspending cells in QuickExtract solution (Epicentre, Madison, Wis.), incubating at 65° C. for 15 min, and then at 98° C. for 10 min. The extract solution was cleaned using DNA Clean and Concentrator (Zymo Research, Irvine, Calif.) and quantitated by NanoDrop (Thermo Fisher Scientific). The genomic region surrounding the CRISPR target sites was amplified from 100 ng of genomic DNA using Phusion DNA polymerase (New England Biolabs). Multiple independent PCR reactions were pooled and purified using Qiagen MinElute Spin Column following the manufacturer's protocol (Qiagen, Valencia, Calif.). An 8 µl volume containing 400 ng of the PCR product in 12.5 mM Tris-HCl (pH 8.8), 62.5 mM KCl and 1.875 mM MgCl$_2$ was denatured and slowly reannealed to allow for the formation of heteroduplexes: 95° C. for 10 min, 95° C. to 85° C. ramped at −1.0° C./sec, 85° C. for 1 sec, 85° C. to 75° C. ramped at −1.0° C./sec, 75° C. for 1 sec, 75° C. to 65° C. ramped at −1.0° C./sec, 65° C. for 1 sec, 65° C. to 55° C. ramped at −1.0° C./sec, 55° C. for 1 sec, 55° C. to 45° C. ramped at −1.0° C./sec, 45° C. for 1 sec, 45° C. to 35° C. ramped at −1.0° C./sec, 35° C. for 1 sec, 35° C. to 25° C. ramped at −1.0° C./sec, and then held at 4° C. 1 µl of Surveyor Enhancer and 1 µl of Surveyor Nuclease (Transgenomic, Omaha, Nebr.) were added to each reaction, incubated at 42° C. for 60 min, after which, 1 µl of the Stop Solution was added to the reaction. 1 µl of the reaction was quantitated on the 2100 Bioanalyzer using the DNA 1000 chip (Agilent, Santa Clara, Calif.). For gel analysis, 2 µl of 6× loading buffer (New England Biolabs) was added to the remaining reaction and loaded onto a 3% agarose gel containing ethidium bromide. Gels were visualized on a Gel Logic 200 Imaging System (Kodak, Rochester, N.Y.), and quantitated using ImageJ v. 1.46. NHEJ frequencies were calculated using the binomial-derived equation:

$$\% \text{ gene modification} = 1 - \sqrt{1 - \frac{(a+b)}{(a+b+c)}} \times 100$$

where the values of "a" and "b" are equal to the integrated area of the cleaved fragments after background subtraction and "c" is equal to the integrated area of the un-cleaved PCR product after background subtraction (Guschin et al. (2010) *Methods in Molecular Biology* 649: 247-256).

Example 4

Summary

Retinitis pigmentosa (RP) is an inherited retinal degenerative disease in which dysfunction and death of retinal photoreceptor cells (rods and cones) leads to vision loss and potentially to blindness. There are both Autosomal Recessive and Autosomal Dominant genetic forms of RP (ARRP and ADRP, respectively). In ARRP there are mutations in both copies of the gene responsible for the disease (for most genes, one copy of the gene is inherited from one's mother and the other from one's father). The disease causing mutations associated with ARRP generally lead to the loss of function of the gene involved, i.e. retinal degeneration is due to loss of the ability of the gene involved to perform its normal function. In such cases it is pretty clear, at least in theory, what needs to be done to develop an appropriate treatment—one needs to replace the lost gene function. Elegant examples of this approach are the ongoing human treatment studies for Leber Congenital Amaurosis (LCA) in which gene therapy with an adeno-associated virus (AAV) is being used to replace the function of the defective RPE65 gene that causes the disease.

In ADRP, in distinction to ARRP, only one of the two copies of the disease-causing gene is mutated. In most cases, this single mutated gene does not cause retinal degeneration because it has lost function; rather, it causes disease because the mutation leads to production of a gene-product that has gained a new function, a function that is toxic or harmful to rod and/or cone photoreceptor cells. This situation makes gene replacement strategies more complex as introduction of a functional gene is not enough; effective therapy requires both developing an approach to get rid of expression of the "bad" gene-product produced from the gene with the toxic mutation and maintaining the function of the un-mutated copy of the gene, which geneticists refer to as the "wild-type" (WT) gene.

At present, there are no FDA-approved treatments for ADRP. Most of the ongoing laboratory and animal research studies take a two-step approach: 1) eliminate the function of both the mutated and WT copies of the gene, and then 2) introduce, usually via AAV-mediated gene therapy, a new "hardened" form of the WT gene that is resistant to the therapy used in the first step that destroyed the endogenous WT gene.

The presently disclosed subject matter provides a novel strategy for ADRP treatment, one that utilizes CRISPR/Cas9 gene editing to precisely target editing of a living organism's genomic information, i.e. it allows therapeutic modulation of one's genes. The presently disclosed methods use CRISPR/Cas9 gene editing to specifically alter the mutated copy of the disease-causing gene so that it does not express its toxic gene product, while not affecting expression of the WT gene. For example, a mutant version of the rhodopsin gene associated with ADRP (P23H) can be specifically targeted, changing its sequence so that it no longer expresses the toxic gene product. In some embodiments, the CRISPR/Cas9 components are delivered to the eye within a single AAV viral particle. This system is tested in the P23H rhodopsin mouse mutant model of ADRP. These studies validate a new approach for gene therapy based on custom genetic engineering of retinal cells for the treatment of ADRP. The presently disclosed subject matter is applicable to various forms of ADRP as well as other autosomal dominantly inherited retinal dystrophies.

Specific Goals

The autosomal dominant form of retinitis pigmentosa (ADRP) constitutes approximately 30-40% of all cases of RP, and among ADRP patients the most commonly mutated RP-associated gene is the one that encodes the rod visual pigment rhodopsin (Dryja et al. (1990) *The New England Journal of Medicine* 323, 1302-1307; Dryja et al. (1990) *Nature* 343, 364-366). The presently disclosed subject matter provides an approach to treating ADRP by using CRISPR/Cas9 gene editing Technology (Doudna & Charpentier (2014) *Science* 346, 1258096; Hsu et al. (2014) *Cell* 157, 1262-1278) in which the RNA guided Cas9 endonuclease is used in conjunction with customizable small guide RNAs (gRNAs) to target and cleave the mutant rhodopsin allele. Error-prone nonhomologous end joining (NHEJ) specifically knocks out expression of the mutant allele, without affecting the normal allele. The needed components can be delivered to photoreceptors by a single AAV5, an AAV serotype with documented performance in mammalian rods. Even if expression of only 50% of the wild-type level of rhodopsin occurs, animal data suggests that this is sufficient to provide clinically useful rod function (Liang et al. *The Journal of Biological Chemistry* 279, 48189-48196).

While CRISPR targeting of disease mutations has been shown to be effective in vitro and in vivo, through mouse and other animal studies, all current approaches are still far from clinical use due in large part to delivery constraints. AAV vectors are the most frequently used viral vectors in ocular gene therapy (Dalkara & Sahel (2014) *Comptes Rendus Biologies* 337, 185-192; Day et al. (2014) *Advances in Experimental Medicine and Biology* 801, 687-693; Willett & Bennett (2013) *Frontiers in Immunology* 4, 261; Dinculescu et al. (2005) *Human Gene Therapy* 16, 649-663). Several features make AAV an attractive choice: the virus is nonpathogenic, it infects both dividing and non-dividing cells, expression can persist for long periods of time, and it is particularly noteworthy for its history of safety, efficacy and a general lack of toxicity in clinical trials. Additionally, combinations of variant AAV serotypes and promoters that are effective in targeting photoreceptor cells after intravitreal injection are being developed. However, since in their current state these vectors trigger an immune response, and lack efficient panretinal tropism towards photoreceptors in the human-sized eye (Kotterman et al. (2015) *Gene therapy* 22, 116-126; Mowat et al. (2014) *Gene Therapy* 21, 96-105; Dalkara et al. (2013) *Science Translational Medicine* 5, 189ra176), the focus will be on the already well-characterized use of AAV5 vector administered by subretinal injection.

The AAV genome is a 4.7 kb single-stranded DNA molecule that can be modified to carry up to 5.2 kb of recombinant DNA, although pushing this limit leads to reduced packaging efficiency and deleted inserts (Berns et al. (1986) *Fundamental Virology*, ed B. N. Fields and Knipe, D. M., 545-562 Raven Press). Due to the large size of the gene encoding the commonly used Cas9 protein (4.1 kb) itself, delivery with a gRNA, including promoter, terminator and viral inverted terminal repeat (ITR) sequences necessary for expression through a single viral vector, is currently limited by this AAV packaging capacity. Indeed, reconstitution of the active CRISPR complex necessitates co-transduction, which is less efficient than a single transduction. Additionally, this requires a larger viral dose, which could potentially induce a larger immune response and associated toxicity. Also, it is likely that delivery of a second viral vector in human trials would lead to additional challenges for FDA approval.

The development of CRISPR/Cas9 technology has revolutionized the field of gene editing. Earlier methods of genome-editing technologies, such as zinc finger nucleases (ZFN) and transcription activator-like effectors nucleases (TALEN), empowered the ability to generate targeted genome modifications and offer the potential to correct disease mutations with precision. While effective, these technologies are encumbered by practical limitations as both ZFN and TALEN pairs require synthesizing large and unique recognition proteins for a given DNA target site. A number of groups have recently reported high-efficiency genome editing through the use of an engineered type II CRISPR/Cas9 system that circumvents these key limitations (Jinek et al. (2012) *Science* 337, 816-821; Cong et al. (2013) *Science* 339, 819-823; Mali et al. (2013) *Science* 339, 823-826). The CRISPR/Cas9 system is composed of a guide RNA (gRNA) that targets the Cas9 nuclease to sequence-specific DNA. Since CRISPR/Cas9 genome editing relies upon a short synthetic gRNA for genomic targeting rather than unique combinations of DNA binding domains within the nuclease as is required by ZFNs and TALENs, the time consuming and arduous task of making the constructs necessary for ZFN and TALEN expression is eliminated. Generating constructs for the CRISPR/Cas9 system is simple and fast, and targets can be multiplexed. Cleavage by the CRISPR system requires complementary base pairing of the gRNA to a 20-nucleotide DNA sequence and the requisite protospacer-adjacent motif (PAM), a short nucleotide motif found 3' to the target site. One can, theoretically, target any unique $N_{20}$-PAM sequence in the genome using CRISPR technology. Currently, the least restrictive and most commonly used Cas9 protein is from *S. pyogenes*, which recognizes the sequence NGG, and thus, the CRISPR targeting sequence is $N_{20}$NGG. The degenerate N in the NGG sequence, means that given a unique sequence of 20 nucleotides ($N_{20}$), Cas9 would cleave $N_{20}$AGG, $N_{20}$TGG, $N_{20}$CGG, and $N_{20}$GGG equally which can be an issue for precise targeting of alleles.

For in vivo rhodopsin gene targeting, the required CRISPR/Cas9 effector molecules are delivered to rod cells by subretinal administration of appropriately engineered AAVS vectors. Serotype 5 vector has been shown to be very efficient at transducing both nonhuman primate (Mancuso et al. (2009) *Nature* 461, 784-787) and canine (Beltran et al. (2012) *Proceedings of the National Academy of Sciences of the United States of America* 109, 2132-2137) photoreceptors and to be capable of mediating retinal therapy. Although capsid modified AAV vectors can penetrate to photoreceptors from the vitreous in the mouse (Petrs-Silva et al. (2011) *Molecular Therapy: the Journal of the American Society of Gene Therapy* 19, 293-301), thus far they have been unable to be similarly penetrant in dogs or nonhuman primates (unpublished observations).

An important challenge in delivering Cas9 and guide RNAs via AAV is that the DNA required to express both components exceeds the packaging limit of AAV, approximately 4.7-4.9 kb, while the DNA required to express Cas9 and the gRNA, by conventional methods, exceeds 5 kb (promoter, ~500 bp; spCas9, 4,140 bp; Pol II terminator, ~250 bp; U6 promoter, ~315 bp; and the gRNA, ~100 bp). Swiech et al. (2015, *Nature Biotechnology* 33, 102-106) addressed this challenge by using a two-vector approach: one AAV vector to deliver the Cas9 and another AAV vector for the delivery of gRNA. However, the double AAV approach in this study took advantage of a particularly small promoter, the murine Mecp2 promoter, which although expressed in retinal cells is not expressed in rods (Song et al. (2014) *Epigenetics & chromatin* 7, 17; Jain et al. (2010) *Pediatric Neurology* 43, 35-40). Thus this system as constructed would not be suitable for most cases of ADRP. The presently disclosed subject matter provides a single vector approach for retinal gene editing that should increase efficiency, target photoreceptors specifically, and reduce potential toxicity from viral load delivery.

Results

The H1 promoter, rather than the more traditionally used U6 promoter, has been used to direct gRNA transcription and allows an approximate doubling of the available CRISPR gene targeting space (Ranganathan et al. (2014) *Nature Communications* 5, 4516). Notably, a lower propensity for off-target cutting was detected, suggesting that the H1 promoter is more favorable for therapeutic approaches. During these studies, the presence of a protein-coding gene (PARP-2) in close genomic proximity to the endogenous H1RNA gene was noted (Baer et al. (1990) *Nucleic Acids Research* 18, 97-103; Myslinski et al. (2001) *Nucleic Acids Research* 29, 2502-2509). The sequence between the start of the H1RNA (a pol III RNA transcript) and the PARP-2 gene (a pol II transcript) is 230 bp (FIG. 13), indicating that this relatively small sequence can function as a compact bidirectional promoter. It is believed that this is the only bidirectional promoter sequence in mammalian genomes that can direct both a pol II and a pol III transcript and can be used to overcome the size hurdles of packaging both CRISPR components into a single AAV.

To develop use of H1 as a bidirectional pol II/III promoter for dual Cas9/gRNA expression, and because its polI III activity is already well characterized, an eGFP reporter construct was created to better optimize its pol II activity (FIG. 14). The initial results in human (HEK293) and mouse cells (NIH3T3) demonstrated a weak, but clearly detectable GFP fluorescence, indicating that the H1 promoter could direct pol II expression, albeit weakly. Using this GFP reporter system, pol II expression was increased while maintaining compactness of the promoter by evaluating the three variable components in the system: the promoter sequence, the 5'UTR, and the terminator sequence. Testing H1 promoter sequences from different organisms indicated that both mouse (176 bp) and rat (207 bp) sequences were able to drive stronger GFP expression than the human H1 promoter (~7 and ~6-fold higher, respectively). However, since the goal is to derive a system for use with human cells in vivo, human promoter sequences were used where possible. To evaluate different terminator sequences, seven different sequences were tested and it was found that the SV40 (240 bp) terminator and a 49 bp synthetic poly(A) sequence (SPA) (Levitt et al. (1989) *Genes & Development* 3, 1019-1025) were both functional for GFP expression. While optimizing translation efficiency through modification of the 5'UTR to improve reporter expression, it was found that insertion of a 50 bp sequence taken from the beta-globin 5'UTR sequence was able to significantly improve reporter expression. Consistent with this notion, the simple insertion of 9 bases encoding a strong Kozak sequence (Kozak (1987) *Nucleic Acids Research* 15, 8125-8148) (5'-GCCGCCACC-3') was sufficient to approximate these levels (FIG. 15.)

Based on the information derived from these GFP-based optimization experiments, targeting constructs were generated using the human H1 promoter sequence to simultaneously express the Cas9 protein and a targeting gRNA. To test the ability of these bidirectional constructs to direct cleavage in cells, NIH3T3 cells were electroporated with either a standard two plasmid approach (pCAAGS:Cas9 and H1:gRNA), or with the single-plasmid system expressing both components. Two different loci in the mouse genome were targeted. Forty-eight hours after electroporation, genomic DNA was harvested and a T7 Endo I (T7EI) assay (Ran et al. (2013) *Nature protocols* 8, 2281-2308) was performed to quantitate the levels of genomic modification. The T7EI assay was used rather than the more traditional Surveyor assay because it has been reported to be more sensitive in detecting deletions (Vouillot et al. (2015) G3). It was found that CRISPR cleavage could be effectively targeted to these two loci using the compact bidirectional system that is approximately 4.7 kb, well within the packaging capacity of AAV (FIG. 16A and FIG. 16B). Further demonstrating the applicability and relevance of this targeting strategy in human cells, there is data for Cas9 targeting in the human H7 embryonic stem cell line. By using the mouse H1 promoter instead of the human sequence, and the SPA terminator instead of the SV40 terminator sequence, the size of the targeting constructs can theoretically be reduced by another 200 bp. These sequence reductions could allow for more efficient packaging, or potentially give added space for sequence modifications that could boost, reduce, and even regulate expression of the Cas9 system; modifications that could be important for reducing potential off-target effects. Bidirectional plasmids have been generated with a unique restriction site that allows for simple target insertion using the Gibson cloning method (NEB), along with flanking NotI sites that can be easily cloned into the ITR containing vectors from the AAV Helper-free System (Agilent).

Design and optimize Cas9 and gRNA promoter, RNA processing, and structural elements so that they can effectively be expressed from a single AAV vector system and generate appropriate GMP-like preclinical vector.

Through the combination of the bi-directional H1 promoter to simultaneously drive expression of Cas9 and gRNA, and optimization efforts, substantial progress has already been made in reducing the size of CRISPR delivery under the AAV packaging capacity. The various combinations from alternative promoter sequences, 5'/3' UTR modifications, and different gRNAs provide a toolkit to test the potential spectrum of targeting efficiencies.

Once the constructs are further optimized in terms of size, expression, and cutting efficiency, they can be used to generate AAV vectors for testing in vitro and in vivo. The constructs being used for the optimization studies contain a unique restriction site that allows for simple target insertion, along with flanking NotI sites that allow cloning into the ITR containing vector plasmids for AAV production. High titer GMP-like preclinical AAVS vector for the cell culture and mouse, studies can be generated in an independent vector production facility, using a helper-free, plasmid transfection method and purified by previously developed techniques (we developed (Dryja et al. (1990) *The New England Journal of Medicine* 323, 1302-1307; Dryja et al. (1990) *Nature* 343, 364-366). Each viral preparation can be produced using the pDG mini-Ad plasmid DNA helper system, which eliminates WT adenovirus and replication-competent AAV contamination in the final vector. Vectors are purified by iodixanol gradient centrifugation followed by Q-column FPLC chromatography. To establish the GMP-like purity of the AAV vector stocks, each vector can be subjected to a standardized battery of physical and biological assays including assessment of purity, bioburden, sterility, DNA containing particle titer, infectious titer, particle-to-infectivity ratio and potential contamination by replication-competent AAV.

Although the studies with the H1 promoter to date have indicated a low level of off-target effects (Ranganathan et al. (2014) *Nature Communications* 5, 4516), since the constructs are being developed with the goal of eventual clinical use, they should be carefully monitored for potential off-target activity (Wu et al. (2014) *Quantitative Biology* 2, 59-70). For this purpose, several complementary approaches can be pursued. Taking a bioinformatics approach, all the potential CRISPR sites in the human and mouse genome were determined using a custom Perl script written to search both strands and overlapping occurrences of the 23-mer CRISPR sequence site (Ranganathan et al., manuscript in preparation, 2015). For example, in the human genome, an initial set of 137,409,562 CRISPR sites were identified after filtering out repetitive sequences. Each site was then scored according to a custom algorithm which assigns values based on the uniqueness of the 23-base sequence biased towards the 3' or PAM end (seed region) (Jinek et al. (2012) *Science* 337: 816-821). Finally, the propensity for each site to exhibit off-target effects was calculated by using Bowtie (Langmead et al. (2009) *Genome Biology* 10, R25) to realign each CRISPR site back onto the genome allowing up to three base mismatches throughout the targeting sequence. Using the computationally predicted off-targets, each gRNA can be tested for any spurious targeting. PCR primers flanking the predicted potential off-target sites can be used to amplify the genomic sequence that can then be tested for cleavage efficiency with the T7EI assay. This will allow for monitoring of the targeting accuracy for the optimization experiments both in vitro and in vivo. Less than 0.5% off-target cutting will be the aim, although less than 5% will be acceptable.

While the focus has been on standard Cas9 targeting, alternative approaches are also considered, including targeting alternative PAM sequences. Cas9 has been reported to target PAM motifs with NAG in addition to the standard NGG sequences (Hsu et al. (2013) *Nature Biotechnology*, doi:10.1038/nbt.2647). Two CRISPR sequences in the human sequence and three targeting sequences in the mouse genome overlapping that P23H mutation have been identified, which could provide additional targeting sites. While NAG PAM sites are expected to target less efficiently than NGG sites (Zhang et al. (2014) *Scientific Reports* 4, 5405), this may provide a mechanism to titrate dosage, which may be valuable if it is determined that the constructs have significant off-target effects. The five sequences using the NAG PAM site can be cloned initially into pH1v126 using the Gibson assembly (NEB). The two human sequences can be co-transfected (Lipofectamine 3000) with Cas9 plasmid into 293 cells, while the mouse plasmids can be electroporated (Invitrogen, Neon) with Cas9 plasmid into NIH3T3 cells. To detect gRNA activity, the rates of indel mutations introduced by NHEJ at the Cas9 cleavage sites between the canonical NGG as well as non-canonical NAG sites can be quantified.

An alternative therapeutic approach, known as CRISPRi, which utilizes a nuclease-dead version of Cas9 (dCas9) to specifically repress expression of the P23H allele, can also be used (Qi et al. (2013) *Cell* 152, 1173-1183; Gilbert et al. (2013) *Cell* 154, 442-451; Larson et al. (2013) *Nature Protocols* 8, 2180-2196; Fuller et al. (2014) *Advances in Experimental Medicine and Biology* 801, 773-781). Instead of inducing cleavage, dCas9 stays bound tightly to the DNA sequence, and when targeted inside an actively transcribed gene, inhibition of pol II progression through a steric hindrance mechanism can lead to efficient transcriptional repression. By achieving therapeutic repression of P23H without inducing DNA breaks, and given constitutive AAV expression, AAVS delivery of a transcriptional inhibitor could be favorable from both a gene therapy and regulatory hurdle standpoint. Transcriptional repression by CRISPRi can be optimized using qRT-PCR to measure allele-specific expression of rhodopsin.

Validate the ability of the developed AAV5 vector to cut and knock out expression of the mutant rhodopsin allele in vitro using primary photoreceptor cultures from the P23H mouse.

Primary mouse photoreceptor cell cultures can be used to validate the targeting constructs in vitro before progressing to animal studies. Postnatal day 2-10 animals can be used to harvest and dissociate the mouse retina for isolating cells for targeting assays. Testing the constructs in the human (h) Rho:GFP mouse (Chan et al. (2004) *Proceedings of the National Academy of Sciences of the United States of America* 101, 9109-9114) can allow further optimization of rhodopsin targeting. The hRho-GFP knock-in mouse contains a human rhodopsin-GFP fusion knocked into the mouse rhodopsin open reading frame (FIG. 17). This partially humanized mouse allows for targeting of human specific sequences in photoreceptor cells. The human rho sequence can be targeted and then the loss of GFP from photoreceptors can be quantitated. Although rhodopsin is being targeted, the GFP reporter is fused in frame, and thus loss of fluorescence serves as a convenient proxy for error-prone NHEJ at the upstream target site. With retinal cell electroporation, 10-20% transfection efficiency is routinely achieved, and in order to enrich for the population of CRISPR modified cells, the transfected population can be sorted based on intensity of a Cas9 fluorescent reporter. Several Cas9 constructs fused with various P2A:reporter proteins have been generated that allow monitoring of fluorescence activity without compromising Cas9 activity. Using retinal cultures from Rho:GFP mice, the Cas9:P2A: mCherry reporter and a targeting gRNA can be electroporated. Then, after 24 hrs of culture, doubly-positive cells can be sorted, thereby enriching for photoreceptors that have been transfected. Forty-eight hours later, cells can be resuspended in QuickExtract buffer (Epicentre) to harvest genomic DNA, and assayed for genomic modification by the T7EI assay. Similarly, targeting of the rhodopsin mutation can be validated using primary photoreceptor cultures from the P23H mouse. Even with a low level of transfection (10%), genome editing can be detected using the T7EI assay if the constructs' targeting efficiency is greater than 10%, consistent with initial results. Additionally, the use of AAVS vectors should yield significantly higher transduction efficiencies.

High-resolution and high-sensitivity site-specific deep sequencing analysis of on-target and off-target sites also will be performed. Genomic sequences flanking the CRISPR target site and predicted off-target sites can be amplified using high-fidelity polymerase (NEB, Phusion) for 15 cycles, and then purified using DNA Clean & Concentrator-5 (Zymo). Purified PCR products can be amplified for 5 cycles to attach Illumina P5 adapters and sample-specific barcodes, purified again, and then quantitated by SYBR green fluorescence, analyzed on a BioAnalyzer, and finally pooled in an equimolar ratio prior to sequencing with a MiSeq Personal Sequencer. To analyze the sequencing data, 300 bp paired-end MiSeq reads will be de-multiplexed using Illumina MiSeq Reporter software, followed by adapter and quality trimming of raw reads. Alignments will be performed on all reads to the wild-type sequence and NHEJ frequency will be calculated by: 100×(number of indel reads/number of indel reads+number of WT reads).

Validate ability of the improved vector from SA2 to cut and knock out expression of the mutant rhodopsin allele in vivo following subretinal injection into P23H mice.

The next step will be to demonstrate in vivo targeting of the P23H Rhodopsin mutation in mice. From bioinformatics efforts, a high scoring CRISPR targeting site has been identified overlapping the mouse P23 codon. The CRISPR site in the form $N_{20}NGG$ falls on the reverse strand: 5'-AG-TACTGTGGGTACTCGAAGGGG-3' (PAM underlined). The P23H mutation is a C→A transversion that changes a CCC Proline codon to a CAC Histidine codon. Unfortunately the location of the mouse P23H mutation within the CRISPR site falls in the N of the NGG PAM motif, the only location in the targeting site that is agnostic to bp identity. Since this means that a CRISPR directed against the P23H sequence would be unable to discriminate between the wild-type and P23H sequence, and targeting would therefore be expected to cut both alleles, an alternative approach has been developed based on the occurrence of single nucleotide polymorphisms (SNPs).

There are ~17 million SNPs (including single base variations, indels, STRs, MNPs, etc.) reported in the human genome (~1 every 180 bp), and this variation is immensely important in personalized genomic medicine contexts. It was reasoned that utilizing natural genetic variations might not only provide a method to target specifically the P23H rhodopsin allele in the mouse model, but also demonstrate a proof-of-concept approach that will likely become even more relevant for future genomic engineering and therapeutic approaches. It was found that the castaneus (Cast) mouse contains a SNP within the proline 23 codon of the rhodopsin gene that differs from the C57BL/6J sequence, and a P23H mutant mouse on a C57BL/6J genetic background was obtained for analysis. The SNP is immediately adjacent to the causative C→A transversion in P23H, which provides an approach for targeting of the dominant P23H allele without targeting the wild-type rhodopsin allele. Since the background for the P23H mutation is C57BL/6J, after one generation of Cast/P23H breeding, heterozygous mice were obtained that contain both a CRISPR targetable rhodopsin P23H allele and, due to the tightly linked SNP difference, a wild-type, CRISPR resistant rhodopsin allele that differs by a single mismatch located at position 20 in the "seed" region of the gRNA target (FIG. 18A, FIG. 18B, and FIG. 18C).

In order to validate the feasibility of the strategy, H1 bidirectional constructs were generated that target either the C57BL/6J proline 23 codon sequence, the one present in the P23H mutant allele, or the proline 23 codon sequence in the Cast mouse, the sequence that will be present in the WT rhodopsin allele of the heterozygous P23H/Cast animals. NIH3T3 cells (which contain the C57BL/6J SNP) were electroporated with both constructs independently, genomic DNA was isolated, and then the T7EI assay was performed to quantitate the level of genome modification. Specific rhodopsin targeting was observed: only the C57BL/6J (i.e. P23H) directed construct yielded significant cutting, with levels of genome modification approaching 50%, which is likely an underestimation of the targeting potential given that the overall electroporation efficiency was under 80% (FIG. 19). In addition to validating the rhodopsin targeting site, and the ability to direct cleavage by the compact bidirectional constructs, these results demonstrated in vitro cutting occurring specifically at the SNP/mutant sequence, as the gRNA based on the Cast rhodopsin sequence, containing a single base mismatch, failed to produce detectable Cas9 cleavage.

It is generally thought that the limiting factor of CRISPR targeting is effective delivery, and AAVS-mediated delivery has been show capable of transducing a majority of photoreceptors, even in large eyes. Given this high transduction rate, gene editing occurring in 50% or more of transduced cells, and that 2/3 of NHEJ events result in frame shift mutations, knock-out of expression of the P23H allele should be achieved in a large plurality of rods and with further optimization, in a majority of rods. Studies suggest that this level of targeting should be sufficient to support photoreceptor survival and maintain a reasonably good level of vision, both through direct preservation of rods and through secondary effects on cone survival (Leveillard et al. (2004) *Nature Genetics* 36, 755-759; Leveillard & Sahel (2010) *Science Translational Medicine* 2, 26ps16; Sahel et al. (2013) *Graefe's archive for clinical and experimental ophthalmology=Albrecht von Graefes Archiv fur klinische and experimentelle Ophthalmologic* 251, 1669-1677). The optimized virus can be injected subretinally into one eye of 10 mice at P15, as previously described (Mao et al. (2012) *Advances in Experimental Medicine and Biology* 723, 199-205; Mao et al. (2012) *Human Gene Therapy* 23, 356-366; Mao et al. (2011) *Human Gene Therapy* 22, 567-575). ERG and SDOCT (Bioptigen) analyses of treated vs partner control eyes can be performed at 2, 6, and 12 weeks post-treatment. Longer-term in-life studies can follow, assuming functional and structural improvement is observed in the treated eyes at 12 weeks. Histological analyses will can be performed at sacrifice, which will include ONL thickness, spidergrams and immunohistological rhodopsin assays for proper localization in outer segments and western blotting for rhodopsin levels.

Off-target effects of the AAVS/CRISPR treatment can be assessed. Whole genome sequencing is the least biased method for the assessment of off-target mutations, and would be ideal for confirming the target sites. The mouse retina from AAV treated and untreated eyes can be harvested and dissociated and genomic DNA can be extracted with the DNeasy Blood & Tissue Kit (Qiagen) and the DNA sheared with a Covaris AFA. The DNA fragments can be end-repaired, A-tailed, and ligated to Illumina barcoded sequencing adaptors. The ligated products can be amplified by PCR to generate barcoded whole-genome sequencing libraries and sequenced on the HiSeq platform (Illumina) to a mean coverage of 15×. Sequencing reads can then be aligned to the human reference genome (hg19/GRCh37) using Burrows-Wheeler Aligner in the 'mem' mode ('bwa mem') with default parameters. Because every CRISPR cleavage event results in a unique mutation, it is assumed that sites of DNA double-strand breaks will not result in the same de novo mutations. Thus discarding all variants shared by multiple samples will allow for filtering in subsequent bioinformatics analysis.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A non-naturally occurring CRISPR-Cas system comprising a single vector comprising an H1 bidirectional promoter, wherein the H1 bidirectional promoter comprises:
   a) control elements that provide for transcription in one direction of at least one nucleotide sequence encoding a CRISPR-Cas system guide RNA (gRNA), wherein the gRNA hybridizes with a target sequence of a DNA molecule in a cell; and
   b) control elements that provide for transcription in the opposite direction of a nucleotide sequence encoding a RNA-directed nuclease, wherein the gRNA targets and hybridizes with the target sequence and directs the RNA-directed nuclease to the DNA molecule, and wherein said system is packaged into a single adeno-associated virus (AAV) particle.

2. The system of claim 1, wherein the target sequence comprises the nucleotide sequence $AN_{19}NGG$, $GN_{19}NGG$, $CN_{19}NGG$, or $TN_{19}NGG$.

3. The system of claim 1, wherein the RNA-directed nuclease is a Cas9 protein.

4. The system of claim 3, wherein the Cas9 protein is codon optimized for expression in the cell and/or is a Type-II Cas9 protein.

5. The system of claim 1, wherein the cell is a eukaryotic cell optionally selected from the group consisting of (i) a mammalian cell, (ii) a human cell, and/or (iii) a retinal photoreceptor cell.

6. The system of claim 1, wherein the expression of one or more gene products is decreased.

* * * * *

UNITED STATES PATENT AND TRADEMARK OFFICE
CERTIFICATE OF CORRECTION

PATENT NO. : 10,369,234 B2
APPLICATION NO. : 15/864715
DATED : August 6, 2019
INVENTOR(S) : Vinod Jaskula-Ranga et al.

Page 1 of 1

It is certified that error appears in the above-identified patent and that said Letters Patent is hereby corrected as shown below:

In the Specification

At Column 1, Line 16, please insert:
--This invention was made with government support under grants T32 EY007143, R01 EY009769, and P30 EY001765 awarded by the National Institutes of Health. The government has certain rights in the invention.--

Signed and Sealed this
Eleventh Day of February, 2020

Andrei Iancu
*Director of the United States Patent and Trademark Office*